US008178580B2

(12) United States Patent
Garceau et al.

(10) Patent No.: US 8,178,580 B2
(45) Date of Patent: May 15, 2012

(54) FORMULATIONS AND METHODS FOR TREATING AMYLOIDOSIS

(75) Inventors: Denis Garceau, Kirkland (CA); Wendy Hauck, Baie d'Urfe (CA); Richard Briand, Laval (CA)

(73) Assignee: Kiacta Sarl, St-Legier (CH)

( * ) Notice: Subject to any disclaimer, the term of this patent is extended or adjusted under 35 U.S.C. 154(b) by 0 days.

(21) Appl. No.: 11/405,348

(22) Filed: Apr. 17, 2006

(65) Prior Publication Data
US 2006/0252829 A1  Nov. 9, 2006

Related U.S. Application Data

(60) Provisional application No. 60/671,866, filed on Apr. 15, 2005.

(51) Int. Cl.
*A01N 41/10* (2006.01)
*A01N 37/00* (2006.01)
*A61K 31/10* (2006.01)
*A61K 31/185* (2006.01)

(52) U.S. Cl. ........................................ 514/553; 514/709

(58) Field of Classification Search .................. 514/533, 514/553, 709
See application file for complete search history.

(56) References Cited

U.S. PATENT DOCUMENTS

| | | | |
|---|---|---|---|
| 2,531,468 A | 11/1950 | Reynolds et al. | |
| 3,218,352 A | 11/1965 | Freifelder et al. | |
| 3,236,881 A | 2/1966 | Distler et al. | |
| 3,658,966 A | 4/1972 | Tsunoo et al. | |
| 3,920,833 A | 11/1975 | Cook et al. | |
| 4,255,448 A | 3/1981 | Fariello | |
| 4,355,043 A | 10/1982 | Durlach | |
| 4,448,779 A | 5/1984 | Blanchard et al. | |
| 4,528,184 A | 7/1985 | Kurono et al. | |
| 4,713,376 A | 12/1987 | Kuzuya et al. | |
| 4,737,353 A | 4/1988 | Flanigen et al. | |
| 4,847,082 A | 7/1989 | Sabin | |
| 4,956,347 A | 9/1990 | Ban et al. | |
| 4,990,606 A | 2/1991 | Gennari et al. | |
| 5,064,923 A | 11/1991 | Kashihara et al. | |
| 5,164,295 A | 11/1992 | Kisilevsky et al. | |
| 5,192,753 A | 3/1993 | McGeer et al. | |
| 5,242,932 A | 9/1993 | Gandy et al. | |
| 5,276,059 A | 1/1994 | Caughey et al. | |
| 5,318,958 A | 6/1994 | Kisilevsky et al. | |
| 5,342,977 A | 8/1994 | Baschang et al. | |
| 5,385,915 A | 1/1995 | Buxbaum et al. | |
| 5,430,052 A | 7/1995 | Higashiura et al. | |
| 5,643,562 A * | 7/1997 | Kisilevsky et al. | ........ 424/78.31 |
| 5,668,117 A | 9/1997 | Shapiro | |
| 5,728,375 A * | 3/1998 | Kisilevsky et al. | ........ 424/78.31 |
| 5,780,510 A | 7/1998 | Carney | |
| 5,837,672 A | 11/1998 | Schenk et al. | |
| 5,840,294 A * | 11/1998 | Kisilevsky et al. | ........ 424/78.31 |
| 5,858,326 A | 1/1999 | Kisilevsky et al. | |
| 5,869,469 A | 2/1999 | Szarek et al. | |
| 5,972,328 A * | 10/1999 | Kisilevsky et al. | ........ 424/78.31 |
| 5,989,592 A | 11/1999 | Collin | |
| 6,015,835 A | 1/2000 | Miyamoto et al. | |
| 6,294,583 B1 | 9/2001 | Fogel | |
| 6,306,909 B1 | 10/2001 | Weaver et al. | |
| 6,310,073 B1 | 10/2001 | Kisilevsky et al. | |
| 6,316,501 B1 | 11/2001 | Miyamoto et al. | |
| 6,329,356 B1 | 12/2001 | Szarek et al. | |
| 6,376,557 B1 | 4/2002 | Zaveri | |
| 6,440,952 B2 | 8/2002 | Szarek et al. | |
| 6,562,836 B1 | 5/2003 | Szarek et al. | |
| 6,670,399 B2 * | 12/2003 | Green et al. | ................... 514/578 |
| 6,746,678 B1 | 6/2004 | Shapiro | |
| 6,930,112 B2 | 8/2005 | Weaver et al. | |
| 7,244,764 B2 | 7/2007 | Kong et al. | |
| 7,253,306 B2 | 8/2007 | Kong et al. | |
| 7,262,223 B2 | 8/2007 | Kong et al. | |
| 2001/0048941 A1 | 12/2001 | Kisilevsky et al. | |
| 2002/0022657 A1 | 2/2002 | Gervais et al. | |
| 2002/0115717 A1 | 8/2002 | Gervais et al. | |
| 2002/0151506 A1 * | 10/2002 | Castillo et al. | ................... 514/27 |
| 2002/0193395 A1 | 12/2002 | Kisilevsky et al. | |
| 2003/0027796 A1 | 2/2003 | Szarek et al. | |
| 2003/0077833 A1 | 4/2003 | Campbell et al. | |
| 2003/0108595 A1 | 6/2003 | Kisilevsky et al. | |
| 2003/0114441 A1 | 6/2003 | Weaver et al. | |
| 2003/0147882 A1 * | 8/2003 | Solomon et al. | ............ 424/132.1 |
| 2003/0153584 A1 | 8/2003 | Weaver et al. | |
| 2003/0194375 A1 | 10/2003 | Weaver et al. | |
| 2003/0229144 A1 | 12/2003 | Weaver et al. | |
| 2004/0006092 A1 | 1/2004 | Chalifour et al. | |
| 2004/0086562 A1 * | 5/2004 | Shanghvi et al. | .............. 424/468 |
| 2004/0096453 A1 | 5/2004 | Kisilevsky et al. | |
| 2004/0138178 A1 | 7/2004 | Szarek et al. | |
| 2004/0208875 A1 * | 10/2004 | Kisilevsky et al. | ........ 424/145.1 |
| 2004/0220138 A1 | 11/2004 | Gervais et al. | |
| 2004/0248876 A1 | 12/2004 | Szarek et al. | |
| 2005/0031651 A1 | 2/2005 | Gervais et al. | |
| 2005/0038000 A1 | 2/2005 | Kong et al. | |
| 2005/0048000 A1 | 3/2005 | Gervais et al. | |
| 2005/0096385 A1 | 5/2005 | Kong et al. | |
| 2005/0142191 A1 | 6/2005 | Legore | |
| 2005/0143462 A1 | 6/2005 | Kong et al. | |

(Continued)

FOREIGN PATENT DOCUMENTS

DE  4004978 A1  8/1991

(Continued)

OTHER PUBLICATIONS

Kergueris MF, Milpied N, Moreau P, Harousseau JL, Larousse C., Pharmacokinetics of high-dose melphalan in adults: influence of renal function. Anticancer Res. Nov.-Dec. 1994;14(6A):2379-82.*

(Continued)

*Primary Examiner* — Marcos Sznaidman

(74) *Attorney, Agent, or Firm* — Stephen E. Reiter; Foley & Lardner LLP

(57) ABSTRACT

Methods, formulations, and compositions for the treatment of amyloidosis are described.

9 Claims, 4 Drawing Sheets

U.S. PATENT DOCUMENTS

| | | | |
|---|---|---|---|
| 2005/0215562 | A1 | 9/2005 | Tremblay |
| 2006/0008917 | A1 | 1/2006 | Campbell et al. |
| 2006/0014752 | A1 | 1/2006 | Weaver et al. |
| 2006/0116347 | A1 | 6/2006 | Kisilevsky et al. |
| 2006/0135479 | A1 | 6/2006 | Szarek et al. |
| 2006/0167057 | A1 | 7/2006 | Kong et al. |
| 2006/0167095 | A1 | 7/2006 | Kisilevsky et al. |
| 2006/0183800 | A1 | 8/2006 | Kong et al. |
| 2006/0223855 | A1 | 10/2006 | Kong et al. |
| 2007/0010573 | A1 | 1/2007 | Kong et al. |
| 2007/0015737 | A1 | 1/2007 | Clark et al. |
| 2007/0021483 | A1 | 1/2007 | Chalifour et al. |
| 2007/0078082 | A1 | 4/2007 | Kisilevsky et al. |
| 2008/0038192 | A1* | 2/2008 | Gervais .................. 424/1.49 |

FOREIGN PATENT DOCUMENTS

| | | | |
|---|---|---|---|
| EP | 0119274 B1 | 9/1984 | |
| EP | 0293974 B1 | 12/1988 | |
| EP | 0309421 B1 | 3/1989 | |
| EP | 0323416 | 7/1989 | |
| EP | 0330353 B1 | 8/1989 | |
| EP | 0405834 A2 | 1/1991 | |
| EP | 0457295 B1 | 11/1991 | |
| EP | 0464759 A2 | 1/1992 | |
| EP | 0533352 A2 | 3/1993 | |
| EP | 0387867 B1 | 5/1993 | |
| EP | 0797992 A2 | 10/1997 | |
| EP | 1060750 B1 | 12/2000 | |
| FR | 2437834 | 6/1980 | |
| JP | 1-151514 | 6/1989 | |
| JP | 1-171638 | 7/1989 | |
| JP | 2-78620 A | 3/1990 | |
| JP | 2-149341 A | 6/1990 | |
| JP | 3-83921 A | 4/1991 | |
| JP | 4-13603 | 1/1992 | |
| JP | 5-17471 A | 1/1993 | |
| WO | WO-88/09171 A1 | 12/1988 | |
| WO | WO-89/05646 | 6/1989 | |
| WO | WO-89/05646 A1 | 6/1989 | |
| WO | WO-90/09789 A2 | 9/1990 | |
| WO | WO-92/02248 A1 | 2/1992 | |
| WO | WO-92/14456 A1 | 9/1992 | |
| WO | WO-93/10459 A1 | 5/1993 | |
| WO | WO-93/11762 A1 | 6/1993 | |
| WO | WO-93/24118 A1 | 12/1993 | |
| WO | WO-94/00135 A1 | 1/1994 | |
| WO | WO-94/01116 A1 | 1/1994 | |
| WO | WO-94/22437 A2 | 10/1994 | |
| WO | WO-95/01096 A1 | 1/1995 | |
| WO | WO-96/04195 A1 | 2/1996 | |
| WO | WO-96/28187 A1 | 9/1996 | |
| WO | WO-96/39129 A1 | 12/1996 | |
| WO | WO-97/09445 A1 | 3/1997 | |
| WO | WO-99/40909 A1 | 8/1999 | |
| WO | WO-00/27807 A1 | 5/2000 | |
| WO | WO-00/69444 A1 | 11/2000 | |
| WO | WO-01/85093 A2 | 11/2001 | |
| WO | WO-2004/058239 A1 | 7/2004 | |
| WO | WO 2004/113391 | * 12/2004 | |
| WO | WO-2004/113391 A2 | 12/2004 | |
| WO | WO-2006/008661 A2 | 1/2006 | |

OTHER PUBLICATIONS

Shinsuke Nomura, Takuro Matsutani, Tom Shindo, Ken-Ichi Klmura, Gengo Osawa and Kazushi Kozuka, Amyloidosis (AA type) with Gastrointestinil Involvement: Resolution of Gastric Amyloid Deposition in Parallel with Disappearance of the Serum Componentof Amyloid A Protein Jpn J Med vol. 29, No. 2 (Mar., Apr. 1990).*

Booth DR, Gillmore JD, Lachmann HJ, Booth SE, Bybee A, Soytürk M, Akar S, Pepys MB, Tunca M, Hawkins PN. The genetic basis of autosomal dominant familial Mediterranean fever. QJM. Apr. 2000;93(4):217-21.*

Sezer et. al., Expert Opinion on Investigational Drugs (2000) 9:2343-2350.*

Sezer et. al. (Expert Opinion on Investigational Drugs (2000) 9:2343-2350).*

Gervais, Francine et al., "Proteoglycans and Amyloidogenic Proteins in Peripheral Amyloidosis," *Curr. Med. Chem.*, vol. 3:361-370 (2003).

Kisilevsky, Robert et al., "Arresting amyloidosis in vivo using small-molecule anionic sulphonates or sulphates: implications for Alzheimer's disease," *Nature Medicine*, vol. 1(2):143-148 (1995).

Kisilevsky, Robert et al., "Short-Chain Aliphatic Polysulfonates Inhibit the Entry of Plasmodium into Red Blood Cells," *Antimicrobial Agents and Chemotherapy*, vol. 46(8):2619-2626 (2002).

Ono, Kenjiro et al., "Nordihydroguaiaretic acid potently breaks down pre-formed Alzheimer's β-amyloid fibrils in vitro," *Journal of Neurochemistry*, vol. 81:434-440 (2002).

Revill, P. et al., "Eprodisate Sodium," *Drugs of the Future*, vol. 31(7):576-578 (2006).

International Search Report for Application No. PCT/IB2006/002540, dated May 16, 2007.

Axelrad, M.A. et al, "Further Characterization of Amyloid-Enhancing Factor," *Laboratory Investigation*, vol. 47(2):139-146 (1982).

Brissette, Louise et al, "Differential Induction of the Serum Amyloid a Gene Family in Response to an Inflammatory Agent and to Amyloid-enhancing Factor," *The Journal of Biological Chemistry*, vol. 264(32):19327-19332 (1989).

Buée, L. et al, "Alzheimer's disease: binding of vascular and neuroblastoma heparan sulfate proteoglycans to amyloid β protein A4," *Advances in the Biosciences*, vol. 87:217-218 (1993).

Caughey, Bryon et al, "Binding of the Protease-Sensitive Form of Prion Protein PrP to Sulfated Glycosaminoglycan and Congo Red," *Journal of Virology*, vol. 68(4):2135-2141 (1994).

Caughey, B., "Protease-resistant PrP accumulation and scrapie agent replication: a role for sulphated glycosaminoglycans?" *Biochemical Society Transactions, 648th Meeting Belfast*, vol. 22:163-167 (1994).

Caughey, Byron, "Scrapie-associated PrP accumulation and agent replication: effects on sulphated glycosaminoglycan analogues," *Phil. Trans. R. Soc. Lond. B.*, vol. 343:399-404 (1994).

Caughey, B., "Scrapie associated PrP accumulation and its prevention: insights from cell culture," *British Medical Bulletin*, vol. 49(4):860-872 (1993).

Caughey, Byron et al, "Sulfated Polyanion Inhibition of Scrapie-Associated PrP Accumulation in Cultured Cells," *Journal of Virology*, vol. 67(2):643-650 (1993).

Colon, Wilfredo et al, "Partial Denaturation of Transthyretin is Sufficient for Amyloid Fibril Formation in Vitro," *Biochemistry*, vol. 31:8654-8660 (1992).

Dow, Kimberly E. et al, "Effects of 4-deoxy-L-*threo*-pentose, a novel carbohydrate, on neural cell proteoglycan synthesis and function," *Biochimica et Biophysica Acta*, vol. 1156:7-14 (1992).

Ehlers, Bernhard et al, "Dextran Sulphate 500 Delays and Prevents Mouse Scrapie by Impairment of Agent Replication in Spleen," *The Journal of General Virology*, vol. 65:1325-1330 (1984).

Fraser, Paul E. et al, "Effects of Sulfate Ions on Alzheimer β/A4 Peptide Assemblies: Implications for Amyloid Fibril-Proteoglycan Interactions," *Journal of Neurochemistry*, vol. 59:1531-1540(1992).

Garceau, Denis et al., "A prospective analysis of demography, etiology, and clinical findings of AA amyloidosis patients enrolled in the international clinical phase II/III Fibrillex™ study," Slideshow, On behalf of the Fibrillex™ Amyloidosis Secondary Trial (FAST) Group (2004).

Garceau, David et al., "Safety, Tolerability and Pharmacokinetic Profile of Fibrillex™ (Anti-AA Amyloid Agent) in Healthy and Renal Impaired Subjects," *Amyloid and Amyloidosis, The Proceedings of the IXth International Symposium on Amyloidosis*, 3.1.5 Poster and Oral Presentation (2001).

Garceau, Denis et al., "Safety, Tolerability and Pharmacokinetic Profile of Fibrillex™ (Anti-AA Amyloid Agent) in Healthy and Renal Impaired Subjects," *Amyloid, The Journal of Protein Folding Disorders*, Abstracts of the IXth International Symposium on Amyloidosis, vol. 8(Suppl. 2):39, Poster No. 3.1.5 (2001).

Gervais, Francine, "Amyloid—Those Deadly Fibrils," *Eur. Biopharm. Review*, pp. 40-42 (2001).

Hamazaki, Hideaki, "$Ca^{2+}$-mediated Association of Human Serum Amyloid P Component with Heparan Sulfate and Dermatan Sulfate," *The Journal of Biological Chemistry*, vol. 262(4):1456-1460 (1987).

Hamazaki, Hideaki et al, "Calcium-dependent polymerization of human serum amyloid P component is inhibited by heparin and dextran sulfate," *Biochimica et Biophysica Acta*, vol. 998:231-235 (1989).

Hauck, W. et al., "A Prospective Analysis of Demography, Etiology, and Clinical Findings of AA Amyloidosis Patients Enrolled in the International Clinical Phase II/III Fibrillex™ Study," *Amyloid and Amyloidosis*, pp. 179-180 (2005).

Hazenberg, B.P.C. et al., "Diagnostic and therapeutic approach of systemic amyloidosis," *Neth. J. Med.*, vol. 62:121-128 (2004).

Hirschfield, G.M. et al., "Amyloidosis: new strategies for treatment," *The International Journal of Biochemistry & Cell Biology*, vol. 35:1608-1613 (2003).

Kagan, D.Z. et al, "Congo Red Inhibition of Amylogenesis in Experimental Amyloidosis," *Problemy Tuberkuleza*, vol. 40:72-74.

Kisilevsky, Robert, "A Critical Analysis of Postulated Pathogenetic Mechanisms in Amyloidogenesis," *Critical Reviews in Clinical Laboratory Sciences*, vol. 29(1):59-82 (1992).

Kisilevsky, R., "From arthritis to Alzheimer's disease: current concepts on the pathogenesis of amyloidosis," *Can. J. Physiol. Pharmacol.*, vol. 65:1805-1815 (1987).

Kisilevsky, Robert, "Heparan Sulfate Proteoglycans in Amyloidogenesis: An Epiphenomenon, A Unique Factor, or the Tip of a More Fundamental Process?" *Laboratory Investigation*, vol. 63(5):589-591 (1990).

Kisilevsky, R. et al, "The Potential Significance of Sulphated Glycosaminoglycans as a Common Constituent of all Amyloids: or, Perhaps Amyloid is not a Misnomer," *Medical Hypotheses*, vol. 26:231-236 (1988).

Kisilevsky, Robert, "Theme and Variations on a String of Amyloid," *Neurobiology of Aging*, vol. 10:499-500 (1989).

Krogsgaard-Larsen, P. et al, "Novel (Gamma-Aminobutyric Acid)$_A$ Agonists and Partial Agonists," *FIDIA Research Foundation Symposium Series* (1991).

Leveugle, B. et al, "Binding of heparan sulfate glycosaminoglycan to β-amyloid peptide: inhibition by potentially therapeutic polysulfated compounds," *NeuroReport*, vol. 5:1389-1392 (1994).

Lyon, A.W. et al, "Co-deposition of Basement Membrane Components during the Induction of Murine Splenic AA Amyloid," *Laboratory Investigation*, vol. 64(61785-790 (1991).

McCubbin, William D. et al, "Circular-dichroism studies on two murine serum amyloid A proteins," *Biochem. J.*, vol. 256:775-783 (1988).

Miyazawa, Keisuke et al., "Occurrence of d-2-Hydroxy-3-aminopropane Sulfonic Acid and 3-Aminopropane Sulfonic Acid in a Red Alga *Grateloupia livida*," *Bulletin of the Japanese Society of Scientific Fisheries*, vol. 36(1):109-114 (1970).

Nakada, Tsutomu et al, "Guanidinoethane sulfate: brain pH alkaline shifter," *NeuroReport*, vol. 4:1035-1038 (1993).

Narindrasorasak, Suree et al, "Characterization of High Affinity Binding between Laminin and Alzheimer's Disease Amyloid Precursor Proteins," *Laboratory Investigation*, vol. 67(5):643-652 (1992).

Narindrasorasak, Suree et al, "High Affinity Interactions between the Alzheimer's β-Amyloid Precursor Proteins and the Basement Membrane Form of Heparan Sulfate Proteoglycan," *The Journal of Biological Chemistry*, vol. 266(20):12878-12883 (1991).

Neurochem announces completion of Phase II/III clinical trial for Fibrillex™, Neurochem Press Release Dec. 7, 2004.

Neurochem Inc. announces the signing of exclusive collaboration and distribution agreement for Fibrillex™ with Centocor, Inc., Neurochem Press Release Dec. 22, 2004.

Neurochem unblinds the Phase II/III Clinical Study for Fibrillex™ in the treatment of AA Amyloidosis, Neurochem Press Release Apr. 8, 2005.

Pollack, Scott J. et al, "Sulfonated dyes attenuate the toxic effects of β-amyloid in a structure-specific fashion," *Neuroscience Letters*, vol. 197:211-214 (1995).

Puchtler, H. et al, "Application of Thiazole Dyes to Amyloid under Conditions of Direct Cotton Dyeing: Correlation of Histochemical and Chemical Data," *Histochemistry*, vol. 77:431-445 (1983).

Sadler, Isobel I. J. et al, "Sulphated compounds attenuate β-amyloid toxicity by inhibiting its association with cells," *NeuroReport*, vol. 7:49-53 (1995).

Shue, Ho-Jane et al, "A Study of 3-Amino-N-Hydroxypropanesulfonamide Derivatives as Potential GABA$_B$ Agonists and Their Fragmentation to 3-Aminopropanesulfinic Acid," *Bioorganic & Medicinal Chemistry Letters*, vol. 6(14):1709-1714 (1996).

Small, D.H. et al, "Association and Release of the Amyloid Protein Precursor of Alzheimer's Disease from Chick Brain Extracellular Matrix," *The Journal of Neuroscience*, vol. 12(11):4143-4150 (1992).

Snow, Alan David et al, "A Close Ultrastructural Relationship between Sulfated Proteoglycans and AA Amyloid Fibrils," *Laboratory Investigation*, vol. 57(6):687-698 (1987).

Snow, Alan D. et al, "A Temporal and Ultrastructural Relationship Between Heparan Sulfate Proteoglycans and AA Amyloid in Experimental Amyloidosis," *The Journal of Histochemistry and Cytochemistry*, vol. 39(10):1321-1330 (1991).

Snow, Alan David et al, "Characterization of Tissue and Plasma Glycosaminoglycans during Experimental AA Amyloidosis and Acute Inflammation, Qualitative and Quantitative Analysis," *Laboratory Investigation*, vol. 56(6):665-675 (1987).

Snow, Alan D. et al, "Sulfated Glycosaminoglycans in Alzheimer's Disease," *Human Pathology*, vol. 18(5):506-510 (1987).

Snow, Alan D. et al, "Sulfated Glycosaminoglycans: A Common Constituent of All Amyloids?" *Laboratory Investigation*, vol. 56(1):120-123 (1987).

Snow, A. D. et al, "Sulfated glycosaminoglycans in amyloid plaques of prion diseases," *Acta Neuropathol.*, vol. 77:337-342 (1989).

Snow, Alan D. et al, "Temporal Relationship between Glycosaminoglycan Accumulation and Amyloid Deposition during Experimental Amyloidosis," *Laboratory Investigation*, vol. 53(1):3744 (1985).

Tape, C. et al, "Direct Evidence for Circulating apoSAA as the Precursor of Tissue AA Amyloid Deposits," *Scand. J. Immunol.*, vol. 28:317-324 (1988).

The Merck Index, p. 883, Merck & Co. Inc., Rahway, N.J., USA (1989).

Travis, John, "New Piece of Alzheimer's Puzzle," *Science*, vol. 261:828-829 (1993).

Tsuchiya, Teruo et al., "Antidotes for Paraquat Poisonings X: The Effect of Sulfonates and Sulfates on Absorption of Paraquat from Intestine," *Jpn. J. Forensic. Toxicol.*, vol. 9:130-131 (1991).

Wong, S. et al, "Influence of Sulphate Ions on the Structure of AA Amyloid Fibrils," *Scand. J. Immunol.*, vol. 32:225-232 (1990).

Wood, Stephen J. et al, "Selective Inhibition of Aβ Fibril Formation," *The Journal of Biological Chemistry*, vol. 271(8):4086-4092 (1996).

Young, Iain D. et al, "Localization of the Basement Membrane Heparan Sulfate Proteoglycan in Islet Amyloid Deposits in Type II Diabetes Mellitus," *Arch Pathol Lab Med.*, vol. 116:951-954 (1992).

Young, I.D. et al, "The ultrastructural localization of sulfated proteoglycans is identical in the amyloids of Alzheimer's disease and AA, AL, senile cardiac and medullary carcinoma-associated amyloidosis,"*Acta Neuropathol.*, vol. 78:202-209 (1989).

Abstract and Poster of oral presentation of IXth International Symposium on Amyloid and Amyloidosis, Budapest, Jul. 15-21, 2001, by Garceau et al entitled, "Safety, Tolerability and Pharmacokinetic Profile of Fibrillex™ (Anti-AA Amyloid Agent) in Healthy and Renal Impaired Subjects."

Preliminary Program for Xth International Symposium on Amyloid and Amyloidosis, Loire Valley, Apr. 18-22, 2004, with Abstract and slides for "A prospective analysis of demography, etiology, and clinical findings of AA anyloidosis patients enrolled in the international clinical Phase II/III Fibrillex™ study," by Garceau et al.

Merck Manual; Amyloidosis: Endocrine and Metabolic Disorders, http://www.merck.com/mmpe/sec12/ch160/ch160a.html, 3 pages.

Satoskar, A. A., et al., "Typing of Amyloidosis in Renal Biopsies—Diagnostic Pitfalls,"Arch. Pathol. Lab. Med., vol. 131, Jun. 2007, pp. 917-922.

International Preliminary Report on Patentability dated Oct. 16, 2007 in application PCT/IB2006/002540.

Search Report dated Jul. 7, 2008 in EP application 06795492.

Search Report dated Aug. 13, 2010 in EP application 06795492.

\* cited by examiner

FORMULATIONS AND METHODS FOR TREATING AMYLOIDOSIS

RELATED APPLICATIONS

This application claims priority to U.S. Provisional Patent Application Ser. No. 60/671,866, filed on Apr. 15, 2005, the entire contents of which are hereby incorporated herein by reference.

The data presented was financially supported by the US government (Food and Drug Administration, Department of Health & Human Services, reference number FD-R-002007)

BACKGROUND OF THE INVENTION

Amyloidosis is the generic term for a number of diseases related by extracellular deposition of insoluble fibrillar proteins (amyloid) in specific organs, which eventually leads to the failure of the involved organs. R. H. Falk et al., *The Systemic Amyloidosis,* 337 N ENGL J MED 898-909 (1997), P. N. Hawkins, *Amyloidosis,* 9 BLOOD REV 13542 (1995), J. D. Sipe, *Amyloidosis,* 31 CR REV CLIN LAB SCI 325-54 (1994); A. S. Cohen, *Amyloidosis,* 40(2) BULL RHEUM DISEASES 1-12 (1991). Amyloid deposits can remain limited to one organ (localized amyloidosis) or may be more broadly distributed (systemic amyloidosis). Systemic amyloidoses are generally classified into four types based on the nature of the fibrillar deposits: (i.) idiopathic or primary amyloidosis (AL amyloidosis); (ii.) reactive, secondary or amyloid A (AA) amyloidosis; (iii.) familial amyloidotic polyneuropathy; and (iv.) dialysis-associated amyloidosis. Though diverse in their occurrence, all amyloid deposits have common morphologic properties, stain with specific dyes (e.g., Congo red), and have a characteristic birefringent appearance in polarized light after staining. They also share common ultrastructural features and common X-ray diffraction and infrared spectra.

AA amyloidosis is thought to be related to amyloid A (AA) protein formed from the precursor serum amyloid A (SAA), an acute phase protein produced and secreted by hepatocytes in response to inflammation. AA amyloidosis is associated with chronic inflammatory conditions (e.g., rheumatoid arthritis, ankylosing spondylitis, inflammatory bowel disease, etc.), chronic infections (e.g., tuberculosis, osteomyelitis etc.), and hereditary fevers, e.g., Familial Mediterranean Fever (R. H. Falk et al., 337 N ENGL J MED 898-909 (1997), A. S. Cohen, 40(2) BULL RHEUM DISEASES 1-12 (1991), G. Grateau, 12 CURRENT OPINION IN RHEUMATOL 61-64 (2000)). Rheumatoid arthritis is the major cause of AA amyloidosis in Western Europe and North America (M. Skinner *Amyloidosis,* CURRENT THERAPY IN ALLERGY, IMMUNOLOGY, AND RHEUMATOLOGY 235-40 (Mosby-Year Book Inc., 1996), M. A. Gertz, *Secondary amyloidosis,* 232 J INT MED 517-18 (1992)).

AA amyloidosis mainly affects parenchymatous organs, such as, kidneys, spleen, liver, and adrenals. The most common clinical feature of AA amyloidosis is renal dysfunction manifested as nephrotic-range proteinuria or renal insufficiency at the time of diagnosis. End-stage renal failure is the cause of death in 40-60% of cases (M. Skinner *Amyloidosis,* CURRENT THERAPY IN ALLERGY, IMMUNOLOGY, AND RHEUMATOLOGY 235-40 (Mosby-Year Book Inc., 1996), M. A. Gertz, 232 J INT MED 517-18 (1992), M. A. Gertz and R. A. Kyle, 70 MEDICINE 246-256 (1991)). Gastrointestinal involvement is also frequent and is usually manifested as chronic diarrhea, body weight loss and malabsorption. Enlargement of the liver and spleen may also occur in some subjects. Cardiac involvement is rare and occurs late in the disease. The median survival time from diagnosis varies from 2 to 8 years depending on the stage of the disease at time of diagnosis (M. A. Gertz and R. A. Kyle, 70 MEDICINE 246-256 (1991)).

AA amyloidosis is usually seen associated with chronic infection (such as tuberculosis) or chronic inflammation (such as rheumatoid arthritis or hereditary fevers). A familial form of AA amyloidosis is seen Familial Mediterranean Fever (FMF). This familial type of amyloidosis is genetically inherited and is found in specific population groups. In both AL and AA amyloidosis, deposits are found in several organs and are thus considered systemic amyloid diseases.

"Localized amyloidoses" are those that tend to involve a single organ system. Different amyloids are also characterized by the type of protein present in the deposit. For example, neurodegenerative diseases such as scrapie, bovine spongiform encephalitis, Creutzfeldt-Jakob disease, and the like are characterized by the appearance and accumulation of a protease-resistant form of a prion protein (referred to as AScr or PrP-27) in the central nervous system. Similarly, Alzheimer's disease, another neurodegenerative disorder, is characterized by neuritic plaques and neurofibrillary tangles. In this case, the amyloid plaques found in the parenchyma and the blood vessel is formed by the deposition of fibrillar Aβ amyloid protein. Other diseases such as adult-onset diabetes (type II diabetes) are characterized by the localized accumulation of amyloid fibrils in the pancreas.

Once these amyloids have formed, there is no known, widely accepted therapy or treatment which significantly dissolves amyloid deposits in situ, prevents further amyloid deposition or prevents the initiation of amyloid deposition.

Each amyloidogenic protein has the ability to undergo a conformational change and to organize into β-sheets and form insoluble fibrils which may be deposited extracellularly or intracellularly. Each amyloidogenic protein, although different in amino acid sequence, has the same property of forming fibrils and binding to other elements such as proteoglycan, amyloid P and complement component. Moreover, each amyloidogenic protein has amino acid sequences which, although different, show similarities such as regions with the ability to bind to the glycosaminoglycan (GAG) portion of proteoglycan (referred to as the GAG binding site) as well as other regions which promote β-sheet formation. Proteoglycans are macromolecules of various sizes and structures that are distributed almost everywhere in the body. They can be found in the intracellular compartment, on the surface of cells, and as part of the extracellular matrix. The basic structure of all proteoglycans is comprised of a core protein and at least one, but frequently more, polysaccharide chains (GAGs) attached to the core protein. Many different GAGs have been discovered including chondroitin sulfate, dermatan sulfate, keratan sulfate, heparin, and hyaluronan.

Some GAG mimetics are known to be useful for inhibiting amyloid deposition and/or treating some forms of amyloidosis. See WO 94/22437, WO 96/28187, and WO 00/64420.

SUMMARY OF THE INVENTION

In one embodiment, the invention pertains to a method of treating or preventing AA amyloidosis in a target subject, by administering to the target subject a therapeutically effective amount of a compound of the formula:

$$Y-(CH_2)_n-[CH_2Y]_m \qquad (I)$$

wherein Y is $SO_3X$ or $OSO_3X$ independently chosen for each occurrence; X is cationic group independently chosen for each occurrence; n is 1, 2, 3 or 4; and m is 1 or 2, such that the AA amyloidosis is treated or prevented, while maintaining an acceptable tolerance index (ATI) for a parameter associated with renal impairment (PRI). Furthermore, in this embodiment, the target subject is being treated for AA amyloidosis and has or is susceptible to a parameter associated with renal impairment. In a further embodiment the compound of formula (I) is 1,3-propanedisulfonic acid or a pharmaceutically acceptable salt thereof, e.g. a disodium salt.

In another embodiment, the invention includes a method of treating or preventing AA amyloidosis in a target subject, by administering to the target subject a therapeutically effective amount of a compound of formula (I), e.g., 1,3-propanedisulfonic acid or a pharmaceutically acceptable salt thereof, e.g. a disodium salt, such that the AA amyloidosis is treated or prevented while maintaining an acceptable tolerance index (ATI) for a parameter associated with gastrointestinal impairment (PGI). Furthermore, in this embodiment, the target subject is being treated for AA amyloidosis and has or is susceptible to a parameter associated with gastrointestinal impairment.

In another further embodiment, the invention also pertains to a method of treating or preventing an amyloid related disease in a subject by administering to a subject in need thereof, a therapeutically effective amount of a compound of formula (I), e.g., 1,3-propanedisulfonic acid or a pharmaceutically acceptable salt thereof, e.g. a disodium salt, at a dosage selected based upon creatinine clearance rate, such that the amyloid related disease is treated or prevented.

The invention also pertains, at least in part, to a method for treating or preventing AA amyloidosis in a subject, by administering to the subject in need thereof, a therapeutically effective amount of a compound of formula (I), e.g., 1,3-propanedisulfonic acid or a pharmaceutically acceptable salt thereof, e.g. a disodium salt, which is administered in a dosage, such that an effective exposure is provided in a subject, for example, as measured by, e.g., AUC, $C_{max}$, $AUC_{ss}$, $C_{ss}$, $T_{max}$, etc.

In addition, the invention also pertains to a method of stabilizing or improving renal and/or gastrointestinal function in a subject. The method includes administering to a subject a therapeutically effective amount of a compound of formula (I), e.g., 1,3-propanedisulfonic acid or a pharmaceutically acceptable salt thereof, e.g. a disodium salt.

In another embodiment, the invention pertains to a method of treating or preventing AA amyloidosis in a subject. The method includes administering to a subject in need thereof, a therapeutically effective amount of a compound of formula (I), e.g., 1,3-propanedisulfonic acid or a pharmaceutically acceptable salt thereof, e.g. a disodium salt, in combination with a second agent such that AA amyloidosis is treated or prevented.

In yet another embodiment, the invention pertains, at least in part, to a method of increasing the oral bioavailability of a compound in a subject, by administering to a subject a therapeutically effective amount of the compound of formula (I), e.g., 1,3-propanedisulfonic acid or a pharmaceutically acceptable salt thereof, e.g. a disodium salt, in a pharmaceutical composition without food such that the oral bioavailability of the compound in the subject is increased.

The invention also pertains, at least in part, to a method of treating an inflammatory disease in a subject, by administering to a subject in need thereof, a therapeutically effective amount of a compound of formula (I), e.g., 1,3-propanedisulfonic acid or a pharmaceutically acceptable salt thereof, e.g. a disodium salt, in combination with a second agent such that said inflammatory disease is treated in the subject.

The invention also pertains, at least in part, to a method of treating a hereditary fever in a subject, by administering to a subject in need thereof, a therapeutically effective amount of a compound of formula (I), e.g., 1,3-propanedisulfonic acid or a pharmaceutically acceptable salt thereof, e.g. a disodium salt, in combination with a second agent such that said hereditary fever is treated in the subject.

The invention also pertains, at least in part, to a method for treating rheumatoid arthritis in a subject. The method includes administering to a subject a therapeutically effective amount of a compound of formula (I), e.g., 1,3-propanedisulfonic acid or a pharmaceutically acceptable salt thereof, e.g. a disodium salt, in combination with a second agent.

In addition, the invention also includes a method of treating a malignant neoplasm in a subject. The method includes administering to a subject in need thereof, a therapeutically effective amount of a compound of formula (I), e.g., 1,3-propanedisulfonic acid or a pharmaceutically acceptable salt thereof, e.g. a disodium salt, in combination with a second agent such that the malignant neoplasm is treated in the subject.

In a further embodiment, the invention pertains, at least in part, to a method of treating a chronic infection, e.g., microbial or viral, in a subject. The method includes administering to a subject in need thereof, a therapeutically effective amount of a compound of formula (I), e.g., 1,3-propanedisulfonic acid or a pharmaceutically acceptable salt thereof, e.g. a disodium salt, in combination with a second agent such that the chronic infection is treated in the subject.

In another further embodiment, the invention pertains at least in part to method of stabilizing or improving renal function or delaying progression of renal disease in a subject having an inflammatory disorder, a malignant neoplasm, a chronic infection or a hereditary fever. The method includes administering to the subject a therapeutically effective amount of 1,3-propanedisulfonic acid or a pharmaceutically acceptable salt thereof, such that renal function is stablized or improved or progression of renal disease is delayed.

In another embodiment, the invention pertains, at least in part, to a method for preventing or delaying progression to ESRD/dialysis in a subject having AA amyloidosis. The method includes administering to the subject, e.g., a subject having AA amyloidosis, a therapeutically effective amount of a compound of formula (I), e.g., 1,3-propanedisulfonic acid or a pharmaceutically acceptable salt thereof, e.g. a disodium salt, such that progression to ESRD/dialysis is delayed or prevented.

In another embodiment, the invention pertains, at least in part, to a method for preventing or delaying the time to the doubling of serum creatinine in a subject having AA amyloidosis. The method includes administering to the subject a therapeutically effective amount of a compound of formula (I), e.g.,1,3-propanedisulfonic acid or a pharmaceutically acceptable salt thereof, e.g. a disodium salt, such that the time to the doubling of serum creatinine is delayed or prevented.

In yet another embodiment, the invention pertains, at least in part, to a method for preventing or delaying the time to at least a 50% decrease in creatinine clearance in a subject having AA amyloidosis. The method includes administering to a subject a therapeutically effective amount of a compound of formula (I), e.g., 1,3-propanedisulfonic acid or a pharmaceutically acceptable salt thereof, e.g. a disodium salt, such that the time to the at least a 50% decrease in creatinine clearance is delayed or prevented.

In another embodiment, the invention pertains, at least in part, to a method for decreasing the time to at least a 50% increase in creatinine clearance in a subject having AA amyloidosis. The method includes administering to the subject a therapeutically effective amount of a compound of formula (I), e.g., 1,3-propanedisulfonic acid or a pharmaceutically acceptable salt thereof, e.g. a disodium salt, such that the time to the at least 50% increase in creatinine clearance is decreased.

In yet another embodiment, the invention includes a method for reducing the rate of progression of renal disease as measured by the slope of creatinine clearance in a subject having AA amyloidosis. The method includes administering to the subject a therapeutically effective amount of a compound of formula (I), e.g., 1,3-propanedisulfonic acid or a pharmaceutically acceptable salt thereof, e.g. a disodium salt, such that the rate of progression of renal disease is reduced.

In another embodiment, the invention pertains, at least in part, to a method for stabilizing or reducing proteinuria in a subject having AA amyloidosis. The method includes administering to the subject a therapeutically effective amount of a compound of formula (I), e.g., 1,3-propanedisulfonic acid or a pharmaceutically acceptable salt thereof, e.g. a disodium salt, such that the proteinuria in said subject is stabilized or reduced.

In yet another embodiment, the invention includes a method for stabilizing renal function or delaying progression of renal disease in a subject having AA amyloidosis. The method includes administering to the subject a therapeutically effective amount of a compound of formula (I), e.g., 1,3-propanedisulfonic acid or a pharmaceutically acceptable salt thereof, e.g. a disodium salt, such that renal function is stabilized or progression of renal disease is delayed. In one aspect, progression of renal disease may be measured by a 50% decrease in creatinine clearance (CrCl), doubling of serum creatinine (SCr), and/or progression to ESRD.

In yet another further embodiment, the invention pertains, at least in part, to a method for treating renal impairment in a subject having AA amyloidosis. The method includes administering to the subject a therapeutically effective amount of a compound of formula (I), e.g., 1,3-propanedisulfonic acid or a pharmaceutically acceptable salt thereof, e.g. a disodium salt, such that the renal impairment is treated.

The invention also pertains, at least in part, to a pharmaceutical composition comprising a therapeutically effective amount of a compound of formula (I), e.g., 1,3-propanedisulfonic acid or a pharmaceutically acceptable salt thereof, e.g. a disodium salt, and a second agent.

In a further embodiment, the invention pertains to a packaged pharmaceutical composition. The packaged pharmaceutical composition includes a therapeutically effective amount of a compound of formula (I), e.g., 1,3-propanedisulfonic acid or a pharmaceutically acceptable salt thereof, e.g. a disodium salt, packaged in combination with a label or insert advising that the composition be administered in combination with a second agent.

In yet another further embodiment, the invention pertains to a packaged pharmaceutical composition, which includes a therapeutically effective amount of a second agent packaged in combination with a label or insert advising that the composition be administered in combination with a compound of formula (I), e.g., 1,3-propanedisulfonic acid or a pharmaceutically acceptable salt thereof, e.g. a disodium salt.

In yet another embodiment, the invention pertains to a packaged pharmaceutical composition, which includes a container holding a pharmaceutical composition comprising a therapeutically effective amount of a compound of formula (I), e.g., 1,3-propanedisulfonic acid or a pharmaceutically acceptable salt thereof, e.g. a disodium salt, in combination with a label or insert advising that the composition be administered without food.

In yet another embodiment, the invention pertains to a pharmaceutical formulation for treating AA amyloidosis. The formulation comprising a therapeutically effective amount of a compound of formula (I), e.g., 1,3-propanedisulfonic acid or a pharmaceutically acceptable salt thereof, e.g. a disodium salt, in a formulation, wherein the formulation has at least one favorable biological property (FBP) upon administration to the subject.

The invention also pertains, at least in part, to an anti-amyloidogenic agent in a formulation, wherein the anti-amyloidogenic agent-containing formulation is equivalent to a standard formulation predetermined to have at least one favorable biological property upon administration to a subject such that it is a biologically favorable formulation.

In another embodiment, the invention also includes a pharmaceutical formulation, which comprising a compound of formula (I), and one or more pharmaceutically acceptable carriers. In this embodiment, the pharmaceutical formulation, when administered once to a subject in need thereof, provides a $C_{max}$ of about 200 to about 2000 ng/mL.

In yet another embodiment, the invention also pertains to a pharmaceutical formulation, comprising a compound of formula (I), and one or more pharmaceutically acceptable carriers. In this embodiment, the pharmaceutical formulation, when administered to a subject in need thereof, provides an $AUC_\infty$ of about 2,000 to about 44,000 ng/mL.

The invention also pertains, at least in part, to a method of administering a compound to a subject in need thereof. The method includes administering a compound of formula (I) to the subject in an amount sufficient to achieve a $C_{max}$ of about 200 to about 3,400 ng/mL. The $C_{max}$ may occur about 0.25 to about 9.00 hours after administration.

In another embodiment, the invention also pertains, at least in part, to a method of administering a compound of formula (I) to a subject in need thereof. The method includes administering a compound of formula (I) to the subject in an amount sufficient to achieve an $AUC_\infty$ of about 2,000 to about 44,000 ng/mL.

In yet another embodiment, the invention pertains to a pharmaceutical formulation, which comprises a 1,3-propanedisulfonic acid or a pharmaceutically acceptable salt thereof and one or more pharmaceutically acceptable carriers. The pharmaceutical formulation provides a $C_{max}$ of about 200 to about 2000 ng/mL, when administered once to a subject in need thereof.

In yet another embodiment, the invention also includes a pharmaceutical formulation, which comprises 1,3-propanedisulfonic acid or a pharmaceutically acceptable salt thereof and one or more pharmaceutically acceptable carriers. The pharmaceutical formulation provides a $AUC_\infty$ of about 2,000 to about 44,000 ng/mL, when administered to a subject in need thereof.

In yet another embodiment, the invention also pertains to a method of administering 1,3-propanedisulfonic acid or a pharmaceutically acceptable salt thereof to a subject in need thereof. The method includes administering 1,3-propanedisulfonic acid or a pharmaceutically acceptable salt thereof to a subject in an amount sufficient to achieve a $C_{max}$ of about 200 to about 3,400 ng/mL about 0.25 to about 9.00 hours after administration.

In another embodiment, the invention also pertains to a method of administering 1,3-propanedisulfonic acid or a pharmaceutically acceptable salt thereof to a subject in need thereof, by administering 1,3-propanedisulfonic acid or a pharmaceutically acceptable salt thereof to the subject in an amount sufficient to achieve an $AUC_\infty$ of about 2,000 to about 44,000 ng/mL.

In yet another embodiment, the invention pertains, at least in part, to a pharmaceutical formulation. The pharmaceutical formulation comprises an active agent (e.g., 1,3-propanedisulfonic acid, disodium salt (also referred to as PDS) in an amount effective to treat or prevent AA amyloidosis, and a pharmaceutically acceptable carrier, wherein, when the formulation is orally administered to a healthy subject, a mean plasma concentration profile of the active agent having a mean $AUC_\infty$ of about from 2900 to about 9000 ng·h/mL±20% and a mean $C_{max}$ of about from 450 to about 2150 ng/mL±20% is achieved.

In yet another further embodiment, the invention also pertains, at least in part, to a pharmaceutical formulation, which comprises an active agent (e.g., PDS) in an amount effective to treat or prevent AA amyloidosis, and a pharmaceutically acceptable carrier, wherein, when the formulation is orally administered to a healthy subject, a mean plasma concentration profile of the active agent having a mean $AUC_\infty$ of from about 2,900 to about 9,000 ng·h/mL±20% is achieved.

In yet another further embodiment, the invention pertains to a pharmaceutical formulation, which comprises an active agent (e.g., PDS) in an amount effective to treat or prevent AA amyloidosis, and a pharmaceutically acceptable carrier, wherein, when the formulation is orally administered to a healthy subject, a mean plasma concentration profile of the active agent having a mean $C_{max}$ of about from 450 to about 2150 ng/mL±20% is achieved.

In yet another further embodiment, the invention pertains, at least in part, to a pharmaceutical formulation, comprising an active agent (e.g., PDS), and a pharmaceutically acceptable carrier, wherein, when the formulation is orally administered to a subject having AA amyloidosis: in a dose of 400 mg of the active agent to a subject having a creatinine clearance rate of less than about 30 ml/min, a mean plasma concentration profile of the active agent having a mean $AUC_\infty$ of about 10,000-12,000 ng·h/mL±20%, and a mean $C_{max}$ of about 800-900 ng/mL±20% is achieved; or in a dose of 800 mg of the active agent to a subject having a creatinine clearance rate of about 30 to about 80 mL/min, a mean plasma concentration profile of the active agent having a mean $AUC^\infty$ of about 9,000-10,500 ng·h/mL±20%, and a mean $C_{max}$ of about 750-875 ng/mL±20% is achieved; or in a dose of 1200 mg of the active agent to a subject having a creatinine clearance rate of greater than about 80 mL/min, a mean plasma concentration profile of the active agent having a mean $AUC_\infty$ of about 5,000-6,000 ng·h/mL±20%, and a mean $C_{max}$ of about 800-925 ng/mL±20% is achieved.

In yet another further embodiment, the invention also pertains to a pharmaceutical formulation, comprising 800 mgs of an active agent (e.g., PDS), and a pharmaceutically acceptable carrier, wherein, when the formulation is orally administered to a subject: when said subject is healthy, a mean plasma concentration profile of the active agent having a mean $AUC_\infty$ of about 4,000-6,000 ng~h/mL±20%, and a mean $C_{max}$ of about 1,200-1,300 ng/mL±20% is achieved; or when the subject has mild renal impairment, a mean plasma concentration profile of the active agent having a mean $AUC_\infty$ of about 12,000-14,000 ng·h/mL±20%, and a mean $C_{max}$ of about 2,500-3,500 ng/mL±20% is achieved; or when the subject has moderate renal impairment, a mean plasma concentration profile of the active agent having a mean $AUC_\infty$ of about 9,000-11,000 ng·h/mL±20%, and a mean $C_{max}$ of about 2,000-2,200 ng/mL±20% is achieved; or when the subject has severe renal impairment, a mean plasma concentration profile of the active agent having a mean $AUC_\infty$ of about 40,000-46,000 ng·h/mL±20%, and a mean $C_{max}$ of about 2,100-2,300 ng/mL±20% is achieved.

In yet another further embodiment, the invention also pertains, at least in part, to a pharmaceutical formulation, which comprises an active agent (e.g., PDS), and a pharmaceutically acceptable carrier, wherein, when the formulation is orally administered to a subject having AA amyloidosis for twenty-four months: in a dose of 400 mg of the active agent, a mean plasma concentration profile of the active agent having a mean $AUC_\infty$ of about 25,000-26,000 ng·h/mL±20%, and a mean $C_{max}$ of about 2,000-2,300 ng/mL±20% is achieved; or in a dose of 800 mg of the active agent, a mean plasma concentration profile of the active agent having a mean $AUC_\infty$ of about 20,000-22,000 ng·h/mL±20%, and a mean $C_{max}$ of about 1,600-2,000 ng/mL±20% is achieved; or in a dose of 1200 mg of the active agent, a mean plasma concentration profile of the active agent having a mean $AUC_\infty$ of about 8,000-10,000 ng·h/mL±20%, and a mean $C_{max}$ of about 800-1,000 ng/mL±20% is achieved.

In yet another further embodiment, the invention also pertains, at least in part, to a pharmaceutical formulation, comprising an active agent (e.g., PDS), and a pharmaceutically acceptable carrier, wherein, when the formulation is orally administered to healthy male subjects for seven days: in a dose of 400 mg QID of the active agent, a mean plasma concentration profile of the active agent having a mean $AUC_\infty$ of about 10,000-11,500 ng·h/mL±20%, and a mean $C_{max}$ of about 900-1100 ng/mL±20% is achieved; or in a dose of 800 mg QID of the active agent, a mean plasma concentration profile of the active agent having a mean $AUC_\infty$ of about 19,000-21,000 ng·h/mL±20%, and a mean $C_{max}$ of about 1,600-1,800 ng/mL±20% is achieved; or in a dose of 1600 mg TID of the active agent, a mean plasma concentration profile of the active agent having a mean $AUC_\infty$ of about 25,000-27,000 ng·h/mL±20%, and a mean $C_{max}$ of about 4,000-6,000 ng/mL±20% is achieved; or in a dose of 1600 mg QID of the active agent, a mean plasma concentration profile of the active agent having a mean $AUC_\infty$ of about 23,000-25,500 ng·h/mL±20%, and a mean $C_{max}$ of about 4,500-6,500 ng/mL±20% is achieved.

In yet another embodiment, the invention also pertains to a method of stabilizing or improving renal function or delaying progression of renal disease in a subject having AA amyloidosis. The method includes orally administering a formulation comprising 1,3-propanedisulfonic acid or a pharmaceutically acceptable salt thereof and one or more pharmaceutically acceptable carriers, in an amount determined in accordance with the subject's rate of creatinine clearance. For example, when the formulation is administered in a dose of 400 mg, a mean plasma concentration profile of 1,3-propanedisulfonic acid having a mean $AUC_\infty$ of about 10,000-12,000 ng·h/mL±20%, and a mean $C_{max}$ of about 800-900 ng/mL±20% is achieved; or when the formulation is administered in a dose of 800 mg, a mean plasma concentration profile of the active agent having a mean $AUC_\infty$ of about 9,000-10,500 ng·h/mL±20%, and a mean $C_{max}$ of about 750-875 ng/mL±20% is achieved; or when the formulation is administered in a dose of 1200 mg, a mean plasma concentration profile of the active agent having a mean $AUC_\infty$ of about 5,000-6,000 ng·h/mL±20%, and a mean $C_{max}$ of about 800-925 ng/mL±20% is achieved.

In yet another further embodiment, the invention also pertains, at least in part, to a pharmaceutical formulation, which comprises an active agent which is 1,3-propane disulfonic acid or a pharmaceutically acceptable salt thereof, and a pharmaceutically acceptable carrier. Furthermore, when this formulation is orally administered to a subject having AA amyloidosis: in a dose of 400 mg of the active agent to a subject having a creatinine clearance rate of less than about 30 mL/min, a mean plasma concentration profile of the active agent having a mean $AUC_\infty$ of about 6,000-17,000 ng·h/ mL±20%, and a mean $C_{max}$ of about 500-1200 ng/mL±20% is achieved; or in a dose of 800 mg of the active agent to a subject having a creatinine clearance rate of from about 30 to about 80 mL/min, a mean plasma concentration profile of the active agent having a mean $AUC_\infty$ of about 3000-20000 ng·h/mL±20%, and a mean $C_{max}$ of about 300-1200 ng/mL±20% is achieved; or in a dose of 1200 mg of the active agent to a subject having a creatinine clearance rate of greater than about 80 mL/min, a mean plasma concentration profile of the active agent having a mean $AUC_\infty$ of about 2,000-11,000 ng·h/mL±20%, and a mean $C_{max}$ of about 400-1500 ng/mL±20% is achieved.

In yet another embodiment, the invention also pertains, at least in part, to a method of stabilizing or improving renal function or delaying progression of renal disease in a subject having AA amyloidosis, comprising orally administering a formulation comprising 1,3-propanedisulfonic acid or a pharmaceutically acceptable salt thereof and one or more pharmaceutically acceptable carriers, in an amount determined in accordance with the subject's rate of creatinine clearance. Furthermore, when the formulation is administered in a dose of 400 mg, a mean plasma concentration profile of 1,3-propanedisulfonic acid having a mean $AUC_\infty$ of about 6,000-17,000 ng·h/mL±20%, and a mean $C_{max}$ of about 500-1200 ng/mL±20% is achieved; or when the formulation is administered in a dose of 800 mg, a mean plasma concentration profile of the active agent having a mean $AUC_\infty$ of about 3000-20000 ng·h/mL±20%, and a mean $C_{max}$ of about 300-1200 ng/mL±20% is achieved; or when the formulation is administered in a dose of 1200 mg, a mean plasma concentration profile of the active agent having a mean $AUC_\infty$ of about 2,000-11,000 ng·h/mL±20%, and a mean $C_{max}$ of about 400-1500 ng/mL±20% is achieved.

DETAILED DESCRIPTION OF THE INVENTION

Figure 1:
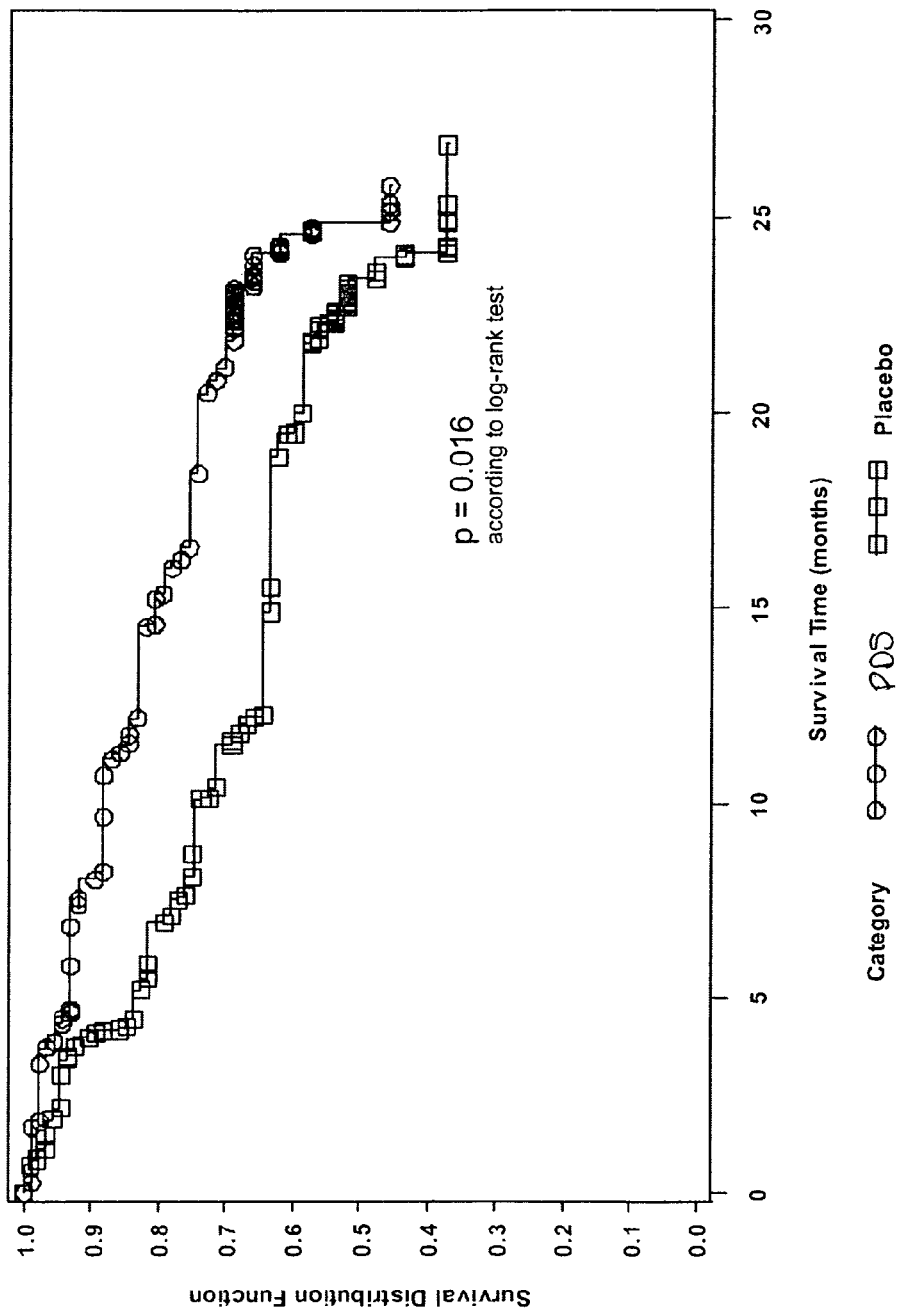
FIG. 1 is a graph depicting a Kaplan-Meier curve for the time to the first "worse" event for subjects administered PDS versus a placebo.

A. Methods Of Treating A Target Subject Using Compounds Of The Invention

In one embodiment, the invention pertains, at least in part, to a method of treating or preventing AA amyloidosis in a target subject who is being treated for AA amyloidosis and has or is susceptible to a parameter associated with renal impairment. The method includes administering to the target subject a therapeutically effective amount of a compound of the formula:

$$Y-(CH_2)_n-[CH_2Y]_m \quad (I)$$

wherein Y is $SO_3X$ or $OSO_3X$ independently chosen for each occurrence; X is cationic group independently chosen for each occurrence; n is 1, 2, 3 or 4; and m is 1 or 2, such that AA amyloidosis is treated or prevented while maintaining an acceptable tolerance index (ATI) for a parameter associated with renal impairment (PRI).

In another embodiment, the invention includes a method of treating or preventing AA amyloidosis in a target subject, who is being treated for AA amyloidosis and has or is susceptible to a secondary disorder or state associated with gastrointestinal impairment. The method includes administering to the target subject a therapeutically effective amount of a compound of formula (I), while maintaining an acceptable tolerance index (ATI) for a parameter associated with gastrointestinal impairment (PGI).

Generally, AA amyloidosis is a manifestation of a number of diseases that provoke a sustained acute phase response. Such diseases include chronic inflammatory disorders, chronic local or systemic microbial infections, and malignant neoplasms. The most common form of reactive or secondary (AA) amyloidosis is seen as the result of long-standing inflammatory conditions. For example, subjects with Rheumatoid Arthritis or Familial Mediterranean Fever (which is a genetic disease) can develop AA amyloidosis. The terms "AA amyloidosis," "secondary amyloidosis" and "secondary (AA) amyloidosis" are used interchangeably.

AA fibrils are generally composed of 8,000 Dalton fragments (AA peptide or protein) formed by proteolytic cleavage of serum amyloid A protein (ApoSAA), a circulating apolipoprotein which is mainly synthesized in hepatocytes in response to such cytokines as IL-1, IL-6 and TNF. Once secreted, ApoSAA is complexed with HDL. Deposition of AA fibrils can be widespread in the body, with a preference for parenchymal organs. The kidneys are usually a deposition site, and the liver and the spleen may also be affected. Deposition is also seen in the heart, gastrointestinal tract, and the skin.

Underlying diseases which can lead to the development of AA amyloidosis include, but are not limited to, inflammatory diseases, such as chronic inflammatory disease, rheumatoid arthritis, ankylosing spondylitis, psoriasis, psoriatic arthropathy, Reiter's syndrome, Adult Still's disease, Behcet's syndrome, familial Mediterranean fever, inflammatory bowel disease, hereditary periodic fevers, juvenile chronic arthritis, juvenile rheumatoid arthritis, ulcerative colitis, chronic fevers, bronchiostasis, malaria, vasculitis, IV drug use, psoriatic arthritis, lupus erythematosus arthritis, periarthritis nodosa, Wegner's granulomatosis, Muckle-Wells syndrome and Crohn's disease. AA deposits are also produced as a result of chronic infections, e.g., AIDS, HIV, hepatitis B, hepatitis C, chronic microbial infections, e.g., leprosy, tuberculosis, bronchiectasis, decubitus ulcers, pyelonephritis, osteomyelitis, acne conglobata, common variable immunodeficiency, hypolagammaglobulinemia, cystic fibrosis, pulmonary tuberculosis, pulmonary infection(s), recurrent abscesses, Behcet's disease, and Whipple's disease. Certain malignant neoplasms can also result in AA fibril amyloid deposits. These include such conditions as Hodgkin's lymphoma, renal carcinoma, carcinomas of gut, lung and urogenital tract, basal cell carcinoma, hepatoma, Castleman's disease, Schnitzler's syndrome, Waldenstrom's disease, and hairy cell leukemia.

The term "subject" includes living organisms in which AA amyloidosis or an amyloid related disease can occur, or which are susceptible to AA amyloidosis or amyloid related diseases. The term "subject" includes animals (e.g., mammals, e.g., cats, dogs, horses, pigs, cows, goats, sheep, rodents, e.g., mice or rats, rabbits, squirrels, bears, primates (e.g., chimpanzees, monkeys, gorillas, and humans)), as well as chickens, ducks, peking ducks, geese, and transgenic species thereof.

The term "target subject," refers to a subject, e.g., a human, specifically chosen to receive the compositions or compounds of formula (I). Accordingly, in some embodiments, target subjects include subjects who are at risk of or have been diagnosed with an AA amyloid related disease, e.g., AA amyloidosis. Subjects at risk of developing AA amyloidosis include those with an underlying disease, such as an inflammatory disease, infection, hereditary fever or neoplasm. In other embodiments, target subjects include subjects that have or are susceptible to a parameter associated with renal impairment and/or gastrointestinal impairment. Target subjects also may include subjects who have been diagnosed with both an AA amyloid related disease and are known to have a parameter associated with renal impairment and/or gastrointestinal impairment. The preferred target subject is a human.

The terms "Acceptable Tolerance Index" and "ATI" are used interchangeably to refer to a level of illness in a subject that is considered satisfactory at a given time point in the disease or disorder afflicting the subject. In some embodiments, an ATI is an improvement or stabilization of the illness in a subject, as described herein. In other embodiments, an ATI is less worsening of an illness in a subject, as compared to a previous time point, e.g., when a subject is experiencing a rapid increase in serum creatinine levels, an ATI may be a slower increase in serum creatinine levels. Accordingly, in one embodiment, an ATI is less worsening in a subject of at least one of the parameters associated with renal impairment or gastrointestinal impairment. In another embodiment, an ATI is less worsening in a subject of at least two of the parameters associated with renal impairment and/or gastrointestinal impairment. In still another embodiment, an ATI is less worsening in a subject of at least three, four or five of the parameters associated with renal impairment and/or gastrointestinal impairment.

The terms "parameter associated with renal impairment," and "PRI" are used interchangeably to include parameters generally associated with abnormal kidney function, such as, but not limited to decreased creatinine clearance, increased levels of serum creatinine, proteinuria, progression to dialysis/End Stage Renal Disease (ESRD), hypoalbuminemia, and/or edema. In some embodiments, the parameter associated with renal impairment is caused, at least in part, by AA amyloidosis or the presence of amyloid A protein in the body.

The terms "parameter associated with gastrointestinal impairment," and "PGI" include parameters generally associated with abnormal gastrointestinal function, such as, but not limited to, chronic diarrhea and/or loss of body weight. In some embodiments, the parameter associated with gastrointestinal impairment is caused, at least in part, by AA amyloidosis or the presence of amyloid A protein in the body.

The terms "treatment" or "treating" of a subject includes the application or administration of a compound of the invention to a subject (or application or administration of a compound of the invention to a cell or tissue from a subject) with the purpose of stabilizing, curing, healing, alleviating, relieving, altering, remedying, less worsening, ameliorating, improving, or affecting the disease or condition, the symptom of the disease or condition, or the risk of (or susceptibility to) the disease or condition. The term "treating" refers to any indicia of success in the treatment or amelioration of an injury, pathology or condition, including any objective or subjective parameter such as abatement; remission; lessening of the rate of worsening; stabilization, diminishing of symptoms or making the injury, pathology or condition more tolerable to the subject; slowing in the rate of degeneration or decline; making the final point of degeneration less debilitating; or improving a subject's physical or mental well-being. In an embodiment, the term "treating" can include increasing a subject's life expectancy.

The term "remission of chronic diarrhea" refers to no episodes of chronic diarrhea and no chronic use of antidiarrheal agents for at least four consecutive months.

In one embodiment, the progression to dialysis is delayed or prevented in a subject, e.g., a subject having AA amyloidosis. For example, a subject's progression to dialysis may be delayed by 1 month or longer, 2 months or longer, 3 months or longer, 4 months or longer, 5 months or longer, 6 months or longer, 7 months or longer, 8 months or longer, 10 months or longer, 11 months or longer, 1 year or longer, 1.5 years or longer, 2 years or longer, 3 years or longer, 4 years or longer, 5 years or longer, 7.5 years or longer, 10 years or longer, 15 years or longer, or 20 years or longer. In a particular embodiment, it is delayed by about 6 months.

In another embodiment, the term "treating" includes decreasing the risk of any "worse" event of renal decline (see Example 3) or all-cause mortality by at least 5% or greater, at least 10% or greater, at least 15% or greater, at least 20% or greater, at least 30% or greater, at least 40% or greater, at least 50% or greater, at least 60% or greater, or at least 63% or greater. In another embodiment, the risk of any "worse" event of renal decline or all-cause mortality is decreased 7%-63%.

In another embodiment, the term "treating" also includes increasing the mean time to the first "worse" event. The increase may be about 0.5 months or longer, about 1 month or longer, about 2 months or longer, about 3 months or longer, about 4 months or longer, about 5 months or longer, about 6 months or longer, about 7 months or longer, about 8 months or longer, about 9 months or longer, about 10 months or longer, or about 11 months or longer. In another embodiment, the time is increased by about: 2.8 months ±7.5 months longer in PDS treated subjects.

In another embodiment, the subject's creatinine clearance rate is stabilized or improved. For example, a subject's creatinine clearance rate may be increased by about 10% or greater, by about 20% or greater, by about 30% or greater, by about 40% or greater, by about 50% or greater, by about 60% or greater, by about 70% or greater, by about 80% or greater, by about 90% or greater, or by about 100% or greater as compared to the subject's level prior to treatment with the compounds of the invention.

In another embodiment, the risk of a 50% or greater decrease in creatinine clearance is reduced at least about 5% or more, at least about 10% or more, at least about 15% or more, or at least about 18% or more. In a further embodiment, the risk of a 50% or greater decrease in creatinine clearance is reduced about 18% to 72%.

In another embodiment, a subject's serum creatinine, serum albumin levels, and/or serum alkaline phosphatase levels are stabilized or improved. For example, a subject's serum creatinine, serum alin levels, and/or serum alkaline phosphatase levels may be increased by about 10% or greater, by about 20% or greater, by about 30% or greater, by about 40% or greater, by about 50% or greater, by about 60% or greater, by about 70% or greater, by about 80% or greater, by about 90% or greater, or by about 100% or greater as compared to the subject's level prior to treatment with the compounds of the invention.

In a further embodiment, the risk of the doubling of serum creatinine is reduced by at least 5% or greater, at least 10% or greater, at least 11% or greater, at least 12% or greater, at least 13% or greater, or at least 14% or greater. In a further embodiment, a subject's risk of having their serum creatinine is double is reduced from about 14% to about 81%.

In another embodiment, the term "treating" also includes increasing the mean time to the doubling of serum creatinine. The increase may be about 0.5 months or longer, about 1 month or longer, about 2 months or longer, about 3 months or longer, about 4 months or longer, about 5 months or longer, about 6 months or longer, about 7 months or longer, about 8 months or longer, about 9 months or longer, about 10 months or longer, about 11 months or longer, or about a year or longer.

In another embodiment, a subject's proteinuria levels, visceral amyloid burden, and/or amyloid content in aspirated fat tissue are stabilized or improved. For example, a subject's proteinuria levels, visceral amyloid burden, and/or amyloid content in aspirated fat tissue may be reduced by about 10% or greater, by about 20% or greater, by about 30% or greater, by about 40% or greater, by about 50% or greater, by about 60% or greater, by about 70% or greater, by about 80% or greater, by about 90% or greater, or by about 100% or greater as compared to the subject's level prior to treatment with the compounds of the invention.

In another embodiment, a subject's visceral amyloid burden is reduced or stabilized. A subject's visceral amyloid burden can be assessed by, for example, using $^{123}$I-radiolabeled serum amyloid P component (SAP) scintigraphy. SAP binds specifically to amyloid fibrils and is retained in tissue amyloid deposits for prolonged periods, apparently protected from the normal rapid catabolism to which it is subject in the circulation. Scintigraphic imaging with radiolabeled SAP has been developed as a specific noninvasive method for assessing visceral amyloid burden (Hawkins P N et al. *N Engl J Med,* 1990; 323:508-13). Visceral amyloid burden can be quantified, for example, by visual assessment of whole body scintigraphs obtained 24 hours after the injection of the radionuclide.

In another embodiment, a subject's amyloid content in aspirated fat tissue is reduced or stabilized. The term "amyloid content in aspirated fat tissue" refers to the content of amyloid A in aspirated fat tissue. Changes in amyloid A content in aspirated fat tissue can be measured semi-quantitatively by Congo red staining. Amyloid A content in fat tissue can be measured quantitatively, for example, by using a monoclonal antibody-based sandwich ELISA using fat tissue collected from a subject. (Hazenberg B et al. *Ann Rheum Dis,* 1999; 58: 96-102).

The term "orthostatic hypotension" refers to a sudden fall in blood pressure that occurs when a person assumes a standing position. Symptoms, which generally occur after sudden standing, include dizziness, lightheadedness, blurred vision, and syncope (temporary loss of consciousness). The autonomic nervous system (ANS) is sometimes affected in AA amyloidosis. A postural decrease in blood pressure (e.g. a drop from the supine to standing position of $\geq$20 mmHg in systolic blood pressure or 10 mmHg in diastolic blood pressure sustained for at least 3 min) is a sign of ANS dysfunction.

In another embodiment, a subject's body weight loss is improved or stabilized, or the subject gains weight. For example, a subject might gain 5% or more, about 10% or more, about 20% or more, about 30% or more, about 40% or more, about 50% or more, or about 60% or more of their body weight prior to treatment with the compounds of the invention.

In another embodiment a subject's nephrotic syndrome may be stabilized or go into remission. In another embodiment, a subject's edema may be resolved or alleviated. In another embodiment, the stabilization, improvement, cure, or remission of diarrhea in a subject may occur. In yet another embodiment, there may be stabilization or reduction of orthostatic hypotension, splenomegaly, and/or hepatomegaly in a subject.

In one embodiment, remission of nephrotic syndrome includes a decrease in proteinuria to $\leq$1 g/24 h and either an increase in serum albumin to greater than 3.4 g/dL or resolution of an edema and/or discontinuation of diuretics in response to improvement in edema.

The term "therapeutically effective amount" refers to the amount of a compound which is effective to treat a subject, e.g., treat a subject for AA amyloidosis or an amyloid related disease or treat a subject having an underlying disease, such as, but not limited to, an inflammatory disorder, a malignant neoplasm, or chronic microbial infection. The therapeutically effective amount may vary based on the particular disorder(s) the subject is suffering from, the age, weight, and lifestyle of a particular subject. In addition, the therapeutically effective amount may depend on the severity of the disease state, organ function, kidney function, or underlying disease (e.g., the subject may be suffering from an inflammatory disease, a malignant neoplasm, a chronic infection). In an embodiment, the subject is nephrotic. In another embodiment, the subject is non-nephrotic.

The term "nephrotic" refers to a subject suffering from nephrotic syndrome. Nephrotic syndrome is generally defined as heavy proteinuria (e.g., urinary protein >3 g/24 h) in combination with the two following extrarenal features 1) hypoalbuminemia (e.g., serum albumin<3.4 g/dL); and 2) a peripheral edema by physical examination and/or use of diuretics to treat edema.

The term "non-nephrotic" refers to a subject who has not yet progressed to nephrotic syndrome or who is in remission of nephrotic syndrome. Remission of nephrotic syndrome is a decrease in proteinuria to $\leq$1 g/24 h and an improvement in one of the two following extrarenal features: 1) increase in serum albumin to $\geq$3.4 g/dL or 2) resolution of edema and/or discontinuation of diuretics in response to improvement in edema. Progression to nephrotic syndrome is an increase in proteinuria to >3 g/24 h and occurrence of the two following extrarenal features: 1) hypoalbuminemia (serum albumin<3.4 g/dL) and 2) edema and/or use of diuretics to treat edema.

In another further embodiment, the invention also pertains to a method of treating or preventing amyloid related disease in a subject by administering to the subject a therapeutically effective amount of a compound of formula (I) at a dosage selected based upon the subject's creatinine clearance rate, proteinuria level, and/or serum albumin levels.

The term "creatinine clearance" is art recognized and refers to the rate at which the kidneys clear creatinine from the blood. Creatinine is a substance that is easily excreted by the kidney in healthy subjects. Creatinine clearance generally compares the level of creatinine in urine with the creatinine level in the blood. Clearance is often measured as milliliters/minute (ml/min).

The dosage administered in the methods of the present invention may be selected based upon creatinine clearance rate. For example, the dosage of the compound of formula (I) may be selected to be about 1200 mg twice daily for a creatinine clearance rate of >80 mL/min. For a creatinine clearance rate of between about 30 and 80 mL/min, the dosage of the compound of formula (I) may be selected to be about 800 mg twice daily. For a creatinine clearance rate of between about 20 and 30 mL/min, the dosage of the compound of formula (I) may be selected to be about 400 mg twice daily. In addition, the dosage also may be adjusted based on the changing creatinine clearance rates in the subject.

In one embodiment, the dosage may be selected such that desired pharmacokinetic parameters and/or biologically favorable parameters are obtained after administration of the compound of the invention to the subject. In one embodiment, the dosage is selected such that once administered to the subject, the mean $AUC_{ss}$ in the subject is about 7,000 to about 26,000 ng.h/mL and the mean steady state concentration is about 500 to about 1200 ng/mL. In another embodiment, the dosage is selected such that once administered to the subject, the $C_{max}$ in the subject is about 1,200 to about 3,100 ng/mL and the $AUC_\infty$ is about 5,000 to about 43,000 ng.h/mL. In subjects with impaired renal function, the dosages needed to achieve a particular $AUC_{ss}$, $AUC_\infty$, $C_{max}$, and steady state mean concentration may need to be adjusted.

In a further embodiment, the $C_{max}$, $AUC_{0-tlast}$, and/or $AUC_\infty$ may vary for a particular subject by about ±10%, by about ±20%, by about ±30%, or by about ±40% as compared to the values shown in Table 1.

The language "amyloid-related disease" refers to a pathological condition characterized by the presence of amyloid fibers. "Amyloid" is a generic term referring to a group of diverse but specific protein deposits (intracellular or extracellular) which are seen in a number of different diseases. Though diverse in their occurrence, all amyloid deposits have common morphologic properties, stain with specific dyes (e.g., Congo red), and have a characteristic red-green birefringent appearance in polarized light after staining. They also share common ultrastructural features and common X-ray diffraction and infrared spectra.

The invention also pertains, at least in part, to another method for treating or preventing AA amyloidosis in a subject. This method includes administering to a subject in need thereof, a therapeutically effective amount of a compound of formula (I), which is administered in a dosage such that an effective systemic exposure is provided in a subject, for example, as measured by, e.g., AUC, $C_{max}$, $AUC_{ss}$, $C_{ss}$, $T_{max}$, etc.

The term "target plasma concentration" refers to a range of concentrations in the subject of the compound of the invention which result in treatment of the subject for AA amyloidosis. In one embodiment, the subject maintains a steady state concentration ($C_{ss}$) of about 500 to about 1200 ng/mL. In another embodiment, the subject maintains an $AUC_{ss}$ from about 7000 to about 26,000 ng.h/mL. For example, the subject may maintain a steady state concentration of about 600 to about 700 ng/mL, or about 900 to about 1100 ng/mL and/or an $AUC_{ss}$ of about 8000 to about 9000 ng.h/mL, or about 11,000 to about 13,000 ng.h/mL, or about 23,000 to about 26,000 ng.h/mL, or about 15,500 to about 16,500 ng.h/mL. In a further embodiment the $AUC_{ss}$ or the steady state concentration are within ±20% of these values.

In addition, the invention pertains, at least in part, to a method of stabilizing or improving renal and/or gastrointestinal function in a subject. The method includes administering to a subject a therapeutically effective amount of a compound of formula (I).

In a further embodiment, the invention also pertains, at least in part, to a pharmaceutical formulation. The formulation comprises an active agent which is 1,3-propane disulfonic acid or a pharmaceutically acceptable salt thereof in an amount effective to treat or prevent AA amyloidosis, and a pharmaceutically acceptable carrier. Furthermore, when the formulation is orally administered to a healthy subject, a mean plasma concentration profile of the active agent having a mean $AUC_\infty$ of about from 2900 to about 9000 ng·h/mL±20% and a mean $C_{max}$ of about from 450 to about 2150 ng/mL±20% is achieved. In alternate embodiment, when the formulation is orally administered to a healthy subject, a mean plasma concentration profile of the active agent having a mean $AUC_\infty$ of from about 2,900 to about 9,000 ng·h/mL±20% is achieved. In another alternate embodiment, when the formulation is orally administered to a healthy subject, a mean plasma concentration profile of the active agent having a mean $C_{max\ of}$ about from 450 to about 2150 ng/mL±20% is achieved.

In another embodiment, the invention also pertains to a pharmaceutical formulation, which comprises an active agent which is 1,3-propane disulfonic acid or a pharmaceutically acceptable salt thereof, and a pharmaceutically acceptable carrier. In this embodiment, when the formulation is orally administered to a subject having AA amyloidosis: in a dose of 400 mg of the active agent to a subject having a creatinine clearance rate of less than about 30 mL/min, a mean plasma concentration profile of the active agent having a mean $AUC_\infty$ of about 10,000-12,000 ng·h/mL±20%, and a mean $C_{max}$ of about 800-900 ng/mL±20% is achieved; or in a dose of 800 mg of the active agent to a subject having a creatinine clearance rate of from about 30 to about 80 mL/min, a mean plasma concentration profile of the active agent having a mean $AUC_\infty$ of about 9,000-10,500 ng·h/mL±20%, and a mean $C_{max}$ of about 750-875 ng/mL±20% is achieved; or in a dose of 1200 mg of the active agent to a subject having a creatinine clearance rate of greater than about 80 mL/min, a mean plasma concentration profile of the active agent having a mean $AUC_\infty$ of about 5,000-6,000 ng·h/mL±20%, and a mean $C_{max}$ of about 800-925 ng/mL±20% is achieved.

In another embodiment, this invention also pertains to a pharmaceutical formulation, comprising 800 mgs of an active agent, which is 1,3-propane disulfonic acid or a pharmaceutically acceptable salt thereof, and a pharmaceutically acceptable carrier. Furthermore, when this formulation is orally administered to a subject: when the subject is healthy, a mean plasma concentration profile of the active agent having a mean $AUC_\infty$ of about 4,000-6,000 ng·h/mL±20%, and a mean $C_{max}$ of about 1,200-1,300 ng/mL±20% is achieved; or when the subject has mild renal impairment, a mean plasma concentration profile of the active agent having a mean $AUC_\infty$ of about 12,000-14,000 ng·h/mL±20%, and a mean $C_{max}$ of about 2,500-3,500 ng/mL±20% is achieved; or when the subject has moderate renal impairment, a mean plasma concentration profile of the active agent having a mean $AUC_\infty$ of about 9,000-11,000 ng·h/mL±20%, and a mean $C_{max}$ of about 2,000-2,200 ng/mL±20% is achieved; or when the subject has severe renal impairment, a mean plasma concentration profile of the active agent having a mean $AUC_\infty$ of about 40,000-46,000 ng·h/mL±20%, and a mean $C_{max}$ of about 2,100-2,300 ng/mL±20% is achieved.

In another further embodiment, the invention pertains to a pharmaceutical formulation, comprising an active agent which is 1,3-propane disulfonic acid or a pharmaceutically acceptable salt thereof, and a pharmaceutically acceptable carrier. Furthermore, when this formulation is orally administered to a subject having AA amyloidosis for twenty-four months: in a dose of 400 mg of the active agent, a mean plasma concentration profile of the active agent having a mean $AUC_\infty$ of about 25,000-26,000 ng·h/mL±20%, and a mean $C_{max}$ of about 2,000-2,300 ng/mL±20% is achieved; or in a dose of 800 mg of the active agent, a mean plasma concentration profile of the active agent having a mean $AUC_\infty$ of about 20,000-22,000 ng·h/mL±20%, and a mean $C_{max}$ of about 1,600-2,000 ng/mL±20% is achieved; or in a dose of 1200 mg of the active agent, a mean plasma concentration profile of the active agent having a mean $AUC_\infty$ of about 8,000-10,000 ng·h/mL±20%, and a mean $C_{max}$ of about 800-1,000 ng/mL±20% is achieved.

In another embodiment, the invention also pertains to a pharmaceutical formulation, comprising an active agent which is 1,3-propane disulfonic acid or a pharmaceutically acceptable salt thereof, and a pharmaceutically acceptable carrier. Furthermore, wherein, when this formulation is orally administered to healthy male subjects for seven days: in a dose of 400 mg QID of the active agent, a mean plasma concentration profile of the active agent having a mean $AUC_\infty$ of about 10,000-11,500 ng·h/mL±20%, and a mean $C_{max}$ of about 900-1100 ng/mL±20% is achieved; or in a dose of 800 mg QID of the active agent, a mean plasma concentration profile of the active agent having a mean $AUC_\infty$ of about 19,000-21,000 ng·h/mL±20%, and a mean $C_{max}$ of about 1,600-1,800 ng/mL±20% is achieved; or in a dose of 1600 mg TID of the active agent, a mean plasma concentration profile of the active agent having a mean $AUC_\infty$ of about 25,000-27,000 ng·h/mL±20%, and a mean $C_{max}$ of about 4,000-6,000 ng/mL±20% is achieved; or in a dose of 1600 mg QID of the active agent, a mean plasma concentration profile of the active agent having a mean $AUC_\infty$ of about 23,000-25,500 ng·h/mL±20%, and a mean $C_{max}$ of about 4,500-6,500 ng/mL±20% is achieved.

In another furthe embodiment, the invention also pertains to a method of stabilizing or improving renal function or delaying progression of renal disease in a subject having AA amyloidosis. The method includes orally administering a formulation comprising 1,3-propanedisulfonic acid or a pharmaceutically acceptable salt thereof and one or more pharmaceutically acceptable carriers, in an amount determined in accordance with the subject's rate of creatinine clearance. Furthermore, when the formulation is administered in a dose of 400 mg, a mean plasma concentration profile of 1,3-propanedisulfonic acid having a mean $AUC_\infty$ of about 10,000-12,000 ng·h/mL±20%, and a mean $C_{max}$ of about 800-900 ng/mL±20% is achieved; or when the formulation is administered in a dose of 800 mg, a mean plasma concentration profile of the active agent having a mean $AUC_\infty$ of about 9,000-10,500 ng·h/mL±20%, and a mean $C_{max}$ of about 750-875 ng/mL±20% is achieved; or when the formulation is administered in a dose of 1200 mg, a mean plasma concentration profile of the active agent having a mean $AUC_\infty$ of about 5,000-6,000 ng·h/mL±20%, and a mean $C_{max}$ of about 800-925 ng/mL±20% is achieved.

In a further embodiment, the dose is 400 mg when the subject's rate of creatinine clearance is less than about 30 mL/min, the dose is 800 mg when the subject's rate of creatinine clearance is from about 30 to about 80 mL/min, and the dose is 1200 mg when the subject's rate of creatinine clearance is greater than about 80 mL/min. In another further embodiment, the subject's rate of creatinine clearance is about 60 to about 90 mL/min and a dose of 1200 mg is administered.

In another embodiment, the invention pertains to a method of treating or preventing AA amyloidosis in a subject. The method includes administering to a subject in need thereof, a therapeutically effective amount of a compound of formula (I) in combination with a second agent, such that AA amyloidosis is treated or prevented.

The term "in combination with" refers to the concurrent administration of a compound of formula (I) and a second agent; the administration of the compound of formula (I) prior to the administration of the second agent; or administration of the second agent prior to administration of the compound of formula (I).

The term "second agent" includes drugs known to treat underlying diseases, e.g., inflammatory diseases (e.g., chronic inflammatory disease, rheumatoid arthritis, juvenile chronic arthritis, ankylosing spondylitis, psoriasis, psoriatic arthropathy, Reiter's syndrome, psoriatic arthritis, lupus erythematosus arthritis, periarthritis nodosa, Wegner's granulomatosis, Muckle-Wells syndrome, Adult Still's disease, Behcet's syndrome, familial Mediterranean fever, inflammatory bowel disease, hereditary periodic fevers, and Crohn's disease, etc.), diseases associated with chronic infections (e.g., AIDS, HIV, hepatitis B, hepatitis C, etc.), diseases associated with chronic microbial infections (e.g., leprosy, tuberculosis, bronchiectasis, decubitus ulcers, pyelonephritis, osteomyelitis, Whipple's disease, acne conglobata, common variable immunodeficiency, pulmonary tuberculosis, pulmonary infection(s), recurrent abscesses, Behcet's Disease, hypolagammaglobulinemia, cystic fibrosis, etc.), or certain malignant neoplasms (e.g., Hodgkin's lymphoma, renal carcinoma, carcinomas of gut, lung and urogenital tract, basal cell carcinoma, Castleman's disease, Schnitzler's syndrome, hepatoma, Waldenstrom's disease, and hairy cell leukemia). The term "second agent" also includes rescue agents, chemotherapeutic agents, anti-inflammatory agents, e.g., non-steroidal anti-inflammatory agents, etc., and antibiotics. Examples of second agents include methotrexate, colchicine, anti-TNF antibodies and anti-interleukin 1 or 6 antibodies.

Examples of nonsteroidal anti-inflammatory agents ("NSAIDs") include ibuprofen, naproxen, sulindac, and indomethacin. Other anti-inflammatory agents include COX-2 inhibitors (such as Vioxx™ and Celebrex™), cytokine inhibitors (such as thalidomide disclosed in WO 95/04533 and dexanabinol) complement inhibitors, leukotriene receptor antagonists and combinations thereof. Examples include acetic acid derivatives sulindac (Clinoril™, Merck & Co., Inc., Rahway, N.J.), indomethacin (Indocin™, Merck & Co., Inc., Rahway, N.J.); etodolac (Lodine™, Wyeth, Madison, N.J.), nabumetone (Relafen™, GlaxoSmithKline, Middlesex, England), tolmetin sodium (Tolectin™, McNeil Pharmaceuticals, Spring House, Pa.); anthranilic acid derivatives: meclofenamate sodium (Meclomen™, Pfizer, New York, N.Y.), mefenamic acid (Ponstel™, Pfizer, New York, N.Y.); enolic acid derivatives: piroxicam (Feldene™, Pfizer, New York, N.Y.), Mobic™ (meloxicam); phenylacetic acid derivatives: arthrotec (diclofenac/misoprostol), Voltaren™ (diclofenac); propionic acid derivatives: naproxen sodium (Anaprox™, Naprosyn, Hoffmann-La Roche Inc. (Roche), Nutley, N.J.), flurbiprofen (Ansaid™, Upjohn, now Pfizer, New York, N.Y.), oxaprozin (Daypro™, G.D Searle, now Pfizer, New York, N.Y.); ibuprofen (Motrin™, Upjohn, now Pfizer, New York, N.Y.), fenoprofen calcium (Nalfon™, Dista, Ranbaxy, Princeton, N.J.), ketoprofen (Oruvail™ or Orudis™, Wyeth, Madison, N.J.), ketorolac tromethamine (Toradol™, Syntex Laboratories, Hoffmann-La Roche Inc. (Roche), Nutley, N.J.); salicylic acid derivative: diflunisal (Dolobid™, Merck & Co., Inc., Rahway, N.J.); and COX-2 selective inhibitors: Bextra™ (valdecoxib), Celebrex™ (celecoxib, Pfizer, New York, N.Y.), and Vioxx™ (rofecoxib, Merck & Co., Inc., Rahway, N.J.), and cyclosporin (Maas BiolAB, Albuquerque, N.M.).

The language "chemotherapeutic agent" includes agents which inhibit the growth of proliferating cells or tissues wherein the growth of such cells or tissues is undesirable or otherwise treat at least one resulting symptom of such a growth. Examples of chemotherapeutic agents include: bleomycin, docetaxel (Taxotere), doxorubicin, edatrexate, etoposide, finasteride (Proscar), flutamide (Eulexin), gemcitabine (Gemzar), goserelin acetate (Zoladex), granisetron (Kytril), irinotecan (Campto/Camptosar), ondansetron (Zofran), paclitaxel (Taxol), pegaspargase (Oncaspar), pilocarpine hydrochloride (Salagen), porfimer sodium (Photofrin), interleukin-2 (Proleukin), rituximab (Rituxan), topotecan (Hycamtin), trastuzumab (Herceptin), tretinoin (Retin-A), Triapine, vincristine, and vinorelbine tartrate (Navelbine).

Other examples of chemotherapeutic agents include alkylating drugs such as nitrogen mustards (e.g., mechlorethamine ($HN_2$), cyclophosphamide, ifosfamide, Melphalan (L-sarcolysin), Chlorambucil, etc.); ethylenimines, methylmelamines (e.g., hexamethylmelamine, thiotepa, etc.), alkyl sulfonates (e.g., busulfan, etc.), nitrosoureas (e.g., carmustine (BCNU), lomustine (CCNU), semustine (methyl-CCNU), streptozocin (streptozotocin), etc.), triazenes (e.g., decarbazine (DTIC; dimethyltriazenoimidazolecarboxamide)), alkylators (e.g., cis-diamminedichloroplatinum II (CDDP)), etc.

Other examples of chemotherapeutic agents include antimetabolites such as folic acid analogs (e.g., methotrexate (amethopterin)); pyrimidine analogs (e.g., fluorouracil ('5-fluorouracil; 5-FU); floxuridine (fluorode-oxyuridine); FUdr; Cytarabine (cyosine arabinoside), etc.); purine analogs (e.g., Mercaptopurine (6-mercaptopurine; 6-MP); Thioguanine (6-thioguanine; TG); and Pentostatin (2'-deoxycoformycin)), etc.

Other examples of chemotherapeutic agents also include vinca alkaloids (e.g., vinblastin (VLB) and vincristine); topoisomerase inhibitors (e.g., etoposide, teniposide, camptothecin, topotecan, 9-amino-campotothecin CPT-11, etc.); antibiotics (e.g., dactinomycin (actinomycin D), adriamycin, daunorubicin, doxorubicin, bleomycin, plicamycin (mithramycin), mitomycin (mitomycin C). taxol, taxotere, etc.); enzymes (e.g;, L-asparaginase); and biological response modifiers (e.g., interferon-α, interleukin 2, etc.). Other chemotherapeutic agents include cis-diamminedichloroplatinum II (CDDP); crboplatin; anthracendione (e.g, mitoxantrone); hydroxyurea; procarbazine (N-methylhydrazine); and adrenocortical suppressants (e.g., mitotane, aminoglutethimide, etc.).

Other chemotherapeutic agents include adrenocorticosteroids (e.g., prednisone); progestins (e.g., hydroxyprogesterone caproate,; medroxyprogesterone acetate, megestrol acetate, etc.); estrogens (e.g., diethylstilbestrol; ethenyl estradiol, etc.); antiestrogens (e.g tamoxifen, etc.); androgens (e.g., testosterone propionate, fluoxymesterone, etc.); antiandrogens (e.g., flutamide); and gonadotropin-releasing hormone analogs (e.g., leuprolide).

The term "antibiotic agents" include antibiotics known in the art to treat microbial infections. Examples of anti-biotic agents include, but are not limited to, amoxicillin, aminoglycoside, aminoglycoside analogs, beta-lactam, beta-lactamase, beta-lactamase analogs, clindamycin, chloramphenicol, cephalosporin, cephalosporin analogs, ciprofloxacin, ciprofloxacin analogs, erythromycin, fluoroquinolone, fluoroquinolone analogs, macrolide, macrolide analogs, metronidazole, penicillin, penicillin analogs, quinolone, quinolone analogs, rifampin, streptomycin, sulfonamide, tetracycline, tetracycline analogs, trimethoprim, trimethoprim-sulfamthoxazole, and vancomycin.

The term "rescue medication" refers to any medication commenced during treatment which has the potential to suppress the underlying disease, but which is introduced with the primary indication of ameliorating features of progressive AA amyloidosis. Such medications may include, but are not limited to, colchicine, cytotoxic agents, and anti-TNF agents.

Examples of anti-TNF agents include agents which inhibit TNF, e.g., anti-TNFα antibodies. Examples of anti-TNF agents include etanercept (Enbrel™, Amgen), infliximab (Remicade™, Johnson and Johnson, see, for example U.S. Pat. No. 6,790,444), human anti-TNF monoclonal antibody (D2E7/HUMIRA™, Abbott Laboratories), CDP 571 (Celltech), and CDP 870 (Celltech).

Examples of other second agents include immunosuppressants, corticosteroids (including systemically administered corticosteroids), sulfasalazine, renin-angiotensin system blockers or antagonists, diuretics (e.g., furosemide), calcium channel blockers, beta blocking agents, antirheumatic products, Angiotensin converting enzyme inhibitors (ACEi), Angiotensin II receptor blockers (ARBs), acetylsalicylic acid, amoxicillin, calcium, calcium carbonate, chlorambucil, colchicine, cyclophosphamide, diclofenac, enalapril, folic acid, methotrexate, methylprednisolone, omeprazole, paracetamol, prednisolone, and prednisone.

In another embodiment, the invention pertains, at least in part, to a method of treating an inflammatory disease in a subject. The method includes administering to a subject in need thereof, a therapeutically effective amount of a compound of formula (I) in combination with a second agent such that the inflammatory disease is treated in the subject. In a further embodiment, the second agent is an anti-inflammatory agent.

The term "inflammatory disease" include diseases or disorders which are associated with inflammation and can be treated using the compounds of the invention. The inflammatory disease may include diseases which are associated with, cause, caused by, result from, or otherwise related to amyloidosis, e.g., AA amyloidosis. Examples of such inflammatory diseases include, but are not limited to chronic inflammatory disease, rheumatoid arthritis, juvenile chronic arthritis, ankylosing spondylitis, psoriasis, psoriatic arthropathy, Reiter's syndrome, Adult Still's disease, Behcet's syndrome, familial Mediterranean fever, inflammatory bowel disease, hereditary periodic fevers, psoriatic arthritis, lupus erythematosus arthritis, periarthritis nodosa, Wegner's granulomatosis, Muckle-Wells syndrome and Crohn's disease.

In a further embodiment, the therapeutically effective amount of the compound of the invention is effective to treat, prevent or delay the onset of AA amyloidosis and the second agent is administered in an effective amount to treat the underlying disorder, e.g., an underlying inflammatory disorder.

In yet another embodiment, the invention includes a method of treating rheumatoid arthritis in a subject. The method includes administering to a subject in need thereof, a therapeutically effective amount of a compound of formula (I) in combination with a second agent such that rheumatoid arthritis is treated in the subject. In a further embodiment, the second agent is an anti-inflammatory agent. In a further embodiment, the second agent is infliximab, which may be administered, for example by the procedure described in U.S. Pat. No. 6,790,444, incorporated herein by reference.

In a further embodiment, the second agent is an agent which is known to treat inflammatory diseases such as chronic inflammatory disease, rheumatoid arthritis, juvenile chronic arthritis, ankylosing spondylitis, psoriasis, psoriatic arthropathy, Reiter's syndrome, familial Mediterranean fever, Adult Still's disease, Behcet's syndrome, inflammatory bowel disease, psoriatic arthritis, lupus erythematosus arthritis, periarthritis nodosa, Wegner's granulomatosis, Muckle-Wells syndrome, hereditary periodic fevers, or Crohn's disease. Examples of agents which may be administered to the subject include, for example, anti-TNF agents, methotrexate, anti-inflammatory agents, and combinations thereof.

In a further embodiment, the therapeutically effective amount of the compound of the invention is effective to treat, prevent or delay the onset of AA amyloidosis and the second agent is administered in an effective amount to treat rheumatoid arthritis.

In a further embodiment, the invention pertains, at least in part, to a method of treating a malignant neoplasm in a subject. The method includes administering to a subject in need thereof, a therapeutically effective amount of a compound of formula (I) in combination with a second agent such that the malignant neoplasm is treated in the subject.

The term "malignant neoplasm" includes neoplasms which can be treated using the compounds of the invention. The malignant neoplasms may include neoplasms which are associated with, caused by, cause, result from, or otherwise related to amyloidosis, e.g., AA amyloidosis. Examples of such malignant neoplasms include, but are not limited to, Hodgkin's lymphoma, renal carcinoma, gut carcinoma, lung carcinoma, urogenital tract carcinoma, basal cell carcinoma, hepatoma, Castleman's disease, Schnitzler's syndrome, Waldenstrom's disease, or hairy cell leukemia.

Examples of second agents which may be useful for the treatment of malignant neoplasms include agents which are known to treat Hodgkin's lymphoma, renal carcinoma, gut carcinoma, lung carcinoma, urogenital tract carcinoma, basal cell carcinoma, or hairy cell leukemia. Further examples of second agents which may be used include chemotherapeutic or cytotoxic agents.

In a further embodiment, the therapeutically effective amount of the compound of the invention is effective to treat, prevent or delay the onset of AA amyloidosis and the second agent is administered in an effective amount to treat malignant neoplasm.

In yet another embodiment, the invention pertains to methods of treating chronic infections. The methods include administering to a subject in need thereof, a therapeutically effective amount of a compound of formula (I) in combination with a second agent such that the chronic infection is treated.

The term "chronic infections" includes chronic viral, bacterial, fungal, and microbial infections which can be treated using the compounds of the invention. The infections may include infections which are associated with, cause, caused by, result from, or otherwise related to amyloidosis, e.g., AA amyloidosis. The microbial infections may be local or systemic. Examples of such microbial infections include, but are not limited to, acne conglobata, common variable immunodeficiency, hypolagammaglobulinemia, cystic fibrosis, leprosy, tuberculosis, bronchiectasis, decubitus ulcers, pyelonephritis, osteomyelitis, pulmonary tuberculosis, pulmonary infection(s), recurrent abscesses, Behcet's disease, and Whipple's disease. Other chronic infections include AIDS, HIV, hepatitis B, and hepatitis C.

Examples of second agents which may be useful for the treatment of infections include agents which are known to treat AIDS, HIV, hepatitis B, hepatitis C, leprosy, tuberculosis, bronchiectasis, decubitus ulcers, pyelonephritis, osteomyelitis, acne conglobata, common variable immunodeficiency, hypolagammaglobulinemia, cystic fibrosis, pulmonary tuberculosis, pulmonary infection(s), recurrent abscesses, Behcet's disease, or Whipple's disease. Examples of agents which may be administered to the subject include, for example, anti-inflammatory agents and antibiotic agents.

In a further embodiment, the therapeutically effective amount of the compound of the invention is effective to treat, prevent or delay the onset of AA amyloidosis and the second agent is administered in an effective amount to treat the chronic infection.

In yet another embodiment, the invention pertains, at least in part, to a method of increasing the oral bioavailability of a compound in a subject, by administering to a subject a therapeutically effective amount of the compound of formula (I) in a pharmaceutical composition without food such that the oral bioavailability of the compound in the subject is increased.

The term "oral bioavailability" refers to the quantity of drug reaching the bloodstream after oral administration. The term "increased oral bioavailability" refers to an increase in the bioavailability of about 5% or greater, about 10% or greater, about 15% or greater, about 20% or greater, about 25% or greater, about 30% or greater, about 35% or greater, about 40% or greater, about 50% or greater, about 55% or greater, about 60% or greater, about 65% or greater, about 70% or greater, about 75% or greater, about 80% or greater, about 85% or greater, about 90% or greater, about 95% or greater, or about 100% or greater.

In a further embodiment, the administration of the compound of the invention without food results in an increase in the maximal plasma concentration ($C_{max}$) and extent of absorption (AUC) of the compound as compared to administration with food. The increase of the $C_{max}$ and/or the AUC may be about 5% or greater, about 10% or greater, about 15% or greater, about 20% or greater, about 25% or greater, about 30% or greater, about 35% or greater, about 40% or greater, about 50% or greater, about 55% or greater, about 60% or greater, about 65% or greater, about 70% or greater, about 75% or greater, about 80% or greater, about 85% or greater, about 90% or greater, about 95% or greater, or about 100% or greater as compared to administration of the compound with food. In a further embodiment, the subject is informed (e.g., by instructions by a physician or pharmacist, or by a label or insert accompanying the compound of the invention) that the administration results in an increase in the maximal plasma concentration ($C_{max}$) and extent of absorption (AUC) of the compound as compared to administration with food.

The term "without food" refers to the administration of a medication or a composition of the present invention on a substantially empty stomach. Accordingly, in some embodiments, administration without food includes administration more than 15 minutes, 30 minutes, 60 minutes, 90 minutes, 120 minutes, 150 minutes, 3 hours, 4 hours, 5 hours, 6 hours, 7 hours or 8 hours after the most recent consumption of food. In other embodiments, administration without food includes administration at least 15 minutes, 30 minutes, 60 minutes, 90 minutes, 120 minutes, 150 minutes, 3 hours, 4 hours, 5 hours, 6 hours, 7 hours or 8 hours before the next consumption of food. In one embodiment, the term "without food" is administration of the compound of the invention at least one hour before a meal or at least two hours after a meal. In this embodiment, the term "about" includes values ±10-20% of the indicated period.

In another embodiment, the invention pertains to a method of reducing the rate of progression of nephropathy in a subject in need thereof, as measured by, e.g., the occurrence of a doubling of serum creatinine, greater than or equal to a 50% decrease in creatinine clearance, dialysis/end-stage renal disease, and/or all-cause mortality. The may, for example, have AA amyloidosis, rheumatoid arthritis, chronic inflammation, chronic infection, hereditary fever, etc.

In another embodiment, the invention pertains to a method for preventing or delaying progression to End Stage Renal Disease (ESRD) and/or dialysis in a subject having AA amyloidosis. The method includes administering to the subject a therapeutically effective amount of a compound of formula (I), such that progression to ESRD and/or dialysis is delayed or prevented.

In a further embodiment, the progression to ESRD and/or dialysis is delayed by 1 month or longer, 2 months or longer, 3 months or longer, 4 months or longer, 5 months or longer, 6 months or longer, 7 months or longer, 8 months or longer, 9 months or longer, 10 months or longer, or 12 months or longer. In yet a further embodiment, dialysis and/or ESRD is delayed six months as compared to a standard subject with a similar disorder who has not been treated with the compound of the invention.

In another embodiment, the risk of progressing to ESRD is reduced by about 0-78%. In another embodiment, the risk is decreased by about 5%, by about 10%, by about 15%, by about 20%, by about 25%, by about 30%, by about 35%, by about 40%, by about 45%, by about 50%, by about 55%, by about 60%, by about 65%, by about 70%, by about 75%, or by about 78%. In this embodiment, the term "about" includes values ±5%.

In a further embodiment, the median time to dialysis is delayed by at least about 1 month, about 2 months, about 3 months, about 4 monrths, about 5 months, about 6 months, about 7 months, about 8 months, or about 9 months. In this embodiment, the term "about" includes the range of ±0.5 months of the indicated period. In a further embodiment, the median time to dialysis is 3.5 months ±5.5, or up to 9 months longer in subjects with a compound of formula (I), e.g., PDS.

In a further embodiment, the invention pertains, at least in part, to a method for preventing or delaying the time to the doubling of serum creatinine in a subject having AA amyloidosis. The method includes administering to the subject a therapeutically effective amount of a compound of formula (I), such that the time to the doubling of serum creatinine is delayed or prevented.

In a further embodiment, the invention includes a method for preventing or delaying the time to at least 50% decrease in creatinine clearance in a subject having AA amyloidosis. The method includes administering to the subject a therapeutically effective amount of a compound, such that the time to the at least 50% decrease in creatinine clearance is delayed or prevented. In a further embodiment, the median time to at least a 50% decrease in creatinine clearance is about 1 month, about 2 months, about 3 months, about 4 monrths, about 5 months, about 6 months, about 7 months, about 8 months, about 9 months, about 10 months, about 11 months or about 12 months in subjects treated with compounds of formula (I), such as PDS. In this embodiment, the term "about" includes the range of ±0.5 months of the indicated period. In a further embodiment, the median time to at least a 50% decrease in creatinine clearance is up to 12 months longer in PDS treated patients.

In a further embodiment, the time to doubling of serum creatinine and/or the at least 50% decrease in creatinine clearance is delayed by 1 month or longer, 2 months or longer, 3 months or longer, 4 months or longer, 5 months or longer, 6 months or longer, 7 months or longer, 8 months or longer, 9 months or longer, 10 months or longer, or 12 months or longer. In another embodiment, the 50% decrease in creatinine clearance is delayed about 3 to about 5 months, or about 4 months. In yet a further embodiment, the doubling of serum creatinine and/or the at least 50% decrease in creatinine clearance is delayed at least about six months as compared to standard subject with a similar disorder who has not been treated with the compound of the invention. In a further embodiment, the time to the doubling of serum creatinine is delayed by about 3 months to about 5 months, or about 4 months.

In yet another embodiment, the invention includes a method for decreasing the time to at least 50% increase in creatinine clearance in a subject having AA amyloidosis. The method includes administering to the subject a therapeutically effective amount of a compound of formula (I), such that the time to the at least 50% increase in creatinine clearance is decreased.

In a further embodiment, the time to an at least 50% increase in creatinine clearance is decreased by 1 month or longer, 2 months or longer, 3 months or longer, 4 months or longer, 5 months or longer, 6 months or longer, 7 months or longer, 8 months or longer, 9 months or longer, 10 months or longer, or 12 months or longer. In yet a further embodiment, the at least 50% increase in creatinine clearance is decreased six months as compared to standard subject with a similar disorder who has not been treated with the compound of the invention.

In another further embodiment, the invention includes a method for reducing the rate of progression of renal disease as measured by the slope of creatinine clearance in a subject having AA amyloidosis. The method includes administering to the subject a therapeutically effective amount of a compound of formula (I), such that the rate of progression of renal disease is reduced, as measured, e.g., by a decline in the rate of decrease of creatinine clearance.

In a further embodiment, the slope of creatinine clearance is reduced by about 0-10 mL/min/1.73 m$^2$/year. In another further embodiment, the slope of creatine clearance is reduced by about 1 mL/min/1.73 m$^2$/year, by about 2 mL/min/1.73 m$^2$/year, by about 3 mL/min/1.73 m$^2$/year, by about 4 mL/min/1.73 m$^2$/year, by about 5 mL/min/1.73 m$^2$/year, by about 6 mL/min/1.73 m$^2$/year, by about 7 mL/min/1.73 m$^2$/year, by about 8 mL/min/1.73 m$^2$/year, by about 9 mL/min/1.73 m$^2$/year, or by about 10 mL/min/1.73 m$^2$/year. In a further embodiment, the slope of creatinine clearance is reduced by about 4.7±5 mL/min/1.73 m$^2$/year. In this embodiment, the term "about" includes values ±0.5 mL/min/1.73 m$^2$/year.

In a further embodiment, the rate of progression of renal disease is reduced by about 10% or greater, about 20% or greater, about 30% or greater, about 40% or greater, about 50% or greater, or about 60% or greater. In a particular embodiment, the rate of progression of renal disease is reduced by about 30% to about 40%.

The language "rate of change of creatinine clearance" refers to the rate of change in creatinine clearance normalized for a subject's body surface area over time. For example, a subject's creatinine clearance can be measured through, for example, a 24 hr urine collection at designated time points. This creatinine clearance is normalized for body surface area and the least-squares estimate of the within-subject slope may be calculated using available creatinine clearance measurements for that subject. Generally, the slope of creatinine clearance is expressed as an annual rate of change. A suitable transformation (i.e. log transformation) may be applied, if necessary, prior to the slope calculation.

In a further embodiment, the rate of change of a subject's creatinine clearance is improved by about 1 mL/min/year or more; about 2 mL/min/year or more; about 3 mL/min/year or more; about 4 mL/min/year or more; about 5 mL/min/year or more; about 6 mL/min/year or more; about 7 mL/min/year or more; about 8 mL/min/year or more; about 9 mL/min/year or more; or about 10 mL/min/year or more. In a further embodiment, the decrease in the rate of the creatinine clearance is lessened by about 2 to about 5 mL/min/year.

In a further embodiment, the invention pertains, at least in part, to a method for stabilizing or reducing proteinuria in a subject having AA amyloidosis. The method includes administering to the subject a therapeutically effective amount of a compound of formula (I), such that the proteinuria in the subject is stabilized or reduced. In one embodiment, the proteinuria is reduced by about 0.5 g/24 hours or more; about 1 g/24 hours; about 1.5 g/24 hours; or by about 2 g/24 hours. In one embodiment, the proteinuria is stabilized at below or equal to 1 g/24 hours.

In another embodiment, the invention pertains, at least in part, to a method for stabilizing renal function or delaying progression of renal disease in a subject having AA amyloidosis. The method includes administering to the subject a therapeutically effective amount of a compound of formula (I), such that the subject's renal function is stabilized or the progression of renal disease is delayed.

In a further embodiment, the progression of renal disease is delayed by 1 month or longer, 2 months or longer, 3 months or longer, 4 months or longer, 5 months or longer, 6 months or longer, 7 months or longer, 8 months or longer, 9 months or longer, 10 months or longer, or 12 months or longer.

In yet another embodiment, the invention pertains to a method for treating renal impairment in a subject having AA amyloidosis. The method includes administering to the subject a therapeutically effective amount of a compound of formula (I), such that the renal impairment is treated.

In another embodiment, the invention pertains, at least in part, to a method for preventing or delaying progression to nephrotic syndrome in a subject having AA amyloidosis. The method includes administering to the subject a therapeutically effective amount of a compound of Formula (I), e.g. 1,3-propanedisulfonic acid or a pharmaceutically acceptable salt thereof, e.g. a disodium salt, such that progression to nephrotic syndrome is prevented or delayed.

In another embodiment, the invention pertains, at least in part, to a method for treating nephrotic syndrome in a subject having AA amyloidosis. The method includes administering to the subject a therapeutically effective amount of a compound of Formula (I), e.g. 1,3-propanedisulfonic acid or a pharmaceutically acceptable salt thereof, e.g. a disodium salt, such that the parameters associated with nephrotic syndrome are improved or nephrotic syndrome is remitted.

In another embodiment, the invention pertains, at least in part, to a method for sustaining remission of nephrotic syndrome in a subject having AA amyloidosis. The method includes administering to the subject a therapeutically effective amount of a compound of Formula (I), e.g. 1,3-propanedisulfonic acid or a pharmaceutically acceptable salt thereof, e.g. a disodium salt, such that remission of nephrotic syndrome is sustained over a period of, e.g., about 4, 6, 8, 10 or 12 months. In a particular embodiment, remission of nephrotic syndrome is sustained in a patient over a period of about 6 to about 8 months.

In another embodiment, the invention pertains, at least in part, to a method for stabilizing or increasing GFR in a subject having AA amyloidosis. The method includes administering to the subject a therapeutically effective amount of a compound of Formula (I), e.g. 1,3-propanedisulfonic acid or a pharmaceutically acceptable salt thereof, e.g. a disodium salt, such that GFR is stabilized or increased.

The terms "glomerular filtration rate" and "GFR" are used interchangably herein and are an indicator of kidney function. One measure of a subject's GFR, for example, is the rate of creatinine clearance. Renal function and/or GFR can be assessed using a number of criteria, such as, for example: serum creatinine levels, urinary creatinine levels, urinary albumin levels, urinary microproteins levels (e.g. retinol binding protein, N-acetyl-β-D-glucosaminidase, microalbumin, etc.), plasma clearance of inulin, creatinine clearance, proteinurea, etc.

Furthermore, a subject may have mild, moderate or severe renal impairment. For example, a healthy subject typically has a GFR of greater than about 100 mL/min. A subject with "mild" renal impairment may, for example, have a GFR of about 50 to about 80 mL/min or a GFR of less than 100, or a creatinine clearance rate of about 60 to about 90 mL/min. A subject with "moderate" renal impairment may, for example, have a GFR of about 30 to about 50 mL/min, or a creatinine clearance rate of about 30 to about 60 mL/min. A subject with "severe" renal impairment may, for example, have a GFR of less than about 30 mL/min, or a creatinine clearance rate of about 15 to about 30 mL/min. Subjects may also be classified as mild, moderate or severe as described in the examples herein, or using criteria known in the art (see, e.g., McCullough, P. A., Rev. Cardiovasc. Med. 2003;4(suppl. 1): S2-S6; K/DOQI guidelines at www.kidney.org/professionals).

In other embodiments, a subject may have a creatine clearance rate, before treatment (e.g., at baseline) of about 50 to about 120 mL/min, about 60 to about 100 ml/min, about 70 to about 110 ml/min, or about 70 to about 100 ml/min.

In a further embodiment, the subject is nephrotic. In another further embodiment, the subject is non-nephrotic. The subject may be suffering from a disorder such as, for example, an inflammatory disorder, a malignant neoplasm, or a chronic infection.

B. Compounds Of The Invention

In an embodiment, the invention pertains to compounds of formula (I):

$$Y-(CH_2)_n-[CH_2Y]_m \qquad (I)$$

wherein Y is $SO_3X$ or $OSO_3X$ independently chosen for each occurrence; X is cationic group independently chosen for each occurrence; n is 1, 2, 3 or 4; m is 1 or 2, provided that when m is 2, one hydrogen of the $-(CH_2)_n-$ group is absent.

The term "cationic group" includes groups with a positive charge and hydrogen atoms. Examples of cations include pharmaceutically acceptable salts of the $SO_3^-$ or $OSO_3^-$. Examples of cationic groups include ions of alkali or alkaline earth metals, such as lithium, sodium, potassium, calcium, magnesium, and aluminum and the like. In a further embodiment, the cationic groups are $H^+$ or $Na^+$.

Examples of compounds of the invention include the compounds below and pharmaceutically acceptable salts thereof.

| | |
|---|---|
| 1,2-Ethanedisulfonic acid | $HO_3SCH_2CH_2SO_3H$ |
| Sodium 1,2-ethanedisulfonate | $NaO_3SCH_2CH_2SO_3NA$ |
| 1,3-propanedisulfonic acid | $HO_3SCH_2CH_2CH_2SO_3H$ |
| Sodium 1,3-propanedisulfonate (1,3-propanedisulfonic acid, disodium salt) | $NaO_3SCH_2CH_2CH_2SO_3Na$ |
| 1,2-Ethanediol bis(hydrogen sulfate) | $HO_3SOCH_2CH_2OSO_3H$ |
| 1,2-Ethanediol disulfate, disodium salt | $NaO_3SOCH_2CH_2OSO_3Na$ |
| 1,3-Propanediol bis(hydrogen sulfate) | $HO_3SOCH_2CH_2CH_2OSO_3H$ |
| 1,3-Propanediol disulfate, disodium salt | $NaO_3SOCH_2CH_2CH_2OSO_3Na$ |
| 2-Sulfomethyl-1,4-butanedisulfonic acid | $HO_3SCH_2CH_2CH(CH_2SO_3H)_2$ |
| 2-Sulfomethylbutane-1,4-disulfonic acid, trisodium salt | $NaO_3SCH_2CH_2CH(CH_2SO_3Na)_2$ |

In one embodiment, the compound or anti-amyloidogenic agent is not 1,3-propanedisulfonic acid disodium salt or 1,3-propanedisulfonic acid. In another embodiment, the compound or anti-amyloidogenic agent is not 1,3-propanedisulfonic acid disodium salt.

The term "compound" includes chemical entities. The compounds may be in solid, liquid or gaseous phase. The term compound includes the compounds of formula (I) and pharmaceutically acceptable salts thereof. Compounds of the invention are identified herein by their chemical structure and/or chemical name. Where a compound is referred to by both a chemical structure and a chemical name, and that chemical structure and chemical name conflict, the chemical structure is determinative of the compound's identity. The compounds of the invention may contain a chiral center and, therefore, may exist as stereoisomers. Compounds, as defined herein, may be purified from natural sources, purchased from commercial sources or chemically synthesized using art recognized techniques.

In addition, the compounds of the invention also may exist in hydrated and anhydrous forms. Hydrates of the compound of formula (I) are included as compounds of formula (I). In a further embodiment, the compound of formula (I) is a monohydrate. In one embodiment, the compound of formula (I) comprises about 10% or less, about 9% or less, about 8% or less, about 7% or less, about 6% or less, about 5% or less, about 4% or less, about 3% or less, about 2% or less, about 1% or less, about 0.5% or less, about 0.1% or less by weight of water. In another embodiment, the compounds of the invention comprise, about 0.1% or more, about 0.5% or more, about 1% or more, about 2% or more, about 3% or more, about 4% or more, about 5% or more, or about 6% or more by weight of water.

In addition, the compounds of the invention may also encompass more than one polymorphic forms, hydrated states, etc. For example, one form, Form I, can be prepared by direct recrystallization of a compound of the invention, e.g., 1,3-propanedisulfonic acid, disodium salt. The compound is precipitated from solution with 16:1 ethanol:water (v/v). The recrystallized product is recovered as a fine white powder which is then dried at 65° C. for 16 hours at 4 mm Hg. The resulting non-hydrated form has a moisture content of 0.2% and an apparent density of 0.64 g/ml. In a further embodiment, the compound of formula (I) has a moisture content of about 0.2%.

Furthermore, another form, Form II, can be prepared by direct recrystallization of a commercially available 1,3-propanedisulfonic acid, disodium salt in a fashion similar to Form I. The compound is precipitated from solution with 8:1 ethanol:water (v/v). The recrystallized product is recovered as a white solid which is then dried at 20-25° C. for 16 hours at 4 mm Hg. The resulting mono-hydrated form has a moisture content of about 7% w/w and an apparent density of 0.46 g/ml. In a further embodiment, the compound of formula (I) has a moisture content of about 7%.

Form I can be also be prepared from the Form II polymorph by prolonged heating at reduced pressures. First, the Form II polymorph (water content 6.8%) is dried at 65° C. for 16 hours in a vacuum at 4 mm Hg. This initial drying reduces the water content of the formerly hydrated polymorph to 2.3%. After another 24 hours at 65° C., the moisture content of the formerly monohydrated polymorph is reduced to 1%. The compound is entirely converted to Form I polymorph only after an additional 48 hours of drying at 77° C.

The compounds of the present invention contain one or more acidic functional groups and, thus, are capable of forming pharmaceutically acceptable salts with pharmaceutically acceptable bases. The term. "pharmaceutically acceptable salts" in these instances refers to the relatively non-toxic, inorganic and organic base addition salts of compounds of the present invention.

These salts can likewise be prepared in situ during the final isolation and purification of the agents, or by separately reacting the purified agent in its free acid form with a suitable base, such as the hydroxide, carbonate or bicarbonate of a pharmaceutically acceptable metal cation, with ammonia, or with a pharmaceutically acceptable organic primary, secondary or tertiary amine. Representative alkali or alkaline earth salts include the lithium, sodium, potassium, calcium, magnesium, and aluminum salts and the like. Representative organic amines useful for the formation of base addition salts include ethylamine, diethylamine, ethylenediamine, ethanolamine, diethanolamine, piperazine and the like.

"Pharmaceutically acceptable salts" also includes, for example, derivatives of agents modified by making base salts thereof, as described further below and elsewhere in the present application. Examples of pharmaceutically acceptable salts include alkali or organic salts of acidic residues such as sulfonates. Pharmaceutically acceptable salts include the conventional non-toxic salts or the quaternary ammonium salts of the parent agent formed, for example, from non-toxic inorganic or organic acids. Such conventional non-toxic salts include those derived from inorganic acids such as hydrochloric, hydrobromic, sulfuric, sulfamic, phosphoric, and nitric acid; and the salts prepared from organic acids such as acetic, propionic, succinic, glycolic, stearic, lactic, malic, tartaric, citric, ascorbic, palmoic, maleic, hydroxymaleic, phenylacetic, glutamic, mesylate, benzoic, salicylic, sulfanilic, 2-acetoxybenzoic, fumaric, toluenesulfonic, methanesulfonic, ethane disulfonic, oxalic, and isethionic acid. Pharmaceutically acceptable salts may be synthesized from the parent agent which contains a basic or acidic moiety by conventional chemical methods. Generally, such salts may be prepared by reacting the free acid or base forms of these agents with a stoichiometric amount of the appropriate base or acid in water or in an organic solvent, or in a mixture of the two.

All acid, salt, base, and other ionic and non-ionic forms of the compounds described are included as compounds of the invention. For example, if a compound is shown as an acid herein, the salt forms of the compound are also included. Likewise, if a compound is shown as a salt, the acid and/or basic forms are also included.

In a further embodiment, the compound of formula (I) is not 1,3-propanedisulfonic acid disodium salt or 1,3-propanedisulfonic acid.

C. Formulations Of The Invention

In another embodiment, the invention pertains to a pharmaceutical formulation for treating AA amyloidosis, comprising a therapeutically effective amount of a compound of formula (I) in a formulation such that the formulation has at least one favorable biological property (FBP) upon administration to a subject.

The term "pharmaceutical formulation" includes pharmaceutical compositions as described below. In a further embodiment, the pharmaceutical formulations are designed to have favorable biological properties which enhance the ability of the compounds of the invention to treat AA amyloidosis and/or amyloid related diseases. The favorable biological properties of the formulation were discovered by administering the compounds of the invention to subjects during clinical trials.

The term "favorable biological property" includes biological properties other than the ability of the compound of the invention to inhibit AA amyloidosis and/or treat an amyloid related disease, which enhance the ability of the compound of the invention to perform its intended function, e.g., treat AA amyloidosis and/or an amyloid related disease. In one embodiment, the favorable biological properties can be a pharmacokinetic profile. Examples of such parameters which may be used, include, but are not limited to $C_{max}$, $C_{ss}$, $T_{max}$, $AUC_{0-t}$, $AUC_\infty$, and $T_{1/2}$. These parameters ($C_{max}$, $T_{max}$, $AUC_{0-t}$, $AUC_\infty$ and $T_{1/2}$ may be derived, for example, by non-compartmental analysis using WinNonlin® (Pharsight Corporation, Mountain View, Calif.) or SAS® for Windows® (SAS Institute Inc., Cary, N.C.). In a further embodiment, the favorable biological property is a target plasma concentration or a target systemic exposure.

The term "$C_{max}$" refers to the maximum observed plasma concentration of the compound of the invention in a particular subject.

The term "$C_{ss}$" refers to the steady state plasma concentration of the compound of the invention in a particular subject.

The term "$T_{max}$" refers to the time of the occurrence of the $C_{max}$.

The term "$AUC_{0-t}$" refers to the area under the plasma concentration versus time curve from time zero to the last sampling time at which concentrations were at or above the limit of quantification, calculated by the linear trapezoidal rule.

The term "$AUC_\infty$" refers to the area under the plasma concentrations versus time curve from time zero to infinity, calculated from $AUC_{0-t}+(C_{last}/\lambda_z)$, where $C_{last}$ is the last observed quantifiable concentration and $\lambda z$ is the apparent terminal rate constant.

The term "$T_{1/2}$" refers to the apparent terminal half-life, calculated from ln $2\lambda_z$.

The invention also includes formulations and compositions which combine two or more favorable biological properties, such as pharmacokinetic parameters or combinations thereof. Examples of these pharmacokinetic parameters include $AUC_{0-t}$, $AUC_\infty$, $C_{max}$ and/or $T_{max}$. For example, the formulations of the invention may be selected such that when administered to a healthy subject (or one without renal impairment), the selected formulation provides the subject with one or more of the desired pharmacokinetic parameters. Alternatively, the formulations of the invention may be selected such that when administered to a subject with impaired renal function and/or subjects with AA amyloidosis or at risk for AA amyloidosis, the selected formulation provides the subject with one or more of the desired pharmacokinetic parameters.

In a further embodiment, the formulation is not as described in Example 7. In another further embodiment, at least one ingredient is not an ingredient described in Example 7.

In another further embodiment, the formulation has a diluent that is not lactose monohydrate. Examples of diluents that are not lactose monohydrate include, for example, sugars (e.g., glucose, sucrose, fructose, etc.), starches (e.g., corn starch, potato starch, etc.), cellulose, derivatives of cellulose (e.g., sodium carboxymethyl cellulose, ethyl cellulose, cellulose acetate, etc.), powdered tragacanth, malt, gelatin, talc, and mixtures thereof. In another further embodiment, the hygroscopicity of the diluent and/or lubricant is selected such that the resulting capsules are acceptable under FDA regulations.

In another further embodiment, the formulation has a lubricant that is not magnesium stearate. Examples of lubricants that are not magnesium stearate include, for example, stearic acid powder, talc, calcium stearate, polyethylene glycol, sodium lauryl sulfate, and mixtures thereof.

In another embodiment, the formulation comprises less than about 0.5% (w/w) of any single known impurity, less than about 1.5% (w/w) of total sulfates, less than about 0.1% (w/w) total unknown impurities, and less than about 5.0% (w/w) impurities overall.

In another embodiment, the compound of formula (I) conforms to a reference standard IR (Infrared) spectra and/or IC (ion chromatography) of 1,3-propanedisulfonic acid disodium salt or 1,3-propanedisulfonic acid. In another embodiment, the compound of formula (I) comprises less than about 1.0% w/w of water. In yet another embodiment, the compound of formula (I) less than about 20 ppm of heavy metals and/or less than about 0.5% w/w residual solvent.

In another embodiment, the invention pertains to a biologically favorable formulation for treating AA amyloidosis, comprising an anti-amyloidogenic agent in a formulation such that the anti-amyloidogenic agent-containing formulation is equivalent to a standard formulation predetermined to have at least one favorable biological property upon administration to a subject such that it is a biologically favorable formulation.

The term "biologically favorable formulation" refers to a pharmaceutical formulation with at least one favorable biological property. In a further embodiment, the formulation has two or more, three or more, or four or more biologically favorable properties. In one embodiment, the biologically favorable formulation is formulated such that a target plasma concentration of the compound of the invention is reached in the subject 30 minutes or less, one hour or less, two hours or less, or five hours or less after administration of the compound to a subject.

In one embodiment, the biologically favorable formulation is selected based on a subject's creatinine clearance rate in order to achieve a particular $AUC_{ss}$, and/or $C_{ss}$.

For example, the favorable biological property may be an $AUC_{ss}$, of about 5000 ng·h/mL or above, about 6000 ng·h/mL or above; about 6500 ng·h/mL or above; about 7000 ng·h/mL or above; about 8000 ng.h/mL or above; about 9000 ng.h/mL or above; about 10,000 ng.h/mL or above; about 11,000 ng.h/mL or above; about 12,000 ng.h/mL or above; about 13,000 ng.h/mL or above; about 14,000 ng.h/mL or above; about 15,000 ng.h/mL or above; about 16,000 ng.h/mL or above; about 17,000 ng.h/mL or above; about 18,000 ng.h/mL or above; about 19,000 ng.h/mL or above; about 20,000 ng.h/mL or above; about 21,000 ng.h/mL or above; about 22,000 ng.h/mL or above; about 23,000 ng.h/mL or above; about 24,000 ng.h/mL or above; or about 25,000 ng.h/mL or above. In another embodiment, the favorable biological property is an $AUC_{ss}$ of about 7000 ng·h/mL; about 8000 ng.h/mL or less; about 9000 ng.h/mL or less; about 10,000 ng.h/mL or less; about 11,000 ng.h/mL or less; about 12,000 ng.h/mL or less; about 13,000 ng.h/mL or less; about 14,000 ng.h/mL or less; about 15,000 ng.h/mL or less; about 16,000 ng.h/mL or less; about 17,000 ng.h/mL or less; about 18,000 ng.h/mL or less; about 19,000 ng.h/mL or less; about 20,000 ng.h/mL or less; about 21,000 ng.h/mL or less; about 22,000 ng.h/mL or less; about 23,000 ng.h/mL or less; about 24,000 ng.h/mL or less; about 25,000 ng.h/mL or less, or about 26,000 ng.h/mL or less.

The biologically favorable property may be a desirable steady state concentration ($C_{ss}$). For example, the favorable biological property may be a $C_{ss}$ of about 500 ng/mL or above, about 600 ng/mL or above; about 700 ng/mL or above; about 800 ng/mL or above; about 900 ng/mL or above; about 950 or above ng/mL; about 1000 ng/mL or above; about 1100 ng/mL or above; or about 1200 ng/mL. In addition, the biologically favorable property may be a $C_{ss}$ of about 1200 ng/mL or less, about 1100 ng/mL or less; about 1000 ng/mL or less; about 900 ng/mL or less; about 800 ng/mL or less; about 700 ng/mL or less; about 600 ng/mL or less; or less than about 500 ng/mL.

In another embodiment, the favorable biological property may be a $C_{max}$ (after a single oral administration of the compound) of about 250 to about 2000 ng/mL. In a further embodiment, the $C_{max}$ is about 250 ng/mL or greater; about 300 ng/mL or greater; about 350 ng/mL or greater; about 400 ng/mL or greater; about 500 ng/mL or greater; about 600 ng/mL or greater; about 700 ng/mL or greater; about 800 ng/mL or greater; about 900 ng/mL or greater; about 1000 ng/mL or greater; about 1100 ng/mL or greater; about 1200 ng/mL or greater; about 1300 ng/mL or greater; about 1400 ng/mL or greater; about 1500 ng/mL or greater; about 1600 ng/mL or greater; about 1700 ng/mL or greater; about 1800 ng/mL or greater; about 1900 ng/mL or greater; or about 2000 ng/mL or greater. The term "about" in this embodiment, includes values ±50 ng/mL of the indicated range.

In a further embodiment, the $C_{max}$ after administration of a single oral dose is about 850 ng/mL; about 1700 ng/mL or less; about 1600 ng/mL or less; about 1500 ng/mL or less; about 1400 ng/mL or less; about 1300 ng/mL or less; about 1200 ng/mL or less; about 1000 ng/mL or less; about 900 ng/mL or less; about 800 ng/mL or less; about 700 or less; about 700 ng/mL or less; about 500 ng/mL or less; about 400 ng/mL or less; or about 300 ng/mL or less. In another embodiment, the $C_{max}$ is at least 200 ng/mL after administration of a single oral dose of the compound. The term "about" in this embodiment, includes values ±50 ng/mL of the indicated range.

In another embodiment, the favorable biological property may be a $C_{max}$ (after multiple oral administrations of the compound) of about 400 to about 3800 ng/mL. In a further embodiment, the $C_{max}$ is about 400 ng/mL or greater; about 500 ng/mL or greater; about 600 ng/mL or greater; about 700 ng/mL or greater; about 800 ng/mL or greater; about 900 ng/mL or greater; about 1000 ng/mL or greater; about 1100 ng/mL or greater; about 1200 ng/mL or greater; about 1300 ng/mL or greater; about 1400 ng/mL or greater; about 1500 ng/mL or greater; about 1600 ng/mL or greater; about 1700 ng/mL or greater; about 1800 ng/mL or greater; about 1900 ng/mL or greater; about 2000 ng/mL or greater; about 2100 ng/mL or greater; about 2200 or greater; about 2300 ng/mL or greater; about 2400 ng/mL or greater; about 2500 ng/mL or greater; about 2600 ng/mL or greater; about 2700 ng/mL or greater; about 2800 ng/mL or greater; about 2900 ng/mL or greater; about 3000 ng/mL or greater; about 3100 ng/mL or greater; about 3200 or greater; about 3300 ng/mL or greater; about 3400 ng/mL or greater; about 3500 ng/mL or greater; about 3600 ng/mL or greater; about 3700 ng/mL or greater; about 3800 ng/mL or greater; or about 3900 ng/mL or greater. The term "about" in this embodiment, includes values+50 ng/mL of the indicated range.

In a further embodiment, the $C_{max}$ (after multiple oral administrations) is about 500 to about 3900 ng/ml. In a further embodiment, the $C_{max}$ is about 500 ng/ml or less, about 600 ng/ml or less; about 700 ng/ml or less; about 900 ng/ml or less; about 1000 ng/mL or less; about 1100 ng/mL or less; about 1200 ng/mL; about 1300 ng/mL or less; about 1400 ng/mL or less; about 1500 ng/mL or less; about 1600 ng/mL or less; about 1700 ng/mL or less; about 1800 ng/mL or less; about 1900 ng/mL or less; about 2000 ng/mL or less; about 2100 ng/mL or less; about 2200 or less; about 2300 ng/mL or less; about 2400 ng/mL or less; about 2500 ng/mL or less; about 2600 ng/mL or less; about 2700. ng/mL or less; about 2800 ng/mL or less; about 2900 ng/mL or less; about 3000 ng/mL or less, about 3100 ng/mL or less; about 3200 or less; about 3300 ng/mL or less; about 3400 ng/mL or less; about 3500 ng/mL or less; about 3600 ng/mL or less; about 3700 ng/mL or less; about 3800 ng/mL or less; or about 3900 ng/mL or less. The term "about" in this embodiment, includes values ±50 ng/mL of the indicated range.

For example, the favorable biological property may be an $AUC_\infty$ of about 2000 ng·h/mL or above, about 3000 ng·h/mL or above, about 4000 ng·h/mL or above, about 5000 ng·h/mL or above, about 6000 ng·h/mL or above; about 6500 ng·h/mL or above; about 7000 ng·h/mL or above; about 8000 ng.h/mL or above; about 9000 ng.h/mL or above; about 10,000 ng.h/mL or above; about 11,000 ng.h/mL or above; about 12,000 ng.h/mL or above; about 13,000 ng.h/mL or above; about 14,000 ng.h/mL or above; about 15,000 ng.h/mL or above; about 16,000 ng.h/mL or above; about 17,000 ng.h/mL or above; about 18,000 ng.h/mL or above; about 19,000 ng.h/mL or above; about 20,000 ng.h/mL or above; about 21,000 ng.h/mL or above; about 22,000 ng.h/mL or above; about 23,000 ng.h/mL or above; about 24,000 ng.h/mL or above; about 25,000 ng.h/mL or above; about 26,000 ng.h/mL or above; about 27,000 ng.h/mL or above; about 28,000 ng.h/mL or above; about 29,000 ng.h/mL or above; about 30,000 ng.h/mL or above; about 31,000 ng.h/mL or above; about 32,000 ng.h/mL or above; about 33,000 ng.h/mL or above; about 34,000 ng.h/mL or above; about 35,000 ng.h/mL or above; about 36,000 ng.h/mL or above; about 37,000 ng.h/mL or above; about 38,000 ng.h/mL or above; about 39,000 ng.h/mL or above; about 40,000 ng.h/mL or above; about 41,000 ng.h/mL or above; about 42,000 ng.h/mL or above; about 43,000 ng.h/mL; about 44,000 ng.h/mL or above; about 45,000 ng.h/mL or above; or about 46,000 ng.h/mL. The term "about" in this embodiment, includes values ±750 ng.h/mL of the indicated range.

In another embodiment, the favorable biological property is an $AUC_\infty$ of about 2000 ng·h/ml; about 3000 ng·h/mL or less, about 4000 ng·h/mL or less, about 5000 ng·h/mL or less, about 5000 ng·h/mL or less, about 6000 ng·h/mL or less; about 6500 ng·h/mL or less; about 7000 ng·h/mL or less; about 8000 ng.h/mL or less; about 9000 ng.h/mL or less; about 10,000 ng.h/mL or less; about 11,000 ng.h/mL or less; about 12,000 ng.h/mL or less; about 13,000 ng.h/mL or less; about 14,000 ng.h/mL or less; about 15,000 ng.h/mL or less; about 16,000 ng.h/mL or less; about 17,000 ng.h/mL or less; about 18,000 ng.h/mL or less; about 19,000 ng.h/mL or less; about 20,000 ng.h/mL or less; about 21,000 ng.h/mL or less; about 22,000 ng.h/mL or less; about 23,000 ng.h/mL or less; about 24,000 ng.h/mL or less; about 25,000 ng.h/mL or less; about 26,000 ng.h/mL or less; about 27,000 ng.h/mL or less; about 28,000 ng.h/mL or less; about 29,000 ng.h/mL or less; about 30,000 ng.h/mL or less; about 31,000 ng.h/mL or less; about 32,000 ng.h/mL or less; about 33,000 ng.h/mL or less; about 34,000 ng.h/mL or less; about 35,000 ng.h/mL or less; about 36,000 ng.h/mL or less; about 37,000 ng.h/mL or less; about 38,000 ng.h/mL or less; about 39,000 ng.h/mL or less; about 40,000 ng.h/mL or less; about 41,000 ng.h/mL or less; about 42,000 ng.h/mL or less; about 43,000 ng.h/mL or less; about 44,000 ng.h/mL or less; about 45,000 ng.h/mL or less; or about 46,000 ng.h/mL or less. The term "about" in this embodiment, includes values ±750 ng.h/mL of the indicated range.

In yet another embodiment, the invention pertains, at least in part, to a pharmaceutical formulation. The pharmaceutical formulation comprises an active agent (e.g., PDS) in an amount effective to treat or prevent AA amyloidosis, and a pharmaceutically acceptable carrier, wherein, when the formulation is orally administered to a healthy subject, a mean plasma concentration profile of the active agent having a mean $AUC_\infty$ of about from 2900 to about 9000 ng·h/mL±20% and a mean $C_{max}$ of about from 450 to about 2150 ng/mL±20% is achieved.

In yet another further embodiment, the invention also pertains, at least in part, to a pharmaceutical formulation, which comprises an active agent (e.g., PDS) in an amount effective to treat or prevent AA amyloidosis, and a pharmaceutically acceptable carrier, wherein, when the formulation is orally administered to a healthy subject, a mean plasma concentration profile of the active agent having a mean $AUC_\infty$ of from about 2,900 to about 9,000 ng·h/mL±20% is achieved.

In yet another further embodiment, the invention pertains to a pharmaceutical formulation, which comprises an active agent (e.g., PDS) in an amount effective to treat or prevent AA amyloidosis, and a pharmaceutically acceptable carrier, wherein, when the formulation is orally administered to a healthy subject, a mean plasma concentration profile of the active agent having a mean $C_{max}$ of about from 450 to about 2150 ng/mL±20% is achieved.

In yet another further embodiment, the invention pertains, at least in part, to a pharmaceutical formulation, comprising an active agent (e.g., PDS), and a pharmaceutically acceptable carrier, wherein, when the formulation is orally administered to a subject having AA amyloidosis: in a dose of 400 mg of the active agent, a mean plasma concentration profile of the active agent having a mean $AUC_\infty$ of about 10,000-12,000 ng·h/mL±20%, and a mean $C_{max}$ of about 800-900 ng/mL±20% is achieved; or in a dose of 800 mg of the active agent, a mean plasma concentration profile of the active agent having a mean $AUC_\infty$ of about 9,000-10,500 ng·h/mL±20%, and a mean $C_{max}$ of about 750-875 ng/mL±20% is achieved; or in a dose of 1200 mg of the active agent, a mean plasma concentration profile of the active agent having a mean $AUC_\infty$ of about 5,000-6,000 ng·h/mL±20%, and a mean $C_{max}$ of about 800-925 ng/mL±20% is achieved.

In yet another further embodiment, the invention also pertains to a pharmaceutical formulation, comprising 800 mgs of an active agent (e.g., PDS), and a pharmaceutically acceptable carrier, wherein, when the formulation is orally administered to a subject: when said subject is healthy, a mean plasma concentration profile of the active agent having a mean $AUC_\infty$ of about 4,000-6,000 ng·h/mL±20%, and a mean $C_{max}$ of about 1,200-1,300 ng/mL±20% is achieved; or when the subject has mild renal impairment, a mean plasma concentration profile of the active agent having a mean $AUC_\infty$ of about 12,000-14,000 ng·h/mL±20%, and a mean $C_{max}$ of about 2,500-3,500 ng/mL±20% is achieved; or when the subject has moderate renal impairment, a mean plasma concentration profile of the active agent having a mean $AUC_\infty$ of about 9,000-11,000 ng·h/mL±20%, and a mean $C_{max}$ of about 2,000-2,200 ng/mL±20% is achieved; or when the subject has severe renal impairment, a mean plasma concentration profile of the active agent having a mean $AUC_\infty$ of about 40,000-46,000 ng·h/mL±20%, and a mean $C_{max}$ of about 2,100-2,300 ng/mL±20% is achieved.

In yet another further embodiment, the invention also pertains, at least in part, to a pharmaceutical formulation, which comprises an active agent (e.g., PDS), and a pharmaceutically acceptable carrier, wherein, when the formulation is orally administered to a subject having AA amyloidosis for twenty-four months: in a dose of 400 mg of the active agent, a mean plasma concentration profile of the active agent having a mean $AUC_\infty$ of about 25,000-26,000 ng·h/mL±20%, and a mean $C_{max}$ of about 2,000-2,300 ng/mL±20% is achieved; or in a dose of 800 mg of the active agent, a mean plasma concentration profile of the active agent having a mean $AUC_\infty$ of about 20,000-22,000 ng·h/mL±20%, and a mean $C_{max}$ of about 1,600-2,000 ng/mL±20% is achieved; or in a dose of 1200 mg of the active agent, a mean plasma concentration profile of the active agent having a mean $AUC_\infty$ of about 8,000-10,000 ng·h/mL±20%, and a mean $C_{max}$ of about 800-1,000 ng/mL±20% is achieved.

In yet another further embodiment, the invention also pertains, at least in part, to a pharmaceutical formulation, comprising an active agent (e.g., PDS), and a pharmaceutically acceptable carrier, wherein, when the formulation is orally administered to healthy male subjects for seven days: in a dose of 400 mg QID of the active agent, a mean plasma concentration profile of the active agent having a mean $AUC_\infty$ of about 10,000-11,500 ng·h/mL±20%, and a mean $C_{max}$ of about 900-1100 ng/mL±20% is achieved; or in a dose of 800 mg QID of the active agent, a mean plasma concentration profile of the active agent having a mean $AUC_\infty$ of about 19,000-21,000 ng·h/mL±20%, and a mean $C_{max}$ of about 1,600-1,800 ng/mL±20% is achieved; or in a dose of 1600 mg TID of the active agent, a mean plasma concentration profile of the active agent having a mean $AUC_\infty$ of about 25,000-27,000 ng·h/mL±20%, and a mean $C_{max}$ of about 4,000-6,000 ng/mL±20% is achieved; or in a dose of 1600 mg QID of the active agent, a mean plasma concentration profile of the active agent having a mean $AUC_\infty$ of about 23,000-25,500 ng·h/mL±20%, and a mean $C_{max}$ of about 4,500-6,500 ng/mL±20% is achieved.

The term "equivalent" refers to a formulation which is considered a bioequivalent or functionally equivalent to a formulation of the invention. In a further embodiment, the formulation is equivalent to a formulation comprising 1,3-propanedisulfonic acid disodium salt or 1,3-propanedisulfonic acid. In a further embodiment, the term includes formulations which meet the definition of bioequivalence under 21 U.S.C. §255 and/or 21 CFR §320. In another embodiment, "equivalent" refers to a formulation which, when administered to a subject, achieves pharmacokinetic parameters, e.g., $C_{max}$, $AUC_\infty$, that are within, for example, ±10%, ±20%, ±30%, or ±40% of the values disclosed herein.

In a further embodiment, the term "equivalent" includes potentially equivalent formulations, wherein the rate and extent of absorption of the potentially equivalent formulation do not show a significant difference, e.g., within ±10%, ±20%, ±30%, or ±40% of the rate and extent of absorption of the standard formulation when administered under similar experimental conditions In another embodiment, the extent of absorption of the potentially equivalent formulation does not show a significant difference, e.g., within ±10%, ±20%, ±30%, or ±40% of the rate and extent of absorption of the standard formulation when administered under similar experimental conditions and the difference from standard formulation is not essential to the attainment of effective body drug concentrations on chronic use, and/or is considered medically insignificant for the drug. In one aspect, the same molar dose may be administered.

The term "standard formulation" refers to a formulation of a compound of formula (I), e.g., 1,3-propanedisulfonic acid disodium salt or 1,3-propanedisulfonic acid, which has at least one favorable biological property. In other embodiments, the standard formulation meets or exceeds the requirements of the drug product specifications. In a further embodiment, the standard formulation is the formulation described in Example 7.

The term "drug product specifications" refers to a formulation wherein the formulation meets U.S. FDA drug product specifications. In a further embodiment, the formulation comprises not more than about 0.5% w/w of any single known impurity, not more than about 1.5% w/w of total sulfates, not more than 0.1% w/w of any single unknown impurity, and not more than about 5.0% w/w total impurities.

The term "anti-amyloidogenic agent" refers to a compound which tests positive in the AA Amyloid Binding Assay (AAABA). In a further embodiment, the anti-amyloidogenic agent binds to AA at a rate of 30% or greater, 45% or greater, 60% or greater, 70% or greater, 80% or greater, or 90% or greater at an AA amyloid concentration of 400 µM as measured in the AAABA. In another embodiment, the anti-amyloidogenic compound binds to AA at a rate of 30% or greater, 45% or greater, 60% or greater, 70% or greater, 80% or greater, or 90% or greater at an AA amyloid concentration of 200 µM, as measured in the AAABA.

The term "anti-amyloidogenic agent" also includes disulfonated compounds and sulfonated alkyl compounds. In a further embodiment, the term includes compounds which are analogs of 1,3-propanedisulfonic acid or a pharmaceutically acceptable salt thereof.

In a further embodiment, the anti-amyloidogenic agent is a compound of formula (I), as described above. Examples of anti-amyloidogenic agents include compounds such as 1,2-ethanedisulfonic acid, sodium 1,2-ethanedisulfonate, 1,2-ethanediol bis(hydrogen sulfate), 1,2-ethanediol disulfate disodium salt, 1,3-propanediol bis(hydrogen sulfate), 1,3-propanediol disulfate disodium salt, 2-sulfomethyl-1,4-butanedisulfonic acid, or 2-sulfomethylbutane-1,4-disulfonic acid trisodium salt. In a further embodiment, the anti-amyloidogenic agent is 1,3-propanedisulfonic acid or 1,3-propanedisulfonic acid disodium salt.

AA Amyloid Binding Assay (AAABA)

In the MS assay for AA, samples are prepared as aqueous solutions (adding 20% ethanol if necessary to solubilize in water), 200 µM of a test compound and 20 µM of solubilized AA, or 400 µM of a test compound and 40 µM of solubilized AA. The pH value of each sample is adjusted to 7.4 (±0.2) by addition of 0.1% aqueous sodium hydroxide. The solutions are then analyzed by electrospray ionization mass spectrometry using a Waters ZQ 4000 mass spectrometer. Samples are introduced by direct infusion at a flow-rate of 25 µL/min within 2 hours after sample preparation. The source temperature is kept at 70° C. and the cone voltage is 20 V for all the analysis. Data are processed using Masslynx 3.5 software. The MS assay gives data on the ability of compounds to bind to soluble AA.

D. Pharmaceutical Compositions Comprising The Compounds Of The Invention

The invention also pertains, at least in part, to a pharmaceutical composition comprising a therapeutically effective amount of a compound of formula (I) and second agent. In a further embodiment, the therapeutically effective amount is effective to treat AA amyloidosis.

In a further embodiment, the invention pertains to a packaged pharmaceutical composition. The packaged pharmaceutical composition includes a therapeutically effective amount of a compound of formula (I) packaged in combination with a label or insert advising that the composition be administered in combination with a second agent. In a further embodiment, the therapeutically effective amount is effective to treat AA amyloidosis.

In yet another further embodiment, the invention pertains to a packaged pharmaceutical composition, which includes a therapeutically effective amount of a second agent packaged in combination with a label or insert advising that the composition be administered in combination with a compound of formula (I).

The term "label or insert" includes, but is not limited to all written, electronic, or spoken communication with the subject, or with any person substantially responsible for the care of the subject, regarding the administration of the compositions of the present invention. An insert may further include information regarding coadministration of the compositions of the present invention with other compounds or compositions, e.g., second agents. Additionally, an insert may include instructions regarding administration of the compositions of the present invention without food.

In yet another embodiment, the invention pertains to a packaged pharmaceutical composition, which includes a container holding a pharmaceutical composition comprising a therapeutically effective amount of a compound of formula (I) in combination with a label or insert advising that the composition be administered without food.

The compounds of formula (I) may be supplied in a solution with an appropriate solvent or in a solvent-free form (e.g., lyophilized). In another aspect of the invention, the agents and buffers necessary for carrying out the methods of the invention may be packaged as a kit. The kit may be commercially used according to the methods described herein and may include instructions for use in a method of the invention. Additional kit components may include acids, bases, buffering agents, inorganic salts, solvents, antioxidants, preservatives, or metal chelators. The additional kit components are present as pure compositions, or as aqueous or organic solutions that incorporate one or more additional kit components. Any or all of the kit components optionally further comprise buffers.

The compounds of formula (I) may also be administered parenterally, intraperitoneally, intraspinally, or intracerebrally. Dispersions can be prepared in glycerol, liquid polyethylene glycols, and mixtures thereof and in oils. Under ordinary conditions of storage and use, these preparations may contain a preservative to prevent the growth of microorganisms.

To administer the compound of the invention by other than parenteral administration, it may be necessary to coat the agent with, or co-administer the agent with, a material to prevent its inactivation. For example, the compound of the invention may be administered to a subject in an appropriate carrier, for example, liposomes, or a diluent. Pharmaceutically acceptable diluents include saline and aqueous buffer solutions. Liposomes include water-in-oil-in-water CGF emulsions as well as conventional liposomes (Strejan et al., *J. Neuroimmunol.* 7, 27 (1984)). It should be noted that the term "pharmaceutical composition" includes the "pharmaceutical formulations" described above.

Pharmaceutical compositions suitable for injectable use include sterile aqueous solutions (where water soluble) or dispersions and sterile powders for the extemporaneous preparation of sterile injectable solutions or dispersion. In all cases, the composition must be sterile and must be fluid to the extent that easy syringability exists. It must be stable under the conditions of manufacture and storage and must be preserved against the contaminating action of microorganisms such as bacteria and fungi.

Suitable pharmaceutically acceptable vehicles include, without limitation, any non-immunogenic pharmaceutical adjuvants suitable for oral, parenteral, nasal, mucosal, transdermal, intravascular (IV), intraarterial (IA), intramuscular (IM), and subcutaneous (SC) administration routes, such as phosphate buffer saline (PBS).

The vehicle can be a solvent or dispersion medium containing, for example, water, ethanol, polyol (for example, glycerol, propylene glycol, and liquid polyethylene glycol, and the like), suitable mixtures thereof, and vegetable oils. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, isotonic agents are included, for example, sugars, sodium chloride, or polyalcohols such as mannitol and sorbitol, in the composition. Prolonged absorption of the injectable compositions can be brought about by including in the composition an agent which delays absorption, for example, aluminum monostearate or gelatin.

Sterile injectable solutions can be prepared by incorporating the therapeutic agent in the required amount in an appropriate solvent with one or a combination of ingredients enumerated above, as required, followed by filtered sterilization. Generally, dispersions are prepared by incorporating the therapeutic agent into a sterile vehicle which contains a basic dispersion medium and the required other ingredients from those enumerated above. In the case of sterile powders for the preparation of sterile injectable solutions, the methods of preparation are vacuum drying and freeze-drying which yields a powder of the active ingredient (i.e., the compound of the invention) plus any additional desired ingredient from a previously sterile-filtered solution thereof.

The compound of the invention can be orally administered, for example, with an inert diluent or an assimilable edible carrier. The compound of the invention and other ingredients may also be enclosed in a hard or soft shell gelatin capsule, compressed into tablets, or incorporated directly into the subject's diet. For oral therapeutic administration, the compound of the invention may be incorporated with excipients and used in the form of ingestible tablets, buccal tablets, troches, capsules, elixirs, suspensions, syrups, wafers, and the like. The percentage of the compound of the invention in the compositions and preparations may, of course, be varied. The amount of the compound of the invention in such therapeutically useful compositions is such that a suitable dosage will be obtained.

The present invention therefore includes pharmaceutical formulations comprising the compounds of the invention, including pharmaceutically acceptable salts thereof, in pharmaceutically acceptable vehicles for aerosol, oral and parenteral administration. Also, the present invention includes such compounds, or salts thereof, which have been lyophilized and which may be reconstituted to form pharmaceutically acceptable formulations for administration, as by intravenous, intramuscular, or subcutaneous injection. Administration may also be intradermal or transdermal.

In accordance with the present invention, an agent of formula (I) described herein, and pharmaceutically acceptable salts thereof, may be administered orally or through inhalation as a solid, or may be administered intramuscularly or intravenously as a solution, suspension or emulsion. Alternatively, the agents or salts may also be administered by inhalation, intravenously or intramuscularly as a liposomal suspension.

Pharmaceutical compositions or formulations are also provided which are suitable for administration as an aerosol, by inhalation. These formulations comprise a solution or suspension of the desired compound of the invention, or a salt thereof, or a plurality of solid particles of the agent or salt. The desired formulation may be placed in a small chamber and nebulized. Nebulization may be accomplished by compressed air or by ultrasonic energy to form a plurality of liquid droplets or solid particles comprising the agents or salts. The liquid droplets or solid particles should have a particle size in the range of about 0.5 to about 5 microns. The solid particles can be obtained by processing the solid agent of any compound of the invention, or a salt thereof, in any appropriate manner known in the art, such as by micronization. The size of the solid particles or droplets will be, for example, from about 1 to about 2 microns. In this respect, commercial nebulizers are available to achieve this purpose.

A pharmaceutical formulation suitable for administration as an aerosol may be in the form of a liquid, the formulation will comprise a water-soluble agent of a compound of the invention, or a salt thereof, in a carrier which comprises water. A surfactant may be present which lowers the surface tension of the formulation sufficiently to result in the formation of droplets within the desired size range when subjected to nebulization.

Peroral compositions also include liquid solutions, emulsions, suspensions, and the like. The pharmaceutically acceptable vehicles suitable for preparation of such compositions are well known in the art. Typical components of carriers for syrups, elixirs, emulsions and suspensions include ethanol, glycerol, propylene glycol, polyethylene glycol, liquid sucrose, sorbitol and water. For a suspension, typical suspending agents include methyl cellulose, sodium carboxymethyl cellulose, tragacanth, and sodium alginate; typical wetting agents include lecithin and polysorbate 80; and typical preservatives include methyl paraben and sodium benzoate. Peroral liquid compositions may also contain one or more components such as sweeteners, flavoring agents and colorants disclosed above.

Pharmaceutical compositions may also be coated by conventional methods, typically with pH or time-dependent coatings, such that the subject agent is released in the gastrointestinal tract in the vicinity of the desired topical application, or at various times to extend the desired action. Such dosage forms typically include, but are not limited to, one or more of cellulose acetate phthalate, polyvinylacetate phthalate, hydroxypropyl methyl cellulose phthalate, ethyl cellulose, waxes, and shellac.

Other compositions useful for attaining systemic delivery of the subject agents include sublingual, buccal and nasal dosage forms. Such compositions typically comprise one or more of soluble filler substances such as sucrose, sorbitol and mannitol; and binders such as acacia, microcrystalline cellulose, carboxymethyl cellulose and hydroxypropyl methyl cellulose. Glidants, lubricants, sweeteners, colorants, antioxidants and flavoring agents disclosed above may also be included.

The compositions of this invention can also be administered topically to a subject, e.g., by the direct laying on or spreading of the composition on the epidermal or epithelial tissue of the subject, or transdermally via a "patch". Such compositions include, for example, lotions, creams, solutions, gels and solids. These topical compositions may comprise an effective amount, usually at least about 0.1%, or even from about 1% to about 5%, of a compound of the invention. Suitable carriers for topical administration typically remain in place on the skin as a continuous film, and resist being removed by perspiration or immersion in water. Generally, the carrier is organic in nature and capable of having dispersed or dissolved therein the therapeutic agent. The carrier may include pharmaceutically acceptable emollients, emulsifiers, thickening agents, solvents and the like.

Toxicity and therapeutic efficacy of such agents can be determined by standard pharmaceutical procedures in cell cultures or experimental animals, e.g., for determining the LD50 (the dose lethal to 50% of the population) and the ED50 (the dose therapeutically effective in 50% of the population). The dose ratio between toxic and therapeutic effects is the therapeutic index and can be expressed as the ratio LD50/ED50, and usually a larger therapeutic index is more efficacious. While compounds that exhibit toxic side effects may be used, care should be taken to design a delivery system that targets such agents to the site of affected tissue in order to minimize potential damage to unaffected cells and, thereby, reduce side effects.

It is understood that appropriate doses depend upon a number of factors within the ken of the ordinarily skilled physician, veterinarian, or researcher. The dose(s) of the small molecule will vary, for example, depending upon the identity, size, and condition of the subject or sample being treated, further depending upon the route by which the composition is to be administered, if applicable, and the effect which the practitioner desires the small molecule to have upon the subject. Exemplary doses include milligram or microgram amounts of the small molecule per kilogram of subject or sample weight (e.g., about 1 microgram per kilogram to about 500 milligrams per kilogram, about 100 micrograms per kilogram to about 5 milligrams per kilogram, or about 1 microgram per kilogram to about 50 micrograms per kilogram). It is furthermore understood that appropriate doses depend upon the potency. Such appropriate doses may be determined using the assays known in the art. When one or more of these compounds is to be administered to an animal (e.g., a human), a physician, veterinarian, or researcher may, for example, prescribe a relatively low dose at first, subsequently increasing the dose until an appropriate response is obtained. In addition, it is understood that the specific dose level for any particular animal subject will depend upon a variety of factors including the activity of the specific compound employed, the age, body weight, general health, gender, and diet of the subject, the time of administration, the route of administration, the rate of excretion, and any drug combination.

For subjects having AA amyloidosis or renal impairment, doses may depend on the state of renal function in the subject, as measured, for example, by the rate of creatinine clearance, which may affect the rate of clearance of the compound from the subject. In this case, subjects with a lower rate of creatinine clearance would be expected to achieve a particular plasma concentration at a lower dose than those with a higher rate of creatinine clearance.

Parenteral compositions may be formulated in dosage unit form for ease of administration and uniformity of dosage. Dosage unit form as used herein refers to physically discrete units suited as unitary dosages for the subjects to be treated; each unit containing a predetermined quantity of compound of the invention calculated to produce the desired therapeutic effect in association with the required pharmaceutical vehicle. The specification for the dosage unit forms of the invention are dictated by and directly dependent on (a) the unique characteristics of the therapeutic agent and the particular therapeutic effect to be achieved, and (b) the limitations inherent in the art of compounding such a compound of the invention for the treatment of AA amyloidosis or amyloid related disease.

For example, the therapeutically effective amount of the compound of formula (I) may be between about 100 and 2500 mg daily. The compounds of the invention may be manufactured in capsules with dosages of 200 mg, 400 mg, or 800 mg of the compound of the invention. Alternatively, the compounds of the invention may be administered with dosages of 400 mg BID, 800 mg BID, or 1200 mg BID.

Those skilled in the art will recognize, or be able to ascertain using no more than routine experimentation, numerous equivalents to the specific procedures, embodiments, claims, and examples described herein. Such equivalents are considered to be within the scope of this invention and covered by the claims appended hereto. The contents of all references, issued patents, and published patent applications cited throughout this application are hereby incorporated by reference. The invention is further illustrated by the following examples, which should not be construed as further limiting.

EXEMPLIFICATION OF THE INVENTION

Example 1

An open-label, non-randomized, parallel group study to assess the pharmacokinetic profile of a single oral dose of 800 mg 1,3-propanedisulfonic acid disodium salt (PDS) in subjects with varying degrees of renal impairment as compared to healthy volunteers is conducted. Blood and urine samples are collected for 24 hours following dosing. Plasma and urine concentrations in 1,3-propanedisulfonic acid are determined using validated HPLC methods. Overall, renal impairment is associated with lower renal clearance and greater systemic exposure (characterized by AUC and $C_{max}$) to PDS compared to healthy subjects. Consequently, a decrease in dose appears to be necessary to maintain an acceptable systemic exposure in patients with impaired renal function. Results are shown in Table 1.

TABLE 1

| Degree of Renal Impairment | Glomerular Filtration Rate (GFR)[1] | $C_{max}$ (ng/mL) | $T_{max}$ (h) | $AUC_{0-Tlast}$ (ng · h/mL) | $AUC_{\infty}$[2] (ng · h/mL) |
|---|---|---|---|---|---|
| Healthy (n = 6) | >80 mL/min | 1240 (511-2080) | 0.5 (0.25-0.75) | 3158 (1276-5019) | 5367 (2937-8582) |
| Mild (n = 6) | 50-80 mL/min | 3064 (1113-6199) | 0.5 (0.25-0.75) | 9107 (3794-15247) | 12974 (4773-19206) |
| Moderate (n = 4) | 30-50 mL/min | 2105 (851-4322) | 0.5 (0.25-2.0) | 9448 (5969-13773) | 10740 (7044-15462) |
| Severe (n = 6) | <30 mL/min | 2206 (838-4043) | 2.5 (0.25-6.0) | 29163 (12933-58365) | 43121 (23784-90825) |

Values are mean with ranges (minimum and maximum for individual patients) in parentheses except for $T_{max}$ for which the median is presented with the range in parentheses.
[1]As determined by the inulin clearance.
[2]Determined only for subjects for whom the elimination rate constant could be estimated.

Example 2

A multicenter, multinational, randomized, double-blind, placebo-controlled, and parallel-design study to assess the efficacy and safety of 1,3-propanedisulfonic acid disodium salt (PDS) in subjects having secondary (AA) amyloidosis is conducted. A total of 183 subjects are randomized to receive either PDS or placebo twice daily for 24 months. Dosing depends on the severity of renal impairment in a subject:

subjects having creatinine clearance (ClCr) >80 mL/min receive 1200 mg BID; for ClCr between 30 and 80 mL/min, the subject receives 800 mg BID; and for ClCr between 20 and 30 mL/min and until the possible initiation of dialysis, the subject receives 400 mg BID. If ClCr decreases or increases to the next lower or higher range level, the dose regimen is adjusted accordingly. Subject medication is administered orally (capsule). Each patient is evaluated on 16 occasions, including on-site visits at months 0 (baseline), 1, 4, 8, 12, 16, 20 and 24.

Changes from baseline in serum creatinine and creatinine clearance normalized for body surface area are assessed throughout the study (Screening, Baseline, Month 4, 8, 12, 16, 20, and 24 visits). Subjects are asked to collect their urine for 24 hours as per instructions the day prior to the scheduled visit. The volume of urine is recorded in the case report form at study site and an aliquot of urine is sent to the central laboratory for determination of urinary creatinine. A blood sample is collected to measure serum creatinine. The creatinine clearance (ClCr) is calculated using the following formula and recorded in the case report form:

$$ClCr = \frac{\text{urine creatinine}(mg/dl) \times \text{urine volume}(ml)}{\text{serum creatinine}(mg/dl) \times \text{time}(min)}$$

The creatinine clearance normalized for body surface area is calculated by dividing the creatinine clearance by the body surface area. Body surface area is calculated with the following equation: $Wt^{0.425} \times Ht^{0.725} \times 0.007184$ (DuBois D, *Clinical Calorimetry, Arch Intern Med* 1916; 17:87).

Subjects are classified into three categories based on a composite assessment of renal function at the end of the 24 month treatment period compared to baseline. Subjects are classified as "worse" if at least one of the following clinical milestones of worsening is met: a 50% reduction in creatinine clearance, a doubling of serum creatinine levels, progression to ESRD/dialysis, or death. Subjects are classified as "improved" if the following clinical milestones of improvement are met: ≧50% increase in ClCr and no clinical milestones of worsening. Subjects are classified as "stable" if none of the clinical milestones of worsening or improvement are met. Using this criteria, 13.4% fewer subjects receiving PDS are worse compared to those receiving placebo, and 13.4% more subjects receiving PDS are stable or improved compared to placebo (p value=0.06).

Example 3

Efficacy Analysis

All the statistical analyses will be based on the subject population as described. The "Safety population" will be the set of all subjects randomized to a treatment group who took at least one dose of the study drug (PDS). Subjects who were randomized during the screening period but did not meet one of the inclusion criteria at baseline and therefore did not take PDS will not be included in the Safety population. The "Intent-to-Treat (ITT) population" will consist of the Safety population, i.e., all subjects who are randomized and who have taken any amount of PDS. The "Efficacy Evaluable (per protocol; PP) population" will be a subset of the ITT subjects. It will consist of all subjects who complete the treatment period and can be assessed for the primary efficacy endpoint. It will exclude subjects under the following circumstances: initiation of angiotensin converting enzyme (ACE) inhibitor or angiotensin II receptor antagonist therapy during the study; use of rescue medications; discontinuations due to reasons other than progression to ESRD/dialysis or death; major protocol violations; and low compliance rate.

Primary Efficacy Endpoint All subjects are categorized according to the evolution of their disease ("worse", "stable", or "improved"). This constitutes the primary efficacy endpoint for the study and is analyzed in the Intent-to-Treat (ITT) population according to two pre-specified statistical methodologies: 1) the Cochran-Mantel-Haenszel row mean scores test (CMH test) to compare the percentage of subjects who reach each category at the end of the study in comparison to their status at Baseline, and 2) a proportional hazards regression model (Cox analysis) to compare between treatment groups both the number of first "worse" events, as well as when they occur, thus making more use of all available data. Both methodologies are adjusted for the stratification of nephrotic status at Baseline (nephrotic vs non-nephrotic) as pre-specified.

For the primary endpoint using the CMH row mean scores test, summary statistics, such as the number and the percentage of patients who reach each category of this composite assessment at the end of the study are to be presented by treatment group. Since the response levels may not necessarily be viewed as equally spaced but have a clear ordering, the modified ridit scores option is to be used. This scoring method requires no scaling of the response levels other than that implied by their relative ordering. The CMH test statistic is not to be stratified by center because of the large number (27) of investigative sites relative to the sample size. The center effect is therefore to be investigated using only descriptive statistical methods. The country effect is also to be investigated descriptively.

If the sample size in certain cells is too small for the requirements of any statistical test, it is pre-specified that the "Improved" and the "Stable" categories of the composite variable will be collapsed to create a "Worse" versus "Stable or Improved" outcome. This is to apply to subgroup analyses or other exploratory analyses as well.

For the primary endpoint using the Cox proportional hazards regression model, the association between treatment and the composite endpoint can be adjusted for several Baseline variables, but to allow comparisons to the CMH test methodology, only the nephrotic status at Baseline (nephrotic vs non-nephrotic) is to be used initially for adjustments. Other variables which could be included in other analyses using the Cox model are: treatment groups, age, Baseline CrCl, Baseline proteinuria, Baseline SCr, and underlying disease (familial Mediterranean fever, rheumatic inflammatory diseases, and miscellaneous).

The primary efficacy endpoint is a composite assessment of clinical improvement/worsening of renal function. At the end of the study, the subjects are classified into three categories, "Worse" and death (all causes), "Stable", or "Improved". The subjects are classified as "worse" if at least one of the following clinical milestones of worsening is met: doubling of serum creatinine from baseline to Month 24; 50% or greater decrease in creatinine clearance normalized for body surface area from baseline to End of Study; progression to dialysis/ESRD; or death. The subjects are classified as "stable" if none of the clinical milestones of worsening or improvement are met. The subjects are classified as "improved" if the following clinical milestones of improvement are met: a 50% or greater increase in creatinine clearance normalized for body surface area from baseline to End of Study; and no clinical milestones of worsening. The term "End of Study" is defined as Month 24 for subjects who completed the study and as the last available measurement for the subjects who discontinued early.

At the End of the Study, it is found that there is a reduction in the risk of any "worse" event of renal decline or all-cause mortality to 42% of the risk for placebo. This is consistent with the result of fewer "worse" patients in the treated group. Furthermore, the median time to the first "worse" event is 6.4 months longer in subjects treated with PDS (14.5 months for treated vs. 8.1 months for placebo). A graph depicting a Kaplan-Meier curve for the time to the first "worse" event is shown in FIG. 1.

Secondary Efficacy Endpoints

The secondary efficacy endpoints are an assessment of clinical improvement/worsening of both renal and gastrointestinal functions. At the end of the study, subjects are classified into three categories based on their condition: worse, stable, or improved. Examples of secondary efficacy endpoints include 1) the slope of creatinine clearance normalized for body surface area over time; 2) the slope in the reciprocal of serum creatinine (1/serum creatinine) over time; 3) time to renal events (e.g., such as, time to doubling of serum creatinine; time to ≧50% increase in creatinine clearance normalized for body surface area; time to ≧50% decrease in creatinine clearance normalized for body surface area; time to dialysis/ESRD; and/or time to death); and 4) changes from baseline to End of Study in proteinuria and creatinine clearance normalized for body surface area.

For quantitative secondary efficacy parameters, summary statistics, such as the number of observation (n), mean, SD, median, minimum, and maximum values, are displayed by treatment group at each evaluation visit. The actual value and percent change from Baseline are also presented by treatment group at each evaluation visit. Moreover, treatment groups are compared using a two-way analysis of covariance (AN-COVA), controlling for Baseline and renal status at Baseline.

The initial full model to be tested will be:

Change from Baseline =

Treatment + Baseline value + Renal status at Baseline +

(Renal Status at Baseline * Treatment) + (Baseline value * Treatment)

where:
Treatment=PDS vs. Placebo
Baseline value=subject's baseline value for the tested parameter
Renal Status at Baseline=Nephrotic vs. Non-Nephrotic
Renal Status at Baseline*Treatment=Interaction term for Renal Status at Baseline by Treatment
Baseline value*Treatment=Interaction term for Baseline value by treatment The two interaction terms will be dropped from the primary model if the test for their respective significance results in p-values greater than 10%. The primary test for treatment difference will be then done using the resultant model. If the assumptions underlying the ANCOVA model are not satisfied, then a rank transformation approach (Inman and Conover) will be used. Following the Iman and Conover procedure, the entire set of observations are ranked from smallest to largest, with the smallest observation having rank 1, the second smallest rank 2, and so on. In case of ties, average ranks will be used. Following the appropriate transformation, the procedure ANCOVA model without the baseline covariate will be applied to the transformed data in a manner similar to that described above.

For qualitative secondary efficacy parameters, the number and percentage of subjects in each category of the analyzed parameter will be displayed by treatment group at each evaluation visit. Moreover, treatment groups will be compared similarly to the primary efficacy endpoint, the using Cochran-Mantel-Haenszel (CMH) row mean scores test adjusted for the renal status at Baseline (nephrotic v. non-nephrotic).

At the End of the Study, it is found that the risk of doubling of serum creatinine is reduced by 59% as compared to the subjects treated with placebo. It is also found that the risk of ≧50% decrease in creatinine clearance is reduced by 52% and that the risk of dialysis/ESRD is reduced by 46% as compared to subjects treated with placebo.

Slope of Creatinine Clearance Normalized for Body Surface Area Over Time

The slope of creatinine clearance over time is commonly used clinically by nephrologists to predict long-term renal outcome and time to ESRD. A negative slope indicates a loss of renal function. The more negative the slope, the faster the loss of renal function.

Creatinine clearance is assessed at the Screening, Baseline, Month 4, 8, 12, 16, 20, and 24 visits through a 24 hr urine collection at each time point. This parameter will be normalized for body surface area and the least-squares estimate of the within-subject slope will be calculated using all available creatinine clearance measurements. Although the study is for 2 years, the slope will be expressed as an annual rate of change. If the data exhibits a nonlinear change over time, then a suitable transformation (i.e. log transformation) will be applied prior to the slope calculation.

To assess the within-subject slope, a regression will be performed for each subject, thus providing a slope for each subject. Subsequently, summary statistics of the within-subject slope values will be presented by treatment group at each visit on both the ITT and Efficacy Evaluable populations.

Figure 2:
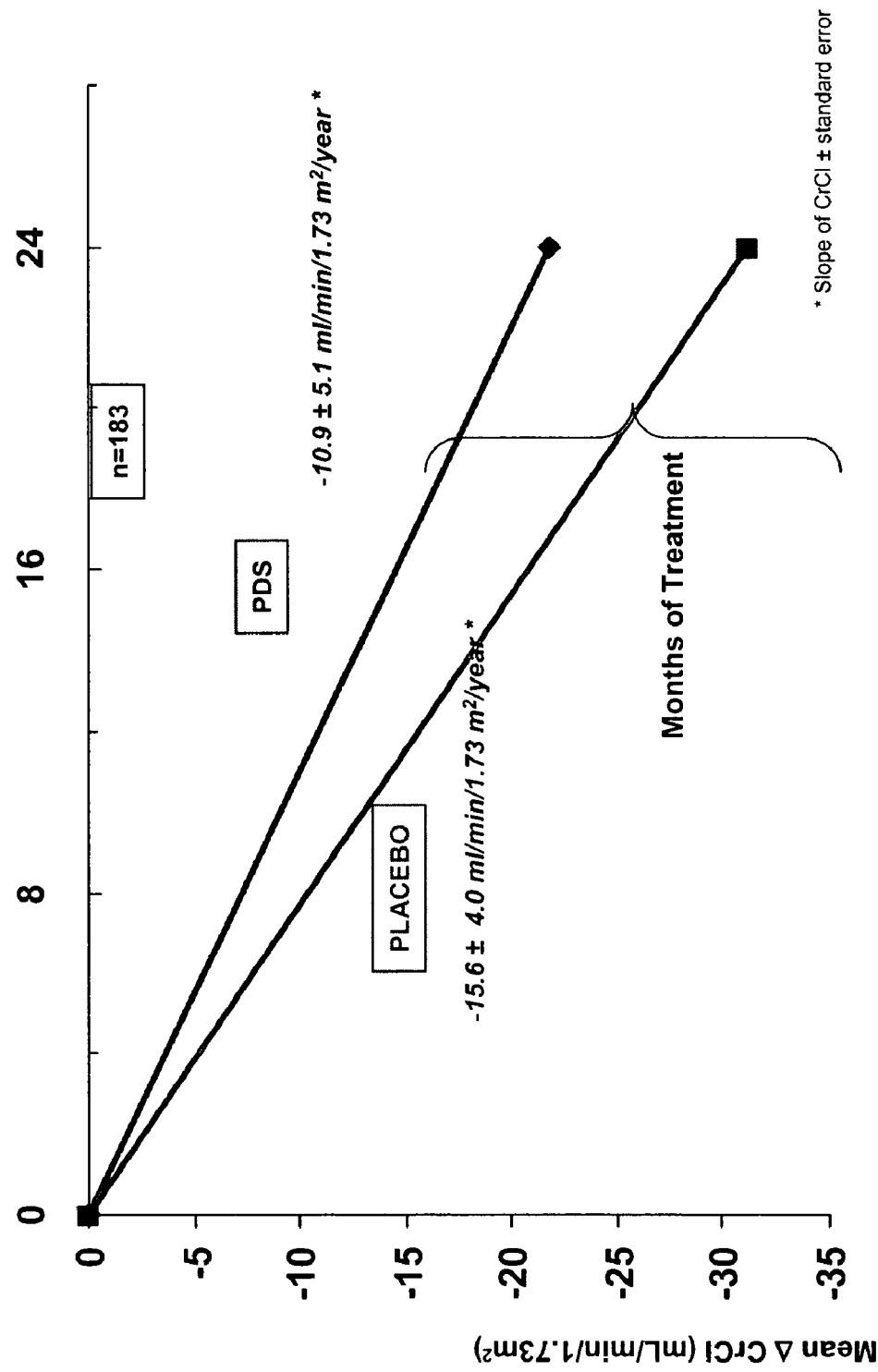
FIG. 2 is a line graph showing the slope of creatinine clearance for subjects administered PDS versus a placebo.

At the End of the Study, it is found that treatment with PDS reduced the rate of loss in renal function in AA Amyloidosis subjects, as measured by the slope of creatinine clearance over time. There is a 30.1% reduction in the rate of loss of renal function in PDS-treated subjects (a mean difference of 4.7 mL/min/1.73 m$^2$/year in treated vs. placebo), as shown in Table 2 and FIG. 2.

TABLE 2

| STATISTICS | PDS (N = 89) | PLACEBO (N = 94) | P-VALUE |
|---|---|---|---|
| n | 85 | 86 | |
| Mean (S.E.) | −10.9 (5.1) | −15.6 (4.0) | |
| Median | −5.9 | −8.6 | 0.025 |
| Range | −355.4; 184.7 | −258.8; 79.4 | |

Slope of the Reciprocal of Serum Creatinine Over Time

Serum creatinine is assessed at the Screening, Baseline, Month 4, 8, 12, 16, 20, and 24 visits. The least-squares estimate of the within-subject slope will be calculated using all available serum creatinine measurements. Although the study is for 2 years, the slope will be expressed as an annual rate of change. If the data exhibits a nonlinear change over time, then a suitable transformation (i.e. log transformation) will be applied prior to the slope calculation. These assessments will be made on the ITT as well as the Efficacy Evaluable population.

To assess the within-subject slope, a regression will be performed for each subject, thus providing a slope for each patient. Subsequently, summary statistics of the within-subject slope values will be presented by treatment group at each visit on both the ITT and Efficacy Evalubale populations.

Time (Month) Calculations

For the following calculations, summary statistics such as survival Kaplan-Meier estimates with 99% CI, quartiles and median survival time are presented by the treatment group on the ITT population. The 99% CI is based on the Greenwood variance formula. The KM estimates is presented for the following time windows: day 0 to 112, day 113 to 224, day 225 to 336, day 337 to 448, day 449 to 560, and more than 560 days.

The two treatment groups are compared using the stratified log-rank test and the stratification factor is the renal status at Baseline (nephrotic vs. non-nephrotic). Four groups are compared on a Kaplan-Meier plot to depict the time to event in each treatment group: baseline nephrotic (treated vs. untreated) and baseline non-nephrotic (treated vs. untreated).

| | |
|---|---|
| Time to Double Serum Creatinine | $\frac{[(\text{date of first event of doubled serum creatinine from Baseline} - \text{Baseline date}) + 1]}{30.4375}$ |
| Time to ≧50% Increase/Decrease in Creatinine Clearance Normalized for Body Surface Area | $\frac{[(\text{date of first event of} \geq 50\% \text{ increase/decrease from Baseline in creatinine clearance*} - \text{Baseline date}) + 1]}{30.4375}$ |
| Time to Dialysis/ESRD | $\frac{[(\text{date of dialysis/ESRD} - \text{Baseline date}) + 1]}{30.4375}$ |
| Time to Death | $\frac{[(\text{date of death} - \text{Baseline date}) + 1]}{30.4375}$ |

*normalized for body surface area

Figure 3:
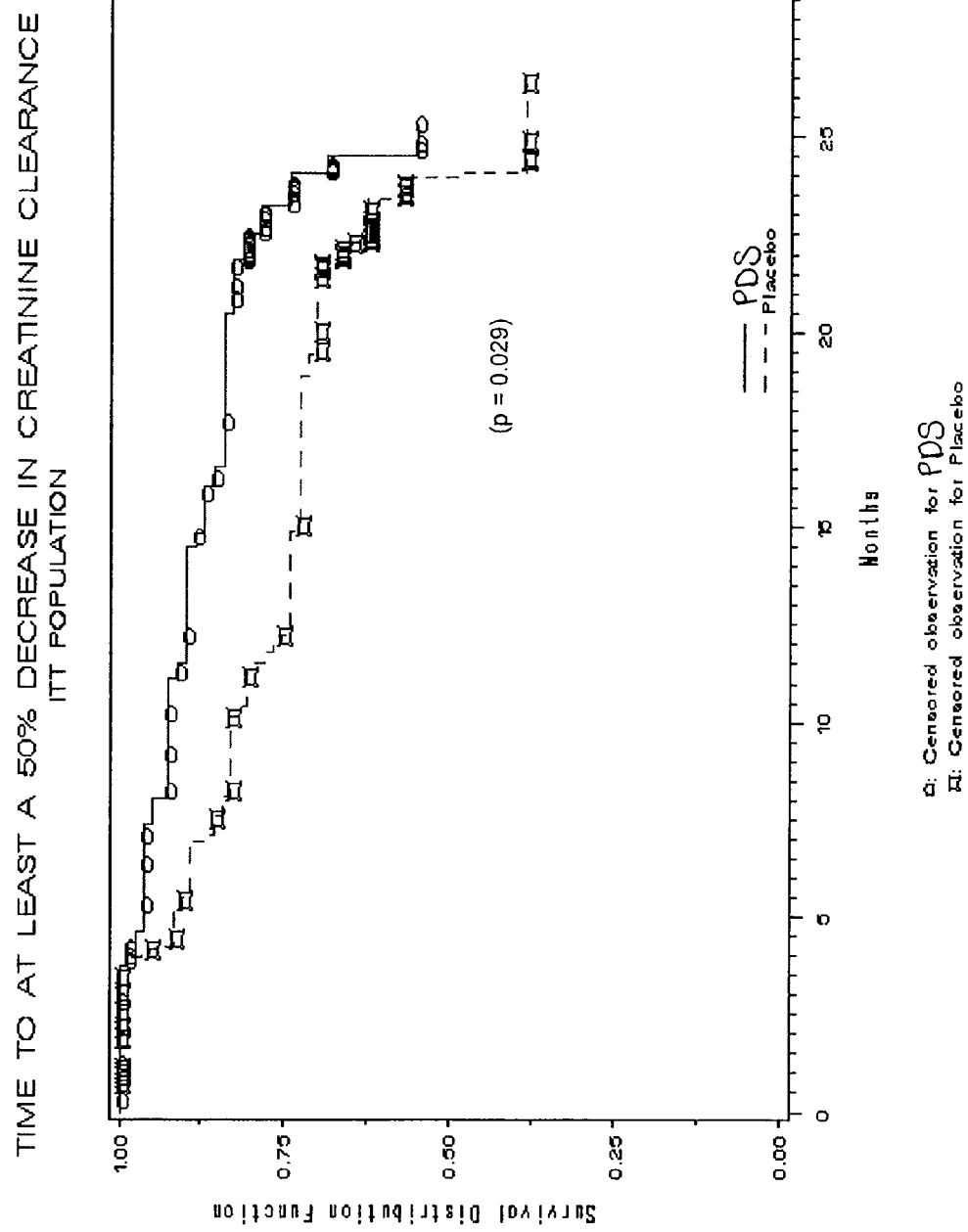
FIG. 3 is a graph depicting a Kaplan-Meier curve for the time to a 50% decrease in creatinine clearance for subjects administered PDS versus a placebo.
Figure 4:
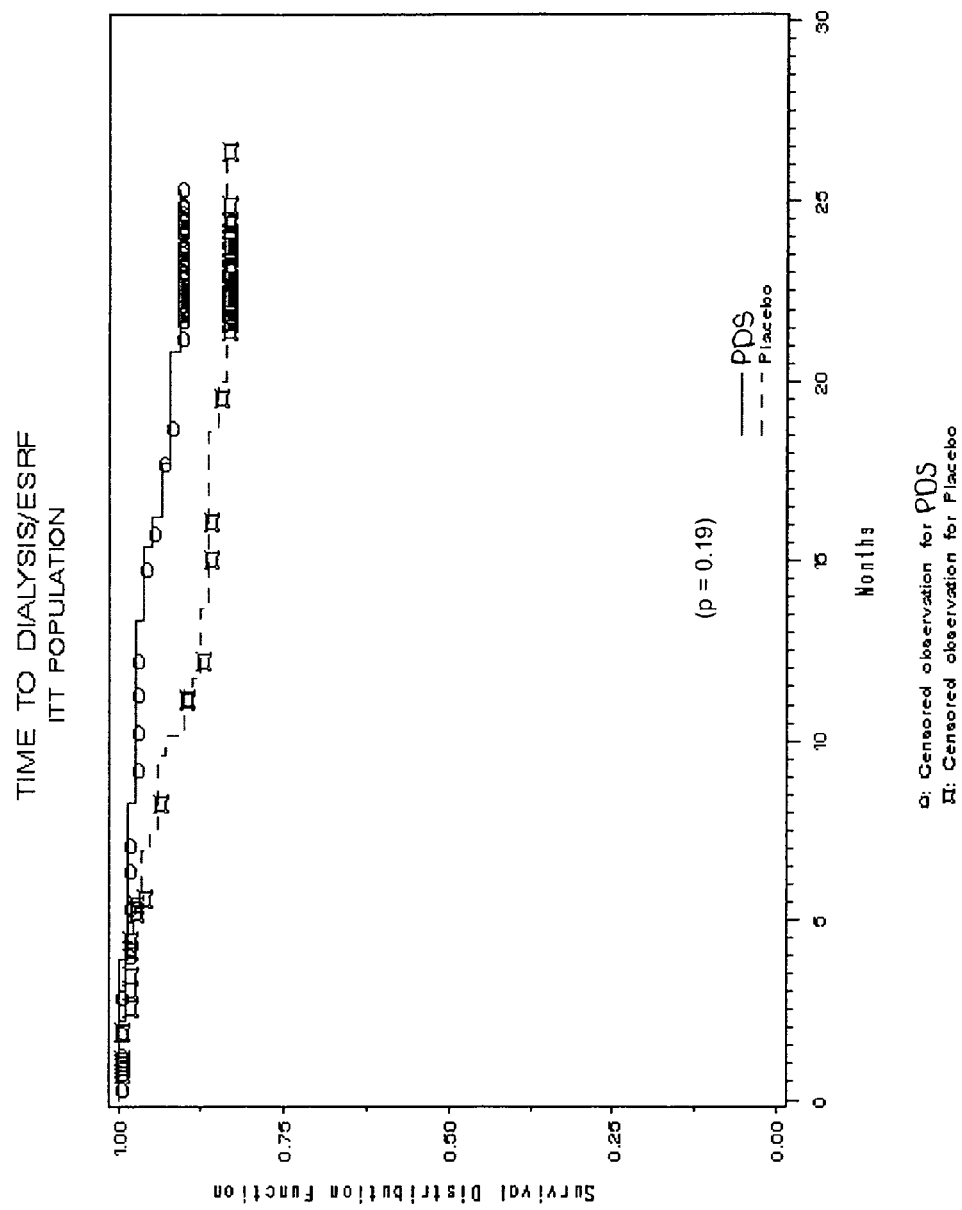
FIG. 4 is a graph depicting a Kaplan-Meier curve for the time to ESRD/Dialysis for subjects administered PDS versus a placebo.

At the End of the Study, in those patients with a doubling of SCr, it is found that the median time to doubling of serum creatinine is 3.6 months longer in PDS treated subjects compared to placebo treated subjects. Furthermore, in those patients with a ≧50% decrease in CrCl, the median time to at least a 50% decrease in creatinine clearance is 4.4 months longer in PDS treated subjects in comparison to placebo treated subjects (see FIG. 3 for a Kaplan-Meier curve). In addition, in those patients progressing to dialysis, it is also found that the median time to dialysis is 5.3 months longer in PDS treated subjects in comparison to placebo treated subjects (see FIG. 4 for a Kaplan-Meier curve).

Changes from Baseline in Proteinuria and Creatinine Clearance

Proteinuria, creatinine clearance, and serum creatinine are assessed at Screening, Baseline, Month 4, 8, 12, 16, 20, and 24 visits. Change from baseline to End of Study in Proteinuria and Creatinine Clearance will be analyzed as a secondary efficacy endpoint. The End of Study is defined as Month 24 for subjects who completed and as the last available visit for subjects who discontinued early. At Screening, proteinuria, creatinine clearance, and serum creatinine are to be collected from two distinct assessments which are to have been at least 1 week apart and within 3 months prior to study entry (Baseline visit). For the creatinine clearance parameter, the normalized value will be used.

Proteinuria/Creatinine Clearance/Serum Creatinine/Serum Albumin/Serum Alkaline Phosphatase Proteinuria, creatinine clearance, serum creatinine, serum albumin and serum alkaline phosphatase are assessed at Screening, Baseline, Month 4, 8, 12, 16, 20 (except for serum albumin and serum alkaline phosphatase), and 24 visits. At Screening, proteinuria, creatinine clearance and serum creatinine are to have been collected from two distinct assessments which had to be at least 1 week apart and within 3 months prior to study entry.

For the serum creatinine (SCr) parameter, both the value and its reciprocal, i.e., 1/SCr, will be analyzed. For the creatinine clearance parameter, the normalized value will be used. Summary statistics of the actual value of each of these parameters will be presented by treatment group at each visit on the ITT population. Summary statistics will also be provided for the change from Baseline and the percent change from Baseline at each post-Baseline assessment for each of these parameters.

For proteinuria and creatinine clearance normalized for body surface area, comparison of treatment groups will be done on the change from Baseline to Month 4, 8, 12, 16, and 20 as described for the secondary efficacy quantitative parameters. Similar models will be presented for changes from baseline to Month 4, 8, 12, 16, 20, and 24 in serum creatinine, serum albumin, and serum alkaline phosphatase.

At the end of the study, PDS treated subjects showed a mean difference in CrCl of $-14.7 \pm 4.2$ mL/min/1.73 m$^2$ vs $-22.3 \pm 4.1$ mL/min/1.73 m$^2$ in placebo treated patients (estimated difference of 7.7 mL/min/1.73 m$^2$). Table 3 depicts data from this study which show the change from the baseline to the end of the study.

TABLE 3

| PARAMETER | STATISTICS | PDS (N = 89) | PLACEBO (N = 94) |
|---|---|---|---|
| Baseline | n | 85 | 86 |
| | Mean (S.E.) | 79.34 (5.79) | 72.86 (5.78) |
| | Median | 66.61 | 53.24 |
| | Range | 11.55; 265.73 | 9.43; 257.42 |
| Change from End of Study to Baseline | n | 85 | 86 |
| | Mean (S.E.) | −14.68 (4.19) | −22.34 (4.07) |
| | Median | −11.35 | −13.79 |
| | Range | −226.14; 123.11 | −176.08; 28.78 |
| | p-value | 0.058 | |

Nephrotic Syndrome Status: Progression to and Remission

Nephrotic syndrome is defined in this example as heavy proteinuria (urinary protein>3 g/24hr) associated with the two following extrarenal features: 1) hypoalbuminemia (serum albumin<3.4 g/dL) and 2) peripheral edema by physical examination and/or use of diuretics to treat edema.

Progression to nephrotic syndrome in subjects without nephrotic syndrome at baseline is defined as follows: an increase in proteinuria to >3 g/24hr (needs to be <3 g/24hr at Baseline) and occurrence of the two following extrarenal features: 1) hypoalbuminemia (not present at Baseline) and 2) edema and/or use of diuretics to treat edema (no edema and no use of diuretics at Baseline). If subjects do not meet all three criteria at the end of the study, they will not be considered nephrotic for the purpose of the study analysis. If subjects progress to ESRD/dialysis, and have missing information on either serum albumin or edema, they will not be considered as having progressed to nephrotic syndrome, but the information on their deterioration will nevertheless be captured in the primary endpoint analysis.

Remission of nephrotic syndrome in subjects with nephrotic syndrome at baseline is defined as follows: a decrease in proteinuria to ≦1 g/24 h (needs to be >3 g/24 hr at Baseline) and an improvement in one of the two following extrarenal features: 1) increase in serum albumin to ≧3.4 g/dL (if serum albumin <3.4 g/dL at Baseline or at any other time during the study) or 2) resolution of edema and/or discontinuation of diuretics in response to improvement in edema (if edema was a presenting symptom or if a patient used diuretics at Baseline or at any other time during the study).

Orthostatic Hypotension

The autonomic nervous system (ANS) may be affected in AA amyloidosis. A postural decrease in blood pressure is defined as a drop from the supine to standing position of ≧20 mmHg in systolic blood pressure (SBP) or 10 mmHg in diastolic blood pressure (DBP). If the drop in systolic or diastolic blood pressure is sustained for at least 3 minutes, it is a sign of ANS dysfunction. Blood pressure is measured in the supine, standing, and standing-3-minutes-later positions at the Screening, Baseline, Month 4, 8, 12, 16, 20, and 24 visits.

Descriptive statistics such as the number and the percentage of subjects in each category (yes vs. no) is presented by treatment group and at each study visit on the ITT population. Treatment groups are compared using a CMH general association test adjusted for the renal status at Baseline.

Splenomegaly/Hepatomegaly

Splenomegaly is defined as an enlargement of the spleen. Spleen size will be measured by physical examination at Screening, Baseline, Month 4, 8, 12, 16, 20 and 24 visits. It is measured in centimeters from the left costal margin at then anterior axillary line, using a ruler. Measures are taken when the subject is lying down and at the end of inspiration.

Hepatomegaly is defined as an enlargement of the liver. Liver size will be measured by physical examination at Screening, Baseline, Month 4, 8, 12, 16, 20 and 24 visits. It is measured in centimeters from the right costal margin at the mid-clavicular line, using a ruler. Measures are taken when the patient is lying down and at the end of inspiration.

Pharmacokinetics Analysis

In the following examples, terms are as defined below. The pharmacokinetic parameters were derived by non-compartmental analysis using WinNonlin® (Pharsight Corp., Mountain View, Calif., USA).

$C_{max}$—the maximum observed plasma concentration.

$T_{max}$—the time of occurrence of $C_{max}$.

$AUC_{0-t}$—the area under the plasma concentration versus time curve from time zero to the last sampling time at which concentrations were at or above the limit of quantification, calculated by the linear trapezoidal rule.

$AUC_{\infty}$—the area under the plasma concentrations versus time curve from time zero to infinity, calculated from $AUC_{0-t}+(C_{last}/\lambda_z)$, where $C_{last}$ is the last observed quantifiable concentration and $\lambda z$ is the apparent terminal rate constant.

$t_{1/2}$—the apparent terminal half-life, calculated from $\ln 2/\lambda_z$

Example 4

The safety, tolerability and pharmacokinetics of PDS following single oral administration in healthy male adult volunteers is determined. The effect of food on the pharmacokinetics of PDS is also determined. The first part of the study is a randomized, double-blind, placebo-controlled study to assess the pharmacokinetic profile of 6 single rising oral doses of PDS in healthy male subjects. The second part of this study is an open-label, two-way crossover study to investigate the effect of food on the pharmacokinetic profile of a single oral dose of PDS under fasted and fed conditions. Blood samples are collected during 36 hours following dosing. Plasma concentrations of PDS are determined using validated HPLC methods. Following single oral doses of PDS maximum plasma concentrations are generally reached within 0.5 to 1 hour post-dose and the mean half-life ($T_{1/2}$) ranges from 2 to 26 hours. The extent of systemic exposure (AUC and $C_{max}$) to PDS increases with increasing dose. This increase is reasonably proportional to the administered dose. Moreover, there is a decrease in both the rate and extent of systemic availability when PDS is administered under fed conditions. PDS should therefore not be given concomitantly with a high fat meal. Results are shown in Table 4.

TABLE 4

Pharmacokinetic Parameters of PDS showing Single Oral Administration of 100, 200, 400, 800, 1600 and 2400 mg to Healthy Male Subjects and 1600 mg to Healthy Male Subjects (Fasted and Fed state)

| Dose | $C_{max}$ (ng/mL) | $T_{max}$ (h) | $AUC_{0-t}$ (ng · h/mL) | $AUC_{\infty}$* (ng · h/mL) |
|---|---|---|---|---|
| 100 mg (n = 6) | 99.5 (71.5-120) | 1 (0.5-2.5) | 240 (180-307) | 419 (358-480) |
| 200 mg (n = 5) | 164 (112-228) | 1 (0.5-2) | 626 (217-1186) | NC |
| 400 mg (n = 5) | 1078 (167-2633) | 0.5 (0.25-1) | 1884 (751-3368) | 2905 (1983-3828) |
| 800 mg (n = 10) | 2867 (208-6068) | 0.5 (0.25-1.5) | 4844 (1060-8965) | 4553 (3200-6285) |
| 1600 mg (n = 5) | 4762 (1571-9862) | 0.5 (0.25-0.5) | 8411 (6313-14741) | NC |
| 2400 mg (n = 5) Fasted | 6046 (1440-8802) | 0.5 (0.5-0.5) | 11986 (5421-16001) | 12913 (7350-16050) |
| 1600 mg (n = 8) Fed (high-fat meal) | 6455 (2403-10417) | 0.5 (0.25-0.5) | 11546 (6585-15776) | 12807 |
| 1600 mg (n = 8) | 563 (228-1321) | 2.25 (0.5-4) | 4014 (2767-4608) | 6320 (4394-9761) |

Values are the mean with ranges (i.e. minimum and maximum values for individuals) in parentheses, except for $T_{max}$ which is the median.
NC: Not calculated Example 5

The safety, tolerability and pharmacokinetics of PDS following multiple rising oral doses in healthy male adult volunteers is determined. This is a randomized, double-blind, placebo-controlled study to assess the pharmacokinetic profile of single and repeated oral doses of PDS at 400, 800 and 1600 mg in healthy male subjects. PDS is administered as a single oral dose to healthy male subjects at 400, 800 and 1600 mg on Days 1 and 7. Following the single oral administration on Day 1, PDS is administered on Days 2, 3, 4, 5 and 6 at 400, 800 and 1600 mg four times daily, or 1600 mg three times daily. Blood samples are collected through 24 hours after the dose on Day 1, before the first and last doses on Days 2 through 6, and after 48 hours after the final dose on Day 7. Plasma concentrations of PDS are determined using validated HPLC methods. Following single and repeated oral doses of PDS maximum plasma concentrations are generally reached within 0.25 to 1 hour post-dose. The mean half-life ($T_{1/2}$) ranges from 5 to 20 hours after single or multiple dosing. Accumulation after multiple dosing is consistent with the $T_{1/2}$ and dosing frequency. The extent of systemic exposure ($AUC_{0-t}$ and $C_{max}$) to PDS increases with increasing dose and this increase in 10 systemic exposure is approximately proportional to the administered dose. Results are shown in Table 5.

TABLE 5

Pharmacokinetic Parameters of PDS following Multiple Oral Doses of 400, 800 and 1600 mg to Healthy Male Subjects

| Dose | $C_{max}$ (ng/mL) Day 1 | Day 7 | $T_{max}$ (h) Day 1 | Day 7 | $AUC_{0-t}$ (ng · h/mL) Day 1 | Day 7 |
|---|---|---|---|---|---|---|
| 400 mg q.i.d. (n = 6) | 496 (150-1437) | 995 (425-2245) | 1.0 (0.5-3.0) | 0.25 (0.25-1.0) | 1593 (751-2646) | 10498 (2357-26748) |
| 800 mg q.i.d. (n = 6) | 2680 (1000-7767) | 1675 (913-2602) | 0.25 (0.25-0.50) | 0.25 (0.25-1.50) | 5182 (2384-10260) | 19938 (11675-29457) |
| 1600 mg t.i.d. (n = 6) | 2892 (708-7538) | 4893 (1601-11370) | 0.375 (0.250-0.500) | 0.5 (0.25-0.5) | 7093 (3919-12163) | 25797 (8686-34390) |
| 1600 mg q.i.d (n = 6) | 2797 (387-6416) | 5476 (1919-10972) | 0.5 (0.25-24) | 0.25 (0.25-0.5) | 8305 (4227-15418) | 24474 (11002-58509) |

Values are the mean with ranges (i.e. minimum and maximum values for individuals) in parentheses, except for $T_{max\ which\ is\ the\ median}$.
NC: Not calculated
Day 1 corresponds to parameters following a single oral administration.
Day 7 corresponds to parameters following repeated oral administration.

Example 6

The safety, efficacy and pharmacokinetics of PDS after single and multiple oral administration in subjects with AA amyloidosis is determined. This is a multicenter, multinational, randomized, double-blind, placebo-controlled, and parallel-design study to assess the pharmacokinetic profile of single and repeated doses of PDS. Dosing depends on the severity or renal impairment in a subject: subjects having creatinine clearance (ClCr) >80 mL/min receive 1200 mg BID; for ClCr between 30 and 80 mL/min, the subject receives 800 mg BID; and for ClCr between 20 and 30 mL/min, the subject receives 400 mg BID. If ClCr decreases to the next lower range level, the dose regimen is adjusted accordingly. PDS is administered as a single oral dose for a subset of AA amyloidosis patients on Month 0 and 24 visits. Following the single administration on Month 0, PDS is administered twice daily for 24 months. Blood samples are collected through 24 hours after the doses on Month 0 and 24, and through 8 hours after the doses on Month 4, 8, 12 visits. Plasma concentrations of PDS are determined using validated HPLC methods. Following multiple dose oral administration of PDS, the range of accumulation across subjects is 1.75 to 3.44. Based on the accumulation factor, the mean $T_{1/2}$ calculated is 15 hours with a range of 10 to 24 hours. Results are shown in Table 6.

TABLE 6

Pharmacokinetic Parameters of PDS after Single (Month 0) and Multiple (Month 24) Oral Administration to AA amyloidosis Patients
Parameters

| Dose | $C_{max}$ (ng/mL) Month 0 | Month 24 | $T_{max}$ (h) Month 0 | Month 24 | $AUC_{(0-12)}$ (ng * h/mL) Month 0 | Month 24 | $AUC_{(0-tlast)}$ (ng * h/mL) Month 0 | Month 24 |
|---|---|---|---|---|---|---|---|---|
| 400 | 841 (580-1101) n = 2 | 2157 (1482-2572) n = 3 | 3 (3-3) n = 2 | 1.83 (0.5-3) n = 3 | 7414 (4479-10358) n = 2 | 17557 (13315-25724) n = 3 | 11689 (6486-16893) n = 2 | 25699 (13315-42751) n = 3 |
| 800 | 812 (313-1177) n = 5 | 1897 (1114-2961) n = 4 | 2.95 (0.75-7.98) n = 5 | 1.85 (0.75-3) n = 4 | 5948 (2354-10319) n = 5 | 13692 (8265-22368) n = 4 | 9809 (3324-19359) n = 5 | 21171 (11399-37734) n = 4 |
| 1200 | 867 (420-1423) n = 4 | 637 (NA) n = 1 | 0.69 (0.5-1) n = 4 | 0.68 (NA) n = 1 | 4208 (2311-6688) n = 4 | 4928 (NA) n = 1 | 5633 (2707-10078) n = 4 | 9144 (NA) n = 1 |

Values are mean with ranges (i.e. minimum and maximum values for individuals) in parentheses.
Month 0 corresponds to parameters following a single oral dose.
Month 24 correspons to parameters following repeated oral doses.
n = number of patients in each dose group
NA = Not Applicable Example 7

An example of a formulation of a 400 mg capsule of 1,3 propanedisulfonic acid 20 disodium salt is described below.

Capsules of 400 mgs of 1,3 propanedisulfonic acid disodium salt are manufactured by filling # 0 white opaque hard gelatin capsules with a white powder comprised of 400 mg of 1,3 propanedisulfonic acid disodium salt and 40 mg of excipients.

| Raw Material | Grade | Function | Label (mg/unit) | % |
|---|---|---|---|---|
| 1,3 Propanedisulfonic Acid Disodium Salt (PDS) | MHS* | active | 400.0 | 90.9 |
| Lactose Monohydrate (316 Fast-Flo) | NF | diluent | 37.8 | 8.6 |

-continued

| Raw Material | Grade | Function | Label (mg/unit) | % |
|---|---|---|---|---|
| Magnesium Stearate | NF | lubricant | 2.2 | 0.5 |
| Sub-Total | | | 440.0 | 100.0 |
| # 0 Hard Gelatin Capsule | MHS* | capsule | 96.0 | |
| Total | | | 536.0 | |

*MHS—Manufacturer House Standard

Example 8

A pharmaceutical composition is formulated as described in Example 7 with 1,2-ethanedisulfonic acid as the active agent.

Example 9

A pharmaceutical composition is formulated as described in Example 7 with sodium 1,2-ethanedisulfonate as the active agent.

Example 10

A pharmaceutical composition is fonmulated as described in Example 7 with 1,2-ethanediol bis(hydrogen sulfate) as the active agent.

Example 11

A pharmaceutical composition is fonmulated as described in Example 7 with 1,2-ethanediol disulfate disodium salt as the active agent.

Example 12

A pharmaceutical composition is formulated as described in Example 7 with 1,3-propanediol bis(hydrogen sulfate) as the active agent.

Example 13

A pharmaceutical composition is formulated as described in Example 7 with 1,3-propanediol disulfate disodium salt as the active agent.

Example 14

A pharmaceutical composition is formulated as described in Example 7 with 2-sulfomethyl-1,4-butanedisulfonic acid as the active agent.

Example 15

A pharmaceutical composition is formulated as described in Example 7 with 2-sulfomethylbutane-1,4-disulfonic acid trisodium salt as the active agent.

Equivalents

Those skilled in the art will recognize, or be able to ascertain using no more than routine experimentation, numerous equivalents to the specific procedures described herein. Such equivalents are considered to be within the scope of the present invention and are covered by the following claims. The contents of all references, patents, and patent applications cited throughout this application are hereby incorporated by reference. The appropriate components, processes, and methods of those patents, applications and other documents may be selected for the present invention and embodiments thereof.

The invention claimed is:

1. A method of treating a patient suffering from AA amyloidosis and having renal impairment comprising
measuring a first creatinine clearance rate of the patient and determining it to be (a) less than about 30 mL/min, (b) from about 30 to about 80 mL/min or (c) greater than about 80 mL/min, and
orally administering to said patient, in dependence on which rate is found, respectively,
(a), a dose of 400 mg twice a day of an active agent which is 1,3-propane disulfonic acid or a pharmaceutically acceptable salt thereof, in a formulation with a pharmaceutically acceptable carrier, such that when said dose is orally administered to said patient for multiple administrations, a mean $C_{max}$ after a single administration of about 500-2,000 ng/mL±20% is achieved;
(b), dose of 800 mg twice a day of said active agent in a formulation with a pharmaceutically acceptable carrier, such that when said dose is orally administered to said patient for multiple administrations, a mean $C_{max}$ after a single administration of about 500-2,000 ng/mL±20% is achieved; or
(c), a dose of 1200 mg twice a day of said active agent, in a formulation with a pharmaceutically acceptable carrier, such that when said dose is orally administered to said patient for multiple administrations, a mean $C_{max}$ after a single administration of about 500-2,000 ng/mL±20% is achieved; and
measuring a second creatinine clearance rate of said patient and determining it to be in a different rate range (a), (b) or (c), as defined above, from said first creatinine clearance rate, and orally administering to said patient an active agent dose (a), (b) or (c) as defined above, corresponding to said different rate.

2. A method of claim 1, wherein the formulation is administered without food.

3. The method of claim 2, wherein the administration without food results in an increase in bioavailability of about 25% or greater compared to administration with food.

4. The method of claim 3, wherein the subject is informed to administer the composition at least 1 or 2 hours before or after any meals.

5. The method of claim 1 wherein said mean $C_{max}$ after a single administration for (a), (b) and (c) is about 850 ng/mL±50 ng/mL.

6. The method of claim 1, comprising measuring a third creatinine clearance rate of said patient and determining it to be in a different rate range (a), (b) or (c), as defined above, from said first and second creatinine clearance rates, and orally administering to said patient an active agent dose (a), (b) or (c) as defined above, corresponding to said different rate.

7. The method of claim 1 wherein creatinine clearance rate is stabilized or improved in the patient.

8. The method of claim 1, wherein said active agent is administered in combination with a second active agent.

9. The method of claim 8, wherein the second agent is selected from the group consisting of anti-inflammatory agents, colchicine, cytotoxic agents, chemotherapeutic agents, anti-TNF agents, antibiotics, and combinations thereof.

* * * * *